United States Patent
Shimada et al.

(10) Patent No.: US 12,350,050 B2
(45) Date of Patent: Jul. 8, 2025

(54) INTRALUMINAL MICRONEUROGRAPHY PROBES AND RELATED SYSTEMS AND METHODS

(71) Applicant: RECOR MEDICAL, INC., Palo Alto, CA (US)

(72) Inventors: Jin Shimada, White Bear Lake, MN (US); Harry Puryear, Shoreview, MN (US); Gregory Brucker, Minneapolis, MN (US)

(73) Assignee: Recor Medical, Inc., Palo Alto, CA (US)

( * ) Notice: Subject to any disclaimer, the term of this patent is extended or adjusted under 35 U.S.C. 154(b) by 917 days.

(21) Appl. No.: 17/453,636

(22) Filed: Nov. 4, 2021

(65) Prior Publication Data

US 2022/0095979 A1   Mar. 31, 2022

Related U.S. Application Data

(63) Continuation-in-part of application No. 16/517,180, filed on Jul. 19, 2019, now Pat. No. 11,642,061, and
(Continued)

(51) Int. Cl.
*A61B 5/294* (2021.01)
*A61B 5/00* (2006.01)
(Continued)

(52) U.S. Cl.
CPC ................ *A61B 5/24* (2021.01); *A61B 5/201* (2013.01); *A61B 5/294* (2021.01); *A61B 5/305* (2021.01);
(Continued)

(58) Field of Classification Search
CPC ........... A61B 5/283; A61B 5/287; A61B 5/30; A61B 5/305; A61B 5/6852; A61B 5/6877
See application file for complete search history.

(56) References Cited

U.S. PATENT DOCUMENTS 4,554,925 A   11/1985 Young
4,643,186 A   2/1987 Rosen et al.
(Continued)

FOREIGN PATENT DOCUMENTS

EP   1299035   4/2003
EP   1503685   2/2005
(Continued)

OTHER PUBLICATIONS

Final Office Action dated Apr. 22, 2019, U.S. Appl. No. 15/204,349, filed Jul. 7, 2016.
(Continued)

*Primary Examiner* — Eun Hwa Kim
(74) *Attorney, Agent, or Firm* — Theresa Ann Raymer

(57) ABSTRACT

Certain embodiments described herein relate to a system for use in analyzing neural activity of nerves surrounding a biological lumen. The system includes a probe body, electrodes, a stimulator, and an amplifier. The stimulator delivers electrical stimulation via a first pair of the electrodes, supported by the probe body, to test for an evoked neural response by nerves surrounding the biological lumen. The amplifier includes a pair of input terminals, an output terminal, and a ground reference terminal. A second pair of the electrodes is electrically coupled to the pair of input terminals of the amplifier, to thereby enable the amplifier to produce the sensed signal indicative of the evoked neural response. A remaining one of the electrodes, which is not included in the first and the second pairs of the electrodes, is electrically coupled to the ground reference terminal of the amplifier.

26 Claims, 20 Drawing Sheets

Related U.S. Application Data a continuation-in-part of application No. 15/943,354, filed on Apr. 2, 2018, now Pat. No. 11,510,731, said application No. 16/517,180 is a continuation of application No. 15/299,694, filed on Oct. 21, 2016, now abandoned, which is a continuation of application No. 15/204,349, filed on Jul. 7, 2016, now abandoned, said application No. 15/943,354 is a continuation of application No. 14/683,966, filed on Apr. 10, 2015, now Pat. No. 9,999,463.

(60) Provisional application No. 63/110,920, filed on Nov. 6, 2020, provisional application No. 62/198,382, filed on Jul. 29, 2015, provisional application No. 61/979,339, filed on Apr. 14, 2014.

(51) Int. Cl.
| | | |
|---|---|---|
| *A61B 5/20* | (2006.01) | |
| *A61B 5/24* | (2021.01) | |
| *A61B 5/305* | (2021.01) | |
| *A61B 18/14* | (2006.01) | |
| *A61B 18/18* | (2006.01) | |
| A61B 18/00 | (2006.01) | |
| A61B 18/12 | (2006.01) | |
| A61B 18/16 | (2006.01) | |

(52) U.S. Cl.
CPC ............ *A61B 5/4836* (2013.01); *A61B 5/725* (2013.01); *A61B 18/1492* (2013.01); *A61B 18/1815* (2013.01); *A61B 2018/00023* (2013.01); *A61B 2018/00267* (2013.01); *A61B 2018/00404* (2013.01); *A61B 2018/00434* (2013.01); *A61B 2018/00511* (2013.01); *A61B 2018/00577* (2013.01); *A61B 2018/00839* (2013.01); *A61B 2018/1253* (2013.01); *A61B 2018/1407* (2013.01); *A61B 2018/162* (2013.01); *A61B 2018/1861* (2013.01); *A61B 2562/028* (2013.01)

(56) References Cited

U.S. PATENT DOCUMENTS

| | | |
|---|---|---|
| 4,650,466 A | 3/1987 | Luther |
| 4,709,698 A | 12/1987 | Johnston et al. |
| 4,841,977 A | 6/1989 | Griffith et al. |
| 4,983,169 A | 1/1991 | Furukawa |
| 5,000,185 A | 3/1991 | Yock |
| 5,114,423 A | 5/1992 | Kasprzyk |
| 5,368,591 A | 11/1994 | Lennox |
| 5,391,197 A | 2/1995 | Brudette et al. |
| 5,423,811 A | 6/1995 | Imran et al. |
| 5,558,672 A | 9/1996 | Edwards et al. |
| 5,575,788 A | 11/1996 | Baker et al. |
| 5,657,755 A | 8/1997 | Desai |
| 5,685,839 A | 11/1997 | Edwards et al. |
| 5,688,266 A | 11/1997 | Edwards et al. |
| 5,800,482 A | 9/1998 | Pomeranz et al. |
| 6,066,134 A | 5/2000 | Eggers et al. |
| 6,097,985 A | 8/2000 | Kasevich et al. |
| 6,117,101 A | 9/2000 | Diederich et al. |
| 6,254,598 B1 | 7/2001 | Edwards |
| 6,283,989 B1 | 9/2001 | Laufer et al. |
| 6,292,695 B1 | 9/2001 | Webster et al. |
| 6,296,619 B1 | 10/2001 | Brisken et al. |
| 6,383,151 B1 | 5/2002 | Diederich et al. |
| 6,514,249 B1 | 2/2003 | Maguire et al. |
| 6,529,756 B1 | 3/2003 | Phan et al. |
| 6,564,096 B2 | 5/2003 | Mest |
| 6,584,360 B2 | 6/2003 | Francischelli et al. |
| 6,635,054 B2 | 10/2003 | Fjield et al. |
| 6,648,883 B2 | 11/2003 | Francischelli et al. |
| 6,669,655 B1 | 12/2003 | Acker |
| 6,692,490 B1 | 2/2004 | Edwards |
| 6,719,755 B2 | 4/2004 | Sliwa, Jr. et al. |
| 6,763,722 B2 | 7/2004 | Fjield et al. |
| 6,837,886 B2 | 1/2005 | Collins et al. |
| 6,845,267 B2 | 6/2005 | Harrison et al. |
| 6,954,977 B2 | 10/2005 | Maguire |
| 7,052,695 B2 | 5/2006 | Kalish |
| 7,156,816 B2 | 1/2007 | Schwartz et al. |
| 7,162,303 B2 | 1/2007 | Levin et al. |
| 7,203,546 B1 | 4/2007 | Kroll et al. |
| 7,371,231 B2 | 5/2008 | Rioux et al. |
| 7,510,536 B2 | 5/2009 | Foley et al. |
| 7,617,005 B2 | 11/2009 | Demarais et al. |
| 7,621,873 B2 | 11/2009 | Owen et al. |
| 7,653,438 B2 | 1/2010 | Deem et al. |
| 7,717,948 B2 | 5/2010 | Demarais et al. |
| 7,722,604 B2 | 5/2010 | Brown et al. |
| 7,799,021 B2 | 9/2010 | Leung et al. |
| 7,942,871 B2 | 5/2011 | Thapliyal et al. |
| 8,024,050 B2 | 9/2011 | Libbus et al. |
| 8,025,688 B2 | 9/2011 | Diederich et al. |
| 8,137,274 B2 | 3/2012 | Weng et al. |
| 8,224,416 B2 | 7/2012 | de la Rama et al. |
| 8,447,414 B2 | 5/2013 | Johnson et al. |
| 8,483,831 B1 | 7/2013 | Hlavka et al. |
| 8,702,619 B2 | 4/2014 | Wang |
| 8,774,913 B2 | 7/2014 | Demarais et al. |
| 8,790,281 B2 | 7/2014 | Diederich et al. |
| 8,818,514 B2 | 8/2014 | Zarins et al. |
| 8,845,629 B2 | 9/2014 | Demarais et al. |
| 8,876,813 B2 | 11/2014 | Min et al. |
| 8,909,316 B2 | 12/2014 | Ng |
| 8,932,289 B2 | 1/2015 | Mayse et al. |
| 9,014,821 B2 | 4/2015 | Wang |
| 9,022,948 B2 | 5/2015 | Wang |
| 9,028,472 B2 | 5/2015 | Mathur et al. |
| 9,066,720 B2 | 6/2015 | Ballakur et al. |
| 9,072,902 B2 | 7/2015 | Mathur et al. |
| 9,155,590 B2 | 10/2015 | Mathur |
| 9,186,198 B2 | 11/2015 | Demarais et al. |
| 9,186,212 B2 | 11/2015 | Nabutovsky et al. |
| 9,289,132 B2 | 3/2016 | Ghaffari |
| 9,326,816 B2 | 5/2016 | Srivastava |
| 9,327,123 B2 | 5/2016 | Yamasaki |
| 9,333,035 B2 | 5/2016 | Rudie et al. |
| 9,339,332 B2 | 5/2016 | Srivastava |
| 9,345,530 B2 | 5/2016 | Ballakur et al. |
| 9,375,154 B2 | 6/2016 | Wang |
| 7,717,948 C1 | 8/2016 | Demarais et al. |
| 9,427,579 B2 | 8/2016 | Fain et al. |
| 9,439,598 B2 | 9/2016 | Shimada et al. |
| 9,649,064 B2 | 5/2017 | Toth et al. |
| 9,723,998 B2 | 8/2017 | Wang |
| 9,730,639 B2 | 8/2017 | Toth et al. |
| 9,743,845 B2 | 8/2017 | Wang |
| 9,750,560 B2 | 9/2017 | Ballakur et al. |
| 9,770,291 B2 | 9/2017 | Wang et al. |
| 9,770,593 B2 | 9/2017 | Gross |
| 9,801,684 B2 | 10/2017 | Fain et al. |
| 9,820,811 B2 | 11/2017 | Wang |
| 9,907,983 B2 | 3/2018 | Thapliyal et al. |
| 9,931,047 B2 | 4/2018 | Srivastava |
| 9,943,666 B2 | 4/2018 | Warnking |
| 9,956,034 B2 | 5/2018 | Toth et al. |
| 9,968,790 B2 | 5/2018 | Toth et al. |
| 9,981,108 B2 | 5/2018 | Warnking |
| 9,999,463 B2 | 6/2018 | Puryear et al. |
| 10,004,458 B2 | 6/2018 | Toth et al. |
| 10,004,557 B2 | 6/2018 | Gross et al. |
| 10,010,364 B2 | 7/2018 | Harrington |
| 10,016,233 B2 | 7/2018 | Pike |
| 10,022,085 B2 | 7/2018 | Toth et al. |
| 10,039,901 B2 | 8/2018 | Warnking |
| 10,111,708 B2 | 10/2018 | Wang |
| 10,123,903 B2 | 11/2018 | Warnking et al. |
| 10,143,419 B2 | 12/2018 | Toth et al. |
| 10,179,020 B2 | 1/2019 | Ballakur et al. |
| 10,179,026 B2 | 1/2019 | Ng |

(56) References Cited

U.S. PATENT DOCUMENTS

| | | | |
|---|---|---|---|
| 10,182,865 B2 | 1/2019 | Naga et al. | |
| 10,226,633 B2 | 3/2019 | Toth et al. | |
| 10,292,610 B2 | 5/2019 | Srivastava | |
| 10,293,190 B2 | 5/2019 | Zarins et al. | |
| 10,363,359 B2 | 7/2019 | Toth et al. | |
| 10,368,775 B2 | 8/2019 | Hettrick et al. | |
| 10,376,310 B2 | 8/2019 | Fain et al. | |
| 10,383,685 B2 | 8/2019 | Gross et al. | |
| 10,398,332 B2 | 9/2019 | Min et al. | |
| 10,470,684 B2 | 11/2019 | Toth et al. | |
| 10,478,249 B2 | 11/2019 | Gross et al. | |
| 10,499,937 B2 | 12/2019 | Warnking | |
| 10,543,037 B2 | 1/2020 | Shah | |
| 10,850,091 B2 | 12/2020 | Zarins et al. | |
| 11,801,085 B2 | 10/2023 | Wu et al. | |
| 2001/0023365 A1 | 9/2001 | Medhkour et al. | |
| 2002/0042610 A1 | 4/2002 | Sliwa, Jr. et al. | |
| 2002/0072741 A1 | 6/2002 | Sliwa, Jr. et al. | |
| 2002/0165535 A1 | 11/2002 | Lesh | |
| 2002/0173724 A1 | 11/2002 | Dorando et al. | |
| 2002/0193681 A1 | 12/2002 | Vitek et al. | |
| 2003/0004439 A1 | 1/2003 | Pant et al. | |
| 2003/0028111 A1 | 2/2003 | Vaezy et al. | |
| 2003/0074039 A1 | 4/2003 | Puskas | |
| 2003/0114878 A1 | 6/2003 | Diederich et al. | |
| 2003/0125726 A1 | 7/2003 | Maguire et al. | |
| 2003/0181963 A1 | 9/2003 | Pellegrino et al. | |
| 2003/0216721 A1 | 11/2003 | Diedrich et al. | |
| 2003/0216792 A1 | 11/2003 | Levin | |
| 2004/0019349 A1 | 1/2004 | Fuimaono et al. | |
| 2004/0082859 A1 | 4/2004 | Schaer | |
| 2004/0097819 A1 | 5/2004 | Duarte | |
| 2004/0106880 A1 | 6/2004 | Weng et al. | |
| 2004/0122494 A1 | 6/2004 | Eggers et al. | |
| 2004/0181178 A1 | 9/2004 | Aldrich et al. | |
| 2004/0242999 A1 | 12/2004 | Vitek et al. | |
| 2005/0038340 A1 | 2/2005 | Vaezy et al. | |
| 2005/0159738 A1* | 7/2005 | Visram | A61B 18/1492 606/41 |
| 2005/0203501 A1 | 9/2005 | Aldrich et al. | |
| 2005/0215990 A1 | 9/2005 | Govari | |
| 2005/0228283 A1 | 10/2005 | Gifford et al. | |
| 2005/0228459 A1 | 10/2005 | Levin et al. | |
| 2005/0228460 A1 | 10/2005 | Levin et al. | |
| 2005/0261672 A1 | 11/2005 | Deem et al. | |
| 2005/0288730 A1 | 12/2005 | Deem et al. | |
| 2006/0041277 A1 | 2/2006 | Deem et al. | |
| 2006/0052695 A1 | 3/2006 | Adam et al. | |
| 2006/0058711 A1 | 3/2006 | Harhen et al. | |
| 2006/0064081 A1 | 3/2006 | Rosinko | |
| 2006/0118127 A1 | 6/2006 | Chinn | |
| 2006/0142827 A1 | 6/2006 | Willard et al. | |
| 2006/0184069 A1 | 8/2006 | Vaitekunas | |
| 2006/0217772 A1 | 9/2006 | Libbus et al. | |
| 2006/0235286 A1 | 10/2006 | Stone et al. | |
| 2007/0060921 A1 | 3/2007 | Janssen et al. | |
| 2007/0072741 A1 | 3/2007 | Robideau et al. | |
| 2007/0106292 A1 | 5/2007 | Kaplan et al. | |
| 2007/0135875 A1 | 6/2007 | Demarais et al. | |
| 2008/0039746 A1 | 2/2008 | Hissong et al. | |
| 2008/0215031 A1 | 9/2008 | Belfort et al. | |
| 2009/0234407 A1 | 9/2009 | Hastings et al. | |
| 2009/0248005 A1 | 10/2009 | Rusin et al. | |
| 2011/0118723 A1 | 5/2011 | Turner et al. | |
| 2011/0125206 A1 | 5/2011 | Bornzin et al. | |
| 2011/0208096 A1 | 8/2011 | Demarais et al. | |
| 2012/0004656 A1 | 1/2012 | Jackson et al. | |
| 2012/0232374 A1 | 9/2012 | Werneth et al. | |
| 2012/0265198 A1 | 10/2012 | Crow et al. | |
| 2012/0296232 A1 | 11/2012 | Ng | |
| 2013/0023897 A1 | 1/2013 | Wallace | |
| 2013/0085489 A1 | 4/2013 | Fain | |
| 2013/0096550 A1 | 4/2013 | Hill | |
| 2013/0116737 A1 | 5/2013 | Edwards et al. | |
| 2013/0123770 A1 | 5/2013 | Smith | |
| 2013/0131743 A1 | 5/2013 | Yamasaki et al. | |
| 2013/0150749 A1 | 6/2013 | McLean et al. | |
| 2013/0165925 A1 | 6/2013 | Mathur et al. | |
| 2013/0172872 A1 | 7/2013 | Subramaniam | |
| 2013/0274614 A1 | 10/2013 | Shimada | |
| 2013/0289369 A1 | 10/2013 | Margolis | |
| 2013/0289682 A1 | 10/2013 | Barman et al. | |
| 2014/0018788 A1 | 1/2014 | Engelman et al. | |
| 2014/0058294 A1 | 2/2014 | Gross et al. | |
| 2014/0257271 A1 | 9/2014 | Mayse et al. | |
| 2014/0275924 A1 | 9/2014 | Min et al. | |
| 2014/0288551 A1 | 9/2014 | Bharmi | |
| 2014/0288616 A1 | 9/2014 | Rawat et al. | |
| 2014/0303617 A1 | 10/2014 | Shimada | |
| 2015/0289931 A1* | 10/2015 | Puryear | A61B 18/1492 606/41 |
| 2016/0000345 A1 | 1/2016 | Kobayashi et al. | |
| 2016/0045121 A1 | 2/2016 | Akingba et al. | |
| 2017/0027460 A1* | 2/2017 | Shimada | A61B 18/1492 |
| 2017/0035310 A1 | 2/2017 | Shimada et al. | |
| 2017/0296264 A1 | 10/2017 | Wang | |
| 2018/0022108 A1 | 1/2018 | Mori et al. | |
| 2018/0042670 A1 | 2/2018 | Wang et al. | |
| 2018/0064359 A1 | 3/2018 | Pranaitis et al. | |
| 2018/0078307 A1 | 3/2018 | Wang et al. | |
| 2018/0185917 A1 | 7/2018 | Toth et al. | |
| 2018/0192959 A1* | 7/2018 | Mou | A61B 18/1492 |
| 2018/0221087 A1 | 8/2018 | Puryear et al. | |
| 2018/0249958 A1 | 9/2018 | Toth et al. | |
| 2018/0250054 A1 | 9/2018 | Gross et al. | |
| 2018/0280082 A1 | 10/2018 | Puryear et al. | |
| 2018/0289320 A1 | 10/2018 | Toth et al. | |
| 2018/0310991 A1 | 11/2018 | Pike | |
| 2018/0333204 A1 | 11/2018 | Ng | |
| 2019/0046111 A1 | 2/2019 | Toth et al. | |
| 2019/0046264 A1 | 2/2019 | Toth et al. | |
| 2019/0076191 A1 | 3/2019 | Wang | |
| 2019/0110704 A1 | 4/2019 | Wang | |
| 2019/0134396 A1 | 5/2019 | Toth et al. | |
| 2019/0151670 A1 | 5/2019 | Toth et al. | |
| 2019/0183560 A1 | 6/2019 | Ballakur et al. | |
| 2019/0307361 A1 | 10/2019 | Hettrick et al. | |
| 2020/0038101 A1* | 2/2020 | Tobey | A61B 18/1206 |
| 2020/0046248 A1 | 2/2020 | Toth et al. | |
| 2020/0077907 A1 | 3/2020 | Shimada et al. | |
| 2021/0369132 A1* | 12/2021 | Van Niekerk | A61B 5/6859 |

FOREIGN PATENT DOCUMENTS

| | | |
|---|---|---|
| EP | 1579889 | 9/2005 |
| EP | 2359764 | 8/2011 |
| EP | 2430996 | 3/2012 |
| EP | 2842604 | 3/2015 |
| EP | 2968984 | 1/2016 |
| EP | 2995250 | 3/2016 |
| EP | 3799931 | 4/2021 |
| WO | WO1999/002096 | 1/1999 |
| WO | WO2001/095820 | 12/2001 |
| WO | WO2002/005897 | 1/2002 |
| WO | WO 2002/019934 | 3/2002 |
| WO | WO2003/022167 | 3/2003 |
| WO | WO2003/051450 | 6/2003 |
| WO | WO2006/041881 | 4/2006 |
| WO | WO2006/060053 | 6/2006 |
| WO | WO2007/014003 | 2/2007 |

OTHER PUBLICATIONS

Response to Office Action dated Jul. 9, 2019, U.S. Appl. No. 15/204,349, filed Jul. 7, 2016.
Advisory Action dated Jul. 9, 2019, U.S. Appl. No. 15/204,349, filed Jul. 7, 2016.
Restriction Requirement dated Aug. 6, 2018, U.S. Appl. No. 15/299,694, filed Oct. 21, 2016.
Response to Restriction dated Oct. 8, 2018, U.S. Appl. No. 15/299,694, filed Oct. 21, 2016.
Non-final Office Action dated Nov. 27, 2018, U.S. Appl. No. 15/299,694, filed Oct. 21, 2016.

(56) References Cited

OTHER PUBLICATIONS

Response to Office Action dated Feb. 27, 2019, U.S. Appl. No. 15/299,694, filed Oct. 21, 2016.
Final Office Action dated Apr. 22, 2019, U.S. Appl. No. 15/299,694, filed Oct. 21, 2016.
Response to Office Action dated Jun. 24, 2019, U.S. Appl. No. 15/299,694, filed Oct. 21, 2016.
Advisory Action dated Jul. 9, 2019, U.S. Appl. No. 15/299,694, filed Oct. 21, 2016.
Preliminary Amendment dated Jul. 19, 2019, U.S. Appl. No. 16/517,180 filed Jul. 19, 2019.
Ahmed, Muneeb et al., "Thermal Ablation Therapy for Hepatocellular Carcinoma," J. Vasc. Interv, Radiol., vol. 13, No. 9 pt. 2, 2002.
Benito, Fernando et al., "Radiofrequency catheter ablation of accessary pathways in infants," Heart, vol. 78, p. 160-162, 1997.
Chang, Isaac A. et al., "Thermal Modeling of Lesion Growth with Radiofrequency Ablation Devices," Biomedical Engineering Online vol. 3, p. 27, 2004.
Chung, Andrew et al., "Thermal dosimetry of a focused ultrasound beam in vivo by magnetic resonance imaging," Medical Physics, vol. 26, No. 9, p. 2017-2026, Sep. 1999.
Damianou, Christakis et al., "High Intensity Focused Ultrasound Ablation of Kidney Guided MRI," Ultrasound in Med. & Biol., vol. 30, No. 3, p. 397-404, 2004.
Deardorff, Dana L. et al., "Axial Control of Thermal Coagulation Using a Multi-Element Interstitial Ultrasound Applicator with Internal Cooling," IEE Transactions on Ultrasonics, Ferroelectrics, and Frequency Control, vol. 47, No. 1, p. 170-178, Jan. 2000.
Dewhirst, M.W. et al., "Basic Principles of Thermal Dosimetry and Thermal Thresholds for Tissue Damage from Hyperthermia," International Journal of Hyperthermia vol. 19, No. 3, p. 267-294, May-Jun. 2003.
Diederich, Chris J. et al., "Ultrasound Technology for Hyperthermia," Ultrasound in Med. & Biol., vol. 25, No. 6, p. 871-887, 1999.
Fry, F.J. et al., "Production of Reversible Changes in the Central Nervous System by Ultrasound," Science, vol. 127, p. 83-84, Jan. 1958.
Gavrilov, L.R. et al., The Effect of Focused Ultrasound on the Skin and Deep Nerve Structures of Man and Animal, p. 279-292.
Gavrilov, L.R., "Use of Focused Ultrasound for Stimulation of Nerve Structures," Ultrasonics, p. 132-138, May 1984.
Graham, S.J. et al., "Quantifying Tissue Damage Due to Focused Ultrasound Heating Observed by MRI" Magnetic Resonance in Medicine vol. 41, p. 321-328, 1999.
Goldberg, S. Nahum et al., "Radiofrequency Tissue Ablation: Increased Lesion Diameter with a Perfusion Electrode," Acad. Radiol. vol. 3, No. 8, p. 636-644, Aug. 1996.
Hacker, Axel et al., "Extracorporeal Organotripsy for Renal Tumours," Current Opinion in Urology, vol. 13, p. 221-225, 2003.
Hausberg, Martin et al., "Sympathetic Nerve Activity in End-Stage Renal Disease," Circulation, vol. 106, p. 1974-1979, 2002.
Ho, Siew Yen et al., "Anatomy of the Left Atrium: Implications for Radiofrequency Ablation of Atrial Fibrillation," J Cardiovasc Electrophysiol., vol. 10, p. 1525-1533, Nov. 1999.
Israel, Gary M. et al., "MRI of the Kidney and Urinary Tract," Journal of Magnetic Resonance Imaging, vol. 24, p. 725-734, 2006.
Jiang, S.C. et al., "Effects of Thermal Properties and Geometrical Dimensions on Skin Burn Injuries," Burns, vol. 28, p. 713-717, 2002.
Kaye, David M. et al., "Functional and Neurochemical Evidence for Partial Cardiac Sympathetic Reinnervation After Cardiac Transplantation in Humans," Circulation, vol. 88, No. 3, Sep. 1993.
Keane, David, "New Catheter Ablation Techniques for the Treatment of Cardiac Arrhythmias," Cardiac Electrophysiology Review vol. 6, No. 4, p. 341-348, 2002.
Kennedy, J.E. et al., "High Intensity Focused Ultrasound: Surgery of the Future?", The British Journal of Radiology, vol. 76, p. 590-599, Sep. 2003.
Lai, Yu-Chi et al., "Lesion Size Estimator of Cardiac Radiofrequency Ablation at Different Common Locations with Different Tip Temperatures," IEEE Transactions on Biomedical Engineering vol. 51, No. 10, p. 1859-1864, Oct. 2004.
Lauder, Lucas et al., "Renal Denervation in the Management of Hypertension," EuroIntervention, vol. 20, p. e467-e478, 2024.
Lele, P.P., "Effects of Focused Ultrasonic Radiation on Peripheral Nerve, with Observations on Local Heating," Experimental Neurology, vol. 8, p. 47-83, 1963.
Liao, Qingyao et al., "Optimal Strategy for HIFU-Based Renal Sympathetic Denervation in Canines," Frontiers in Cardiovascular Medicine vol. 8, p. 1-11, Oct. 2021.
Liem, L. Bing, "Progress in Cardiac Arrhythmia Ablation: Potential for Broader Application and Shorter Procedure Time," Journal of Cardiothoracic and Vascular Anesthesia, vol. 11, No. 7, p. 895-900, Dec. 1997.
Lin, James C., "Physical Aspects of Radiofrequency Ablation," Radiofrequency Catheter Ablation of Cardiac Arrhythmias, Basical Concepts and Clinical Applications, Second Edition, Edited by Shoei K. Stephen Huang & David K. Wilber, 2000.
Mahfoud, Felix et al., "Device Therapy of Hypertension," Circulation Research nol. 128, p. 1080-1099, Apr. 2021.
Makin, Inder Raj. S. et al., "Miniaturized Ultrasound Arrays for Interstitial Ablation and Imaging," Ultrasound in Med. & Biol. vol. 31, No. 11, p. 1539-1550, 2005.
Malcolm, A.L. et al., "Ablation of Tissue Volumes Using High Intensity Focused Ultrasound" Ultrasound in Med. & Biol. vol. 22 No. 5 p. 659-669, 1996.
Manolis, Antonis S. et al., "Radiofrequency Catheter Ablation for Cardiac Tachyarrhythmias," Annals of Internal Medicine, vol. 131, No. 6, p. 452-461, Sep. 1994.
Mitchell, G.A.G et al., "An Anatomical Evaluation of Operations for Hypertension," Proceedings of the Anatomical Society vol. LIV., No. 10, p. 545-560.
Mompeo, Blanca et al., "The Gross Anatomy of the Renal Sympathetic Nerves Revisited," Clinical Anatomy vol. 29, p. 660-664, Apr. 2016.
Moore, J.H. et al., "The Biophysical Effects of Ultrasound on Median Nerve Distal Latencies," Electromyogr. Clin. Neurophysiol., vol. 40, p. 169-190, 2000.
Nath, Sunil et al., "Basic Aspects of Radiofrequency Catheter Ablation," Journal of Cardiovascular Electrophysiology vol. 5, No. 10, p. 863-876, Oct. 1994.
Nath, Sunil et al., "Biophysics and Pathology of Catheter Energy Delivery Systems," Progress in Cardiovascular Diseases, vol. XXXVII, No. 4, p. 185-204, Jan./Feb. 1995.
Nau, William H. et al., "MRI-Guided Interstitial Ultrasound Thermal Therapy of the Prostate: A Feasibility Study in the Canine Model," Medical Physics vol. 32, No. 3, p. 733-743, Mar. 2005.
Nikfarjam, Mehrdad et al., "Mechanisms of Focal Heat Destruction of Liver Tumors," Journal of Surgical Research, vol. 127, No. 2, p. 208-223, Aug. 2005.
Ninet, Jean et al., "Surgical Ablation of Atrial Fibrillation With Off-Pump, Epicardial, High-Intensity Focused Ultrasound: Results of A Multicenter Trial," The Journal of Thoracic and Cardiovascular Surgery, vol. 130, No. 3, p. 803.e1-803e.8, Sep. 2005.
Ohkubo, Toyoyuki et al., "Experimental Study of Catheter Ablation Using Ultrasound Energy in Canine and Porcine Hearts," Jpn. Heart J. vol. 39, No. 3, p. 399-409, May 1998.
Papademetriou, Vasilios et al., "Renal Nerve Ablation for Resistant Hypertension, How Did We Get Here, Present Status, and Future Directions," Circulation, No. 129, p. 1440-1451, 2014.
Pozzoli, Alberto et al., "Electrophysiological Efficacy of Epicor High-Intensity Focused Ultrasound," European Journal of Cardio-Thoracic surgery, vol. 42, p. 129-134, 2012.
Riis, Thomas et al., "Effective Ultrasonic Stimulation in Human Peripheral Nervous System," IEE Transactions on Biomedical Engineering, vol. XX, No. XX, p. 1-8, XXXX 2021.
Roux, N. et al., "The Myocardial Sleeves of the Pulmonary Veins: Potential Implications for Atrial Fibrillation," Surg. Radiol. Anat., vol. 26, p. 285-289, Feb. 2004.
Schuarte, Patrick et al., "Catheter Ablation of Cardiac Autonomic Nerves for Prevention of Vagal Atrial Fibrillation," Circulation vol. 102, p. 2774-2780, 2000.

(56) References Cited

OTHER PUBLICATIONS

Tellez, Armando et al., "Renal Artery Nerve Distribution and Density in the Porcine Model: Biologic Implications for the Development of Radiofrequency Ablation Therapies," Translational Research vol. 162 No. 6, p. 381-389, Dec. 2013.
Ter Haar, G., "Ultrasound Focal Beam Surgery," Ultrasound in Med. & Biol., vol. 21, No. 9, p. 1089-1100, 1995.
Ter Haar, G.R. et al., "Ultrasonic Heating of Mammalian Tissues In vivo," Br. J. Cancer vol. 45, Supp. V., p. 65-67, 1982.
Ter Haar, Gail R. "Therapeutic and Surgical Applications," Physical Principles of Medical Ultrasonics, Second Edition, Edited by C.R. Hill, J.C. Bamber, and G.R. Ter Haar, p. 407-456, 2004.
Trippodo, Nick C. et al., "Similarities of Genetic (Spontaneous) Hypertension," Circulation Research vol. 48, No. 3, p. 309-319, Mar. 1981.
Urban, Bruce A. et al., "Three-dimensional vol. rendered CT Angiography of the Renal Arteries and Veins: Normal Anatomy, Variants, and Clinical Applications," RG vol. 21 No. 2, p. 373-386, Mar.-Apr. 2001.
Wang, Shyh-Hau et al., "Effects of Low Intensity Ultrasound on the Conduction Property of Neural Tissues," IEEE International Ultrasonics, Ferroelectrics, and Frequency Control Joint $50^{th}$ Anniversary Conference, p. 1824-1827, 2004.
Weld, Kyle J. et al., "Comparison of Cryoablation, Radiofrequency Ablation and High-Intensity Focused Ultrasound for Treating Small Renal Tumours" BJU International vol. 96, p. 1224-1229, 2005.
Wells, P.N.T., "Functional Modification: Clinical Applications," Biomedical Ultrasonics, p. 470-504, 1977.
Winternitz, Sherry R. et al., "Importance of the Renal Nerves in the Pathogenesis of Experimental Hypertension," Hypertension (supp. III), vol. 4, No. 5, p. III-08-III-115, Sep.-Oct. 1982.
Wulff, V.J. et al., "Effects of Ultrasonic Vibrations on Nerve Tissues," P.S.E.B.M., vol. 76, p. 361-366, 1951.
Yarmolenko, Pavel S. et al., "Thresholds for thermal damage to normal tissues: An update," Int. J. Hyperthermia, vol. 27 No. 4, p. 320-343, Jun. 2011.
Young, Robert R. et al., "Functional Effects of Focused Ultrasound on Mammalian Nerves," Science, vol. 134, p. 1521-1522, Nov. 1961.
Zimmer, J.E. et al., "The Feasibility of Using Ultrasound for Cardiac Ablation," IEEE Transactions on Biomedical Engineering, vol. 42, No. 9, p. 891-897, Sep. 1995.
Notice of Allowance dated Aug. 11, 2022, U.S. Appl. No. 15/943,354, filed Apr. 2, 2018.
Response to Office Action dated Aug. 22, 2022, U.S. Appl. No. 16/517,180, filed Jul. 19, 2019.
Non-final Office Action dated Dec. 20, 2021, U.S. Appl. No. 15/943,354, filed Apr. 2, 2018.
Final Office Action dated Jun. 15, 2022, U.S. Appl. No. 15/943,354, filed Apr. 2, 2018.
Response to Office Action dated Jul. 12, 2022, U.S. Appl. No. 15/943,354, filed Apr. 2, 2018.
A. Diedrich et al., Analysis of Raw Microneurographic Recordings Based on Wavelet De-Noising Technique and Classification Algorithm: Wavelet Analysis in Microneurography, IEEE Trans Biomed Eng. Jan. 2003 ; 50(1): 41-50. doi:10.1109/TBME.2002.807323.
J. Carter, Microneurography and Sympathetic Nerve Activity: A Decade-By-Decade Journey across 50 Years, Journal of Neurophysiology, vol. 121, No. 4. doi:10.1152/jn.00570.2018.
R. R. Harrison et al., A Low-Power Integrated Circuit for a Wireless 100-Electrode Neural Recording System, IEEE Journal of Solid-State Circuits, vol. 42, No. 1, pp. 123-133, Jan. 2007. doi: 10.1109/JSSC.2006.886567.
G.K.K. Nair et al., The Need For and the Challenges of Measuring Renal Sympathetic Nerve Activity, Heart Rhythm 2016; 13:1166-1171.
R. Olsson and K. Wise, A Three-Dimensional Neural Recording Microsystem With Implantable Data Compression Circuitry, ISSCC. 2005 IEEE International Digest of Technical Papers. Solid-State Circuits Conference, 2005., San Francisco, CA, 2005, pp. 558-559 vol. 1. doi: 10.1109/JSSC.2005.858479.
J. Osborn, Catheter-Based Renal Nerve Ablation as a Novel Hypertension Therapy, Lost, and Then Found, in Translation.
A. Salmanpour, L. J. Brown and J. K. Shoemaker, Detection of Single Action Potential in Multi-Unit Postganglionic Sympathetic Nerve Recordings in Humans: A Matched Wavelet Approach, 2010 IEEE International Conference on Acoustics, Speech and Signal Processing, Dallas, TX, 2010, pp. 554-557. doi: 10.1109/ICASSP. 2010.5495604.
M. P. Schlaich et al., Renal Denervation: A Potential New Treatment Modality for Polycystic Ovary Syndrome?, Journal of Hypertension, vol. 29, No. 5, pp. 991-996 2011. doi:10.1097/HJH. 0b013e328344db3a.
J. Tank et al., Spike Rate of Multi-Unit Muscle Sympathetic Nerve Fibers Following Catheter-Based Renal Nerve Ablation, J Am. Soc Hypertens, Oct. 2015 ; 9(10): 794-801. doi:10.1016/j.jash.2015.07. 012.
J. Xu et al., A Bidirectional Neuromodulation Technology for Nerve Recording and Stimulation, Micromachines, vol. 9,11 538. Oct. 23, 2018. doi:10.3390/mi9110538.
J. Xu, T. Wu and Z. Yang, A New System Architecture for Future Long-Term High-Density Neural Recording, IEEE Transactions on Circuits and Systems II: Express Briefs, vol. 60, No. 7, pp. 402-406, Jul. 2013. doi:10.1109/TCSII.2013.2258270.
N. Ivanisevic, "Circuit Design Techniques for Implantable Closed-Loop Neural Interfaces," Doctoral Thesis in Information and Communication Technology, KTH School of Electrical Engineering and Computer Science, Sweden, May 2019, 92 pages.
H. Heffner et al., "Gain, Band Width, and Noise Characteristics of the Variable-Parameter Amplifier," Journal of Applied Physics, vol. 29, No. 9, Sep. 1958, 11 pages.
P. Maslov, "Recruitment Pattern of Muscle Sympathetic Nerve Activity in Chronic Stable Heart Failure Patients and in Healthy Control Subjects," Doctoral Dissertation, University of Split, Croatia, 2013, 68 pages.
M.B.I. Reaz et al., "Techniques of EMG signal analysis: detection, processing, classification and applications," Biological Procedures Online, Jan. 2006, 25 pages.
Accornero, Neri, et al., "Selective Activation of Peripheral Nerve Fibre Groups of Different Diameter By Triangular Shaped Stimulus Pulses," J. Physio. 1977, 22 pages.
Papademetriou et al., "Renal Sympathetic Denervation: Hibernation or Resurrection?" Cardiology 2016, 11 pages.
Non-final Office Action dated Jun. 12, 2017, U.S. Appl. No. 14/683,966, filed Apr. 10, 2015.
Response to Office Action dated Nov. 10, 2017, U.S. Appl. No. 14/683,966, filed Apr. 10, 2015.
Notice of Allowance dated Jan. 31, 2018, U.S. Appl. No. 14/683,966, filed Apr. 10, 2015.
Amendment under 37 CFR 1.312 dated Mar. 13, 2018, U.S. Appl. No. 14/683,966, filed Apr. 10, 2015.
Preliminary Amendment dated Apr. 3, 2018, U.S. Appl. No. 15/943,354, filed Apr. 2, 2018.
Restriction Requirement dated Nov. 20, 2019, U.S. Appl. No. 15/943,354, filed Apr. 2, 2018.
Response to Restriction dated Dec. 19, 2019, U.S. Appl. No. 15/943,354, filed Apr. 2, 2018.
Non-final Office Action dated Jan. 13, 2020, U.S. Appl. No. 15/943,354, filed Apr. 2, 2018.
Response to Office Action dated Jul. 20, 2020, U.S. Appl. No. 15/943,354, filed Apr. 2, 2018.
Final Office Action dated Dec. 10, 2020, U.S. Appl. No. 15/943,354, filed Apr. 2, 2018.
Response to Final Office Action dated Jan. 22, 2021, U.S. Appl. No. 15/943,354, filed Apr. 2, 2018.
Advisory Action dated Feb. 19, 2021, U.S. Appl. No. 15/943,354, filed Apr. 2, 2018.
Non-final Office Action dated Apr. 15, 2021, U.S. Appl. No. 15/943,354, filed Apr. 2, 2018.
Response to Office Action dated Jun. 22, 2021, U.S. Appl. No. 15/943,354, filed Apr. 2, 2018.

(56) References Cited

OTHER PUBLICATIONS

Non-final Office Action dated Nov. 1, 2021, U.S. Appl. No. 15/943,354, filed Apr. 2, 2018.
Preliminary Amendment dated Jun. 5, 2018, U.S. Appl. No. 15/996,978, filed Jun. 4, 2018.
Restriction Requirement dated Feb. 7, 2020, U.S. Appl. No. 15/996,978, filed Jun. 4, 2018.
Response to Restriction dated Apr. 6, 2020, U.S. Appl. No. 15/996,978, filed Jun. 4, 2018.
Restriction Requirement dated Apr. 16, 2020, U.S. Appl. No. 15/996,978, filed Jun. 4, 2018.
Response to Restriction dated May 1, 2020, U.S. Appl. No. 15/996,978, filed Jun. 4, 2018.
Non-final Office Action dated Jun. 11, 2020, U.S. Appl. No. 15/996,978, filed Jun. 4, 2018.
Response to Office Action dated Aug. 20, 2020, U.S. Appl. No. 15/996,978, filed Jun. 4, 2018.
Final Office Action dated Feb. 19, 2021, U.S. Appl. No. 15/996,978, filed Jun. 4, 2018.
Response to Office Action dated May 18, 2021, U.S. Appl. No. 15/996,978, filed Jun. 4, 2018.
Final Office Action dated Jun. 16, 2021, U.S. Appl. No. 15/996,978, filed Jun. 4, 2018.
Response to Office Action dated Jul. 20, 2021, U.S. Appl. No. 15/996,978, filed Jun. 4, 2018.
Non-final Office Action dated Sep. 2, 2021, U.S. Appl. No. 15/996,978, filed Jun. 4, 2018.
Response to Office Action dated Sep. 22, 2021, U.S. Appl. No. 15/996,978, filed Jun. 4, 2018.
Notice of Allowance dated Oct. 6, 2021, U.S. Appl. No. 15/996,978, filed Jun. 4, 2018.
Restriction Requirement dated May 17, 2018, U.S. Appl. No. 15/204,349, filed Jul. 7, 2016.
Response to Restriction dated Jun. 5, 2018, U.S. Appl. No. 15/204,349, filed Jul. 7, 2016.
Non-final Office Action dated Nov. 27, 2018, U.S. Appl. No. 15/204,349, filed Jul. 7, 2016.
Response to Office Action dated Feb. 27, 2019, U.S. Appl. No. 15/204,349, filed Jul. 7, 2016.
Non-final Office Action dated Apr. 20, 2022, U.S. Appl. No. 16/517,180, filed Jul. 19, 2019.
Response to Office Action dated Apr. 20, 2022, U.S. Appl. No. 15/943,354, filed Apr. 2, 2018.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 758-765 (2012).
American Heart Association—Pulmonary Hypertension: High Blood Pressure in the Heart-to-Lung System, (last reviewed Oct. 31, 2016).
Appeal Brief of Patent Owner from Reexamination 95-002,110, Nov. 16, 2012.
Aytac, et al., "Correlation Between the Diameter of the Main Renal Artery and the Presence of an Accessory Renal Artery", J Ultrasound Med 22:433-439, 2003.
Azizi, Michel et al., Ultrasound renal denervation for hypertension resistant to a triple medication pill (Radiance-HTN Trio): a randomised, multicentre, single-blind, sham-controlled trial, 397 Lancet 2476 (2021).
Bailey, M.R. et al., Physical Mechanisms of the Therapeutic Effect of Ultrasound (A Review), Acoustical Physics, vol. 49, No. 4, 2003, pp. 369-388.
Bengel, et al., Serial Assessment of Sympathetic Reinnervation After Orthotopic Heart Transplantation; A Longitudinal Study Using PET and C-11 Hydroxyephedrine, Circulation. 1999;99: 1866-1871.
Berjano, E. et al., "A Cooled Intraesophageal Balloom to Prevent Thermal Injury during Endocardial Surgical Radiofrequency Ablation of the left Atrium: a finite element study." Physics in Medicine and Biology, 50(20): 269-279, 2015.

Bhatt, D.L., et al., A Controlled Trial of Renal Denervation for Resistant Hypertension, New England J. Med., 370:1393-1401 (2014).
Bhatt, Deepak L. et al., Long-term outcomes after catheter-based renal artery denervation for resistant hypertension: final follow-up of the randomised Symplicity HTN-3 Trial, 400 Lancet 1405 (2022).
Billard, B.E. et al., Effects of Physical Parameters on High Temperature Ultrasound Hyperthermia, Ultrasound in Med. & Biol. vol. 16, No. 4, pp. 409-420, 1990.
Bisdas, Theodosios et al., Initial Experience with the 6-F and 8-F Indigo Thrombectomy System for Acute Renovisceral Occlusive Events, Journal of Endovascular Therapy, vol. 24, No. 4, 604-610 (2017).
Blanketjin, Peter, Sympathetic Hyperactivity in Chronic Kidney Disease, Neprhol Dial Transplant, vol. 19, No. 6, 1354-1357 (2004).
Blum et al., Treatment of Ostial Renal-Artery Stenoses with Vascular Endoprostheses after Unsuccessful Balloon Angioplasty, N. Engl. J. Med. 336 459-65 (1997).
Bonsignore, C., "A Decade of Evolution in Stent Design", Proceedings of the International Conference on Shape Memory and Superelastic Technologies, (2003).
Bradfield, Jason S. et al., Renal denervation as adjunctive therapy to cardiac sympathetic denervation for ablation refractory ventricular tachycardia, Heart Rhythm Society, vol. 17, No. 2, 220-227 (2020).
Bush, et al., "Endovascular revascularization of renal artery stenosis: Technical and clinical results", Journal of Vascular Surgery, May 2001, 1041-1049 (2001).
Camasao, D. B. et al., The mechanical characterization of blood vessels and their substitutes in the continuous quest for physiological-relevant performances: A critical review, Materials Today Bio, vol. 10 (2021).
Carter, Stefan et al., Measurement of Renal Artery Pressures by Catheterization in Patients with and without Renal Artery Stenosis, Circulation, vol. XXXIII, 443-449 (1966).
Chapelon, J.Y., "Treatment of Localised Prostate Cancer with Transrectal High Intensity Focused Ultrasound," European Journal of Ultrasound 9, 31-38, 1999.
Charlesworth, Peter et al., Renal Artery Injury from a Fogarty Balloon Catheter, Journal of Vascular Surgery, vol. 1, No. 4, 573-576 (1984).
Chart showing priority claims of the '629 patent, exhibit to Petition for Inter Partes Review of U.S. Pat. No. 8,845,629, filed Jan. 13, 2022 in the Patent Trial and Appeal Board, United States Patent and Trademark Office, Petition No. PTAB-IPR2022-00431.
Chiesa et al., Endovascular Stenting for the Nutcracker Phenomenon, J. Endovasc. Ther., 8:652-655 (2001).
Coates, Paul et al., "Time, Temperature, Power, and Impedance Considerations for Radiofrequency Catheter Renal Denervation," Cardiovascular Revascularization Medicine 42, 171-177 (2022).
Corrected Patent Owner's Response to Office Action, dated May 10, 2013, from File History of Inter Partes Reexamination 95/002,110.
Correspondence from PTAB Deputy Chief Clerk to Counsel re conference call request—Exhibit 3001 in the Patent Trial and Appeal Board, United States Patent and Trademark Office, Petition No. PTAB-IPR2022-00431.
Curriculum Vitae of Dr. Chris Daft.
Curriculum Vitae of Dr. John M. Moriarty.
Curriculum Vitae of Dr. Michael Bohm.
Curriculum Vitae of Farrell Mendelsohn.
Dangas, G., et al., Intravascular Ultrasound-Guided Renal Artery Stenting, J Endovasc Ther, 2001;8:238-247 (2001).
Deardorff, Dana et al., Ultrasound Applicators with Internal Water-Cooling for High-Powered Interstitial Thermal Therapy, IEEE Transactions on Biomedical Engineering, vol. 47, No. 10, 1356-1365 (2000).
Deardorff, Dana et al., Ultrasound Applicators with Internal Cooling for Interstitial Thermal Therapy, SPIE vol. 3594, 36-46, Jan. 1999.
Decision of the Patent Trial and Appeal Board in U.S. Appl. No. 14/731,347.

(56) References Cited

OTHER PUBLICATIONS

Declaration of Chris Daft dated Jan. 11, 2022, in the Patent Trial and Appeal Board, United States Patent and Trademark Office, Petition No. PTAB-IPR2022-00431.
Second Declaration of Chris Daft. Dated Jan. 10, 2023, in the Patent Trial and Appeal Board, United States Patent and Trademark Office, Petition No. PTAB-IPR2022-00431.
Declaration of Dr. Daniel van der Weide, dated Oct. 26, 2022, in the Patent Trial and Appeal Board, United States Patent and Trademark Office, Petition No. PTAB-IPR2022-00431.
Declaration of Dr. Dieter Haemmerich, dated Aug. 29, 2012, in the Patent Trial and Appeal Board, United States Patent and Trademark Office, In re U.S. Pat. No. 7,717,948.
Declaration of Dr. John M. Moriarty in German Nullity proceedings for EP2261905 dated Jul. 13, 2022.
Declaration of Dr. John Moriarty, dated Jan. 19, 2023, in the Patent Trial and Appeal Board, United States Patent and Trademark Office, Petition No. PTAB-IPR2022-00431.
Declaration of Jonathan Bradford in Support of Patent Owner's Response, dated Oct. 27, 2022.
Declaration of Jonathan Bradford dated May 10, 2022, in the Patent Trial and Appeal Board, United States Patent and Trademark Office, Petition No. PTAB-IPR2022-00431.
Declaration of Dr. Michael Bohm dated Sep. 29, 2022 on behalf of Medtronic Inc.
Declaration of Dr. Robert Tucker, dated Oct. 27, 2022, in the Patent Trial and Appeal Board, United States Patent and Trademark Office, Petition No. PTAB-IPR2022-00431.
Declaration of Farrell Mendelsohn dated Jan. 10, 2022, in the Patent Trial and Appeal Board, United States Patent and Trademark Office, Petition No. PTAB-IPR2022-00431.
Defendant's Reply to Court Order of Oct. 4, 2022 and Plaintiff's Surrejoinder of Sep. 29, 2022 in the Mannheim District Court, case No. 7 O 14/21, dated Oct. 31, 2022.
Defendant's Response dated May 11, 2022 in the Munich Federal Patent Court, Nullity Suit 6 Ni 32/22.
Dibona, Gerald F., "Neural Control of the Kidney, Past, Present and Future," 41 [Part II] Hypertension 621 24 (2003).
Dibona, Gerald, Sympathetic Nervous System and Kidney in Hypertension, Current Opinion in Nephrology and Hypertension, vol. 11, 197-200 (2002).
Dibona, Gerald F. et al., "Neural Control of Renal Function", 77 Physiological Reviews No. 1, 75 (1997).
Diederich, et al., "Catheter-based Ultrasound Applicators for Selective Thermal Ablation: progress towards MRI-guided applications in prostate," International Journal of Hyperthermia, 20:7, 739-756.
Diederich, et al., "Transurethral Ultrasound Applicators with Directional Heating Patterns for Prostate Thermal Therapy: In vivo evaluation using magnetic resonance thermometry," Med. Phys. 31 (2), 405-413, Feb. 2004.
Diederich, et al., Ultrasound Catheters for Circumferential Cardiac Ablation, in Proceedings of SPIE Conference on Thermal Treatment of Tissue with Image Guidance San Jose, California, Jan. 1999 SPIE vol. 3594.
Draney, Mary et al., Three-Dimensional Analysis of Renal Artery Bending Motion During Respiration, International Society of Endovascular Specialists, vol. 12, 380-386 (2005).
Erikson, Kenneth et al., Ultrasound in Medicine: A Review, IEEE Transactions on Sonics and Ultrasonics, vol. 21, No. 3 (1974).
EP Board of Appeals Communication dated Dec. 17, 2019— Preliminary Remarks for EP appeal No. T2680/16-3.3.4.01.
European Search Report in Application No. 12180431.4 dated Jan. 17, 2013.
European Communication in Application No. 12180431.4 dated Oct. 23, 2013.
European Office Action in Application No. 12180431.4.
European Patent No. 12167931, Claims of the Main Request dated Sep. 30, 2016.
European Search Report (Supplementary) in Application No. 14775754.6 dated Feb. 17, 2016.
European Search Report in Application No. 218186547 dated Nov. 19, 2018.
European Search Report in Application No. 20202272.9 dated Mar. 1, 2021.
Fan, Xiaobing et al., "Control of the Necrosed Tissue Volume during Noninvasive Ultrasound Surgery using a 16-Element Phased Array," Department of Radiology, Brigham and Women's Hospital, Harvard Medical School, Oct. 31, 1994.
Fengler, Karl et al., A Three-Arm Randomized Trial of Different Renal Denervation Devices and Techniques in Patients With Resistant Hypertension (Radiosound-HTN), 139 Circulation 590 (2019).
File History to EP1802370B1 Part 1.
File History to EP1802370B1 Part 2.
File History to EP1802370B1 Part 3.
Foley, Jessica L., et al., "Image-Guided HIFU Neurolysis of Peripheral Nerves to Treat Spasticity and Pain," Ultrasound in Med & Biol., vol. 30, Np. 9 pp. 1199-1207, 2004.
Gallitto, Enrico et al., Renal Artery Orientation Influences the Renal Outcome in Endovascular Thoraco-abdominal Aortic Aneurysm Repair, European Society of Endovascular Surgery, vol. 56, No. 3, 382-390 (2018).
Gervais, Debra A. et al., Radiofrequency ablation of renal cell carcinoma: Part 2, Lessons learned with ablation of 100 tumors, 185 AJR Am. J. Roentgenol. 72 (2005).
Goldberg, S. Nahum et al., EUS-guided radiofrequency ablation in the pancreas: results in a porcine model, 50 Gastrointest. Endosc. 392 (1999).
Golwyn et al., Percutaneous Transcatheter Renal Ablation with Absolute Ethanol for Uncontrolled Hypertension or Nephrotic Syndrome: Results in 11 Patients with End-Stage Renal Disease, J. Vasco and Interventional Radiology, 8,527-433 (1997).
Gorsich, W., et al., Heat-Induced Contraction of Blood Vessels, Lasers in Surgery and Medicine, 2:1-13 (1982).
Gray, Henry, Gray's Anatomy: The Anatomical Basis of Medicine and Surgery, Churchill Livingstone, New York, NY (1995).
Habict, Antje et al., Sympathetic Overactivity and Kidneys, The Middle European Journal of Medicine, vol. 115, 634-640 (2003).
Hansen et al., The Transplanted Human Kidney Does Not Achieve Functional Reinnervation, 87 Clinical Science 13 (1994).
He, D. S. et al., Application of Ultrasound Energy for Intracardiac Ablation of Arrhythmias, European Heart Journal, vol. 16, 961-966 (1995).
Holmes, David R. et al., Pulmonary vein stenosis complicating ablation for atrial fibrillation: clinical spectrum and interventional considerations, 2 JACC Cardiovasc. Interv. 267 (2009).
Hsu, Thomas H. S. et al., Radiofrequency ablation of the kidney: acute and chronic histology in porcine model, 56 Urology 872 (2000).
Huang, S.K.S. and Wilbur, D. Eds, Radiofrequency Catheter Ablation of Cardiac Arrhythmias, Basic Concepts and Clinical Applications, Futura Publishing Company, Inc., Armonk, New York (2000).
Huang, et al., Renal Denervation Prevents and Reverses Hyperinsulinemia-Induced Hypertension in Rats, Hypertension 32 (1998) pp. 249-254.
Institution Decision Granting Institution of Inter Partes Review 35 U.S.C. sec. 314, dated Aug. 8, 2022 in the Patent Trial and Appeal Board, United States Patent and Trademark Office, Petition No. PTAB-IPR2022-00431.
Isles et al., Management of Renovascular Disease: A Review of Renal Artery Stenting in Ten Studies, QJM 92, 159-67 (1999).
Janssen, B. J. A., et al. "Renal nerves in hypertension." Miner Electrolyte Metab., 15:74-82 (1989).
Janzen, Nicolette et al., Minimally Invasive Ablative Approaches in the Treatment of Renal Cell Carcinoma, Current Urology Reports, vol. 3 (2002).
Kaltenbach, Benjamin et al., Renal Artery Stenosis After Renal Sympathetic Denervation, Journal of the American College of Cardiology, vol. 60, No. 25 (2012).
Kapural, Leonardo, et al., "Radiofrequency Ablation for Chronic Pain Control," Anesthetic Techniques in Pain Management, pp. 517-525, 2001.

(56) References Cited

OTHER PUBLICATIONS

Katholi, R.E., et. al., Importance of Renal Sympathetic Tone in the Development of DOCA-Salt Hypertension in The Rat, Hypertension, 2:266-273 (1980).

Kim, Yun-Hyeon et al., Pulmonary vein diameter, cross-sectional area, and shape: CT analysis, Radiology Society of North America, vol. 235, No. 1, 49-50 (2005).

Kirsh, Danielle, Balloon Catheters: What are some key design considerations?, MassDevice (Dec. 6, 2016).

Kompanowska-Jezierska, Elzbieta et al., Early Effects of Renal Denervation in the Anaesthetized Rat: Natriuresis and Increased Cortical Blood Flow, 531 J. Physiology No. 2, 527 (2001).

Koomans, Hein et al., Sympathetic Hyperactivity in Chronic Renal Failure: A wake-up call, Frontiers in Nephrology, vol. 15, 524-537 (2004).

Kuo, et al., "Atrial Fibrillation: New Horizons", Chang Gung Med J vol. 26 No. 10 Oct. 2003.

Lang, Roberto et al., Recommendations for Chamber Quantification: A Report from the American Society of Echocardiography's Guidelines and Standards Committee and the Chamber Quantification Writing Group, Developed in Conjunction with the European Association of Echocardiography, a Branch of the European Society of Cardiology, Journal of the American Society of Echocardiography, vol. 18, No. 12, 1440-1463 (2005).

Lee, Jong Deok et al., MR imaging-histopathologic correlation of radiofrequency thermal ablation lesion in a rabbit liver model: observation during acute and chronic stages, 2 Korean J. Radiol. 151 (2001).

Levin, S., et al., Ardian: Succeeding Where Drugs Fail—Treating Hypertension in the Cath Lab, In Vivo, 27:23 (2009).

Mahfoud, Felix et al., Catheter-Based Renal Denervation Is No Simple Matter: Lessons to Be Learned From Our Anatomy?, Journal of the American College of Cardiology, vol. 64, No. 7, 644-647 (2014).

Marine, Joseph E., Catheter ablation therapy for supraventricular arrhythmias, 298 JAMA 2768 (2007).

Martin, Louis K. et al., Long-term Results of Angioplasty in 110 Patients with Renal Artery Stenosis, Journal of Vascular and Interventional Radiology, vol. 3, No. 4, 619-626 (1992).

Matsumoto, Edward D. et al., Short-term efficacy of temperature-based radiofrequency ablation of small renal tumors, 65 Urology 877 (2005).

Medtronic Press Release, Medtronic Announces U.S. Renal Denervation Pivotal Trial Fails to Meet Primary Efficacy Endpoint While Meeting Primary Safety Endpoint (Jan. 9, 2014).

Medtronic Inc., Renal Denervation (RDN): Novel Catheter-Based Treatment for Hypertension, Scientific Background, 2011.

Medtronic Scientific Background, Hypertension and the Symplicity Renal Denervation System.

Medtronic, Symplicity RDN Common System Q&A.

Medtronic Inc., The Symplicity RDN System, 2012.

Meyers, Philip et al., Temporary Endovascular Balloon Occlusion of the Internal Carotid Artery with a Nondetachable Silicone Balloon Catheter: Analysis Technique and Cost, American Journal of Neuroradiology, vol. 20, No. 4, 559-564 (1999).

Millard, et al., Renal Embolization for Ablation of Function In Renal Failure And Hypertension, Postgraduate Med. J. 65, 729-734 (1989).

Mitchell, et al., "The Renal Nerves" British Journal of Urology, Read by invitation at the Sixth Annual Meeting of the British Association of Urological Surgeons on Jun. 30, 1950.

Morrissey, D. M. "Sympathectomy in the treatment of hypertension." Lancet, CCLXIV:403-408 (1953).

Natale, Andrea et al., First Human Experience with Pulmonary Vein Isolation Using a Through-the-Balloon Circumferential Ultrasound Ablation System for Recurrent Atrial Fibrillation, Circulation, vol. 102, 1879-1882 (2000).

Netter, Frank, Atlas of Human Anatomy, Icon Learning Systems, Rochester, NY (2002).

Neumann, Jutta, Sympathetic hyperactivity in chronic kidney disease: Pathogenesis, clinical relevance, and treatment, International Society of Nephrology, vol. 65, 1568-1576 (2004).

News, Columbia University Irving Medical Center, Zapping Nerves with Ultrasound Lowers Drug-Resistant Blood Pressure (May 16, 2021), https://www.cuimc.columbia.edu/news/zapping-nervesultrasound-lowers-drug-resistant-blood-pressure.

Notice of Deposition of Tucker, filed Dec. 30, 2022 in the Patent Trial and Appeal Board, United States Patent and Trademark Office, Petition No. PTAB-IPR2022-00431.

Notice of Deposition of van der Weide, filed Dec. 30, 2022 in the Patent Trial and Appeal Board, United States Patent and Trademark Office, Petition No. PTAB-IPR2022-00431.

Notice re filing date accorded, dated Feb. 10, 2022 in the Patent Trial and Appeal Board, United States Patent and Trademark Office, Petition No. PTAB-IPR2022-00431.

Nozawa, T., et al. "Effects of long-term renal sympathetic denervation on heart failure after myocardial infarction in rats." Heart Vessels, 16:51-56 (2002).

Oliveira, Vera L. et al., "Renal Denervation Normalizes Pressure and Baroreceptor Reflex in High Renin Hypertension in Conscious Rats", 19 Hypertension Suppl. II No. 2, 17 (1992) ("Oliveira 1992").

Order: Conduct of the Proceeding Scheduling Order 37 C.F.R. sec. 42.5, dated Aug. 8, 2022 in the Patent Trial and Appeal Board, United States Patent and Trademark Office, Petition No. PTAB-IPR2022-00431.

Order Setting Oral Hearing 37 C.F.R. § 42.70, dated Mar. 24, 2023 in the Patent Trial and Appeal Board, United States Patent and Trademark Office, Petition No. PTAB-IPR2022-00431.

Page, Irvine H. & George J. Heuer, The Effect of Renal Denervation on the Level of Arterial Blood Pressure and Renal Function in Essential Hypertension, 14 J. Clinical Investigation 27 (1935) (received for publication in 1934).

Page, Irvine H. & George J. Heuer, The Effect of Renal Denervation on Patients Suffering from Nephritis, 14 J. Clinical Investigation 443 (1935) (received for publication in 1935).

Papademetriou, et al., "Renal Sympathetic Denervation: Hibernation or Resurrection?", Cardiology 2016; 135, 11 pgs.

Papadopoulos, N., "Evaluation of a Small Flat Rectangular Therapeutic Ultrasonic Transducer Intended for Intravascular Use," Ultrasonics 74, 196-203, 2017.

Pappone C, et al., "Circumferential radiofrequency ablation of pulmonary vein ostia: a new anatomic approach for curing atrial fibrillation", Circulation. 2000; 102(21): 2619-2628. (2000).

Patent Owner's Amended Objections to Evidence Under 37 C.F.R. §42.64.

Patent Owner's Mandatory Notice, filed Feb. 3, 2022 in the Patent Trial and Appeal Board, United States Patent and Trademark Office, Petition No. PTAB-IPR2022-00431.

Patent Owner's Notice of Deposition of Dr. Chris Daft, filed Sep. 20, 2022 in the Patent Trial and Appeal Board, United States Patent and Trademark Office, Petition No. PTAB-IPR2022-00431.

Patent Owner's Notice of Deposition of Dr. Chris Daft filed Feb. 21, 2023 in the Patent Trial and Appeal Board, United States Patent and Trademark Office, Petition No. PTAB-IPR2022-00431.

Patent Owner's Notice of Deposition of Dr. Farrell Mendelsohn, filed Sep. 21, 2022 in the Patent Trial and Appeal Board, United States Patent and Trademark Office, Petition No. PTAB-IPR2022-00431.

Patent Owner's Notice of Deposition of Dr. John Moriarty, filed Feb. 21, 2023 in the Patent Trial and Appeal Board, United States Patent and Trademark Office, Petition No. PTAB-IPR2022-00431.

Patent Owner's Objections to Evidence, filed Aug. 18, 2022 in the Patent Trial and Appeal Board, United States Patent and Trademark Office, Petition No. PTAB-IPR2022-00431.

Patent Owner's Power of Attorney, filed Feb. 3, 2022 in the Patent Trial and Appeal Board, United States Patent and Trademark Office, Petition No. PTAB-IPR2022-00431.

Patent Owner Medtronic Ireland Power of Attorney, filed May 10, 2022 in the Patent Trial and Appeal Board, United States Patent and Trademark Office, Petition No. PTAB-IPR2022-00431.

(56) References Cited

OTHER PUBLICATIONS

Patent Owner's Preliminary Response, filed May 10, 2022 in the Patent Trial and Appeal Board, United States Patent and Trademark Office, Petition No. PTAB-IPR2022-00431.
Patent Owner's Request for Oral Hearing, filed Mar. 23, 2023 in the Patent Trial and Appeal Board, United States Patent and Trademark Office, Petition No. PTAB-IPR2022-00431.
Patent Owner's Response, filed Oct. 27, 2022 in the Patent Trial and Appeal Board, United States Patent and Trademark Office, Petition No. PTAB-IPR2022-00431.
Patent Owner's Sur-Reply, filed Mar. 9, 2023 in the Patent Trial and Appeal Board, United States Patent and Trademark Office, Petition No. PTAB-IPR2022-00431.
Patent Owner's Updated Mandatory Notice, filed May 10, 2022 in the Patent Trial and Appeal Board, United States Patent and Trademark Office, Petition No. PTAB-IPR2022-00431.
Peet, M.M., Hypertension and Its Surgical Treatment by Bilateral Supradiaphragmatic Splanchnicectomy, Am. J. Surgery, LXXV:48-68 (1948).
Petition for Inter Partes Review of U.S. Pat. No. 8,845,629, dated Jan. 13, 2022 by ReCor Medical, Inc. and Otsuka Medical Devices Co., Ltd., in the Patent Trial and Appeal Board, United States Patent and Trademark Office, Petition No. PTAB-IPR2022-00431.
Petitioner ReCor's Biography of Dr. Neil C. Barman.
Petitioner's Power of Attorney for Otsuka Medical Devices Co., Ltd., filed Jan. 13, 2022 in the Patent Trial and Appeal Board, United States Patent and Trademark Office, Petition No. PTAB-IPR2022-00431.
Petitioner's Power of Attorney for Recor Medical, Inc., filed Jan. 13, 2022 in the Patent Trial and Appeal Board, United States Patent and Trademark Office, Petition No. PTAB-IPR2022-00431.
Petitioner Reply, filed Jan. 23, 2023 in the Patent Trial and Appeal Board, United States Patent and Trademark Office, Petition No. PTAB-IPR2022-00431.
Petitioners' Request for Oral Argument, filed Mar. 21, 2023 in the Patent Trial and Appeal Board, United States Patent and Trademark Office, Petition No. PTAB-IPR2022-00431.
Petitioners' Updated Mandatory Notices, dated Jan. 18, 2022 in the Patent Trial and Appeal Board, United States Patent and Trademark Office, Petition No. PTAB-IPR2022-00431.
Plaintiff's Nullity Brief, dated Jan. 14, 2022, in the Munich Federal Patent Court, Nullity Suit 6 Ni 32/22.
Plaintiff's Reply to the May 11, 2022 Response, dated Jul. 18, 2022, in the Munich Federal Patent Court, Nullity Suit 6 Ni 32/22.
Plaintiff's Response to Court Order disagreeing with Stay of Proceedings dated Oct. 28, 2022 in Mannheim District Court, Infringement suit 7 O 147/21.
Plaintiff's Technical Brief dated Sep. 29, 2022 in the Mannheim District Court, Infringement suit 7 O 147/21.
Plouin et al., Blood Pressure Outcome of Angioplasty in Atherosclerotic Renal Artery Stenosis: A Randomized Trial. Essai Multicentrique Medicaments vs Angioplastie (EMMA) Study Group, Hypertension 31, 823-29 (1998).
Prakash, Punit, et al., "Considerations for Theoretical Modeling of Thermal Ablation with Catheter-Based Ultrasonic Sources: Implications for Treatment Planning, Monitoring and Control," International Journal of Hyperthermia, 28:1, 69-86.
Prochnau, Dirk et al., Catheter-based renal denervation for drug-resistant hypertension by using a standard electrophysiology catheter, EuroIntervention, vol. 7, 1077-1080 (2012).
Pugsley, et al., The vascular system: An overview of structure and function, Journal of Pharmacological and Toxicological Methods 44 (2000) 333-340.
Pürerfellner, Helmut et al., Incidence, Management and Outcome in Significant Pulmonary Vein Stenosis Complicating Ablation for Atrial Fibrillation, 93 Am. J. Cardiol. 1428 (2004).
Pürerfellner, Helmut & Martinek, Martin, Pulmonary vein stenosis following catheter ablation of atrial fibrillation, 20 Curr. Opin. Cardiol. 484 (2005).
Reddy, Vivek Y., "Use of a Diode Laser Balloon Ablation Catheter to Generate Circumferential Pulmonary Venous Lesions in an Open-Thoracotomy Caprine Model," PACE, vol. 27, 52-57, Jan. 2004.
Romanes, G.J., Cunningham's Textbook of Anatomy (11th ed. 1972).
Ryan, Steve, What are the Risks Associated with a Pulmonary Vein Ablation Procedure?, Atrial Fibrillation: Resources for Patients (last accessed Oct. 18, 2022).
Ryan, Thomas et al., Proceedings of Thermal Treatment of Tissue with Image Guidance, Progress in Biomedical Optics, vol. 3594 (1999).
Ryan, Thomas P._ Thermal Treatment of Tissue with Image Guidance; Ultrasound Catheters For Circumferential Cardiac Ablation 1999.
Sakakura, Kenichi et al., Anatomic Assessment of Sympathetic Peri-Arterial Renal Nerves in Man, Journal of the American College of Cardiology, vol. 64, No. 7, 635-643 (2014).
Sánchez-Quintana, Damian et al., How close are the phrenic nerves to cardiac structures? Implications for cardiac interventionalists, 16 J. Cardiovasc. Electrophysiol 309 (2005) ("Sánchez-Quintana").
Sato, Yu, et al., "Translational Value of Preclinical Models for Renal Denervation: a histological comparison of human versus porcine renal nerve anatomy," EuroIntervention, 18, e1120-e1128, 2023.
Schmieder, Ronald E., Renal denervation in patients with chronic kidney disease: current evidence and future perspectives, Nephrol. Dial. Transplant. gfac189 (2022).
Schneider, Peter, Endovascular Skills: Guidewire and Catheter Skills for Endovascular Surgery, 2nd ed., Marcel Dekker, Inc., New York, NY (2003).
Schneider, Peter A., Endovascular Skills, Quality Medical Publishing, Inc., 1998 ("Schneider").
Schmidt, Boris, et al., "Pulmonary Vein Isolation by High Intensity Focused Ultrasound," Indian Pacing and Electrophysiology Journal, pp. 126-133 (2006).
Selected documents from the File History of Inter Partes Reexamination 95/002,110, exhibit to Petition for Inter Partes Review of U.S. Pat. No. 8,845,629, filed Jan. 13, 2022 in the Patent Trial and Appeal Board, United States Patent and Trademark Office, Petition No. PTAB-IPR2022-00431.
Shimizu, Kazumasa et al., Sympathetic Dysfunction in Heart Failure, Bailliere's Clinical Endocrinology and Metabolism, vol. 7, No. 2 (1993).
Shonai et al., Renal Artery Aneurysm: Evaluation with Color Doppler Ultrasonography Before and lifter Percutaneous Transarterial Embolization, J. Ultrasound Med. 19, 277-80 (2000)("Shonai 2000").
Slide deck from Medtronic Circulatory System Devices Panel Meeting, General Issues Panel: Clinical Evaluation of Anti-Hyperintensive Devices (Dec. 5, 2018).
Smithwick, R. H., et al., "Splanchnicectomy for essential hypertension." J. Am. Med. Assoc., 152:1501-1504 (1953).
Stella, A., et al. "Effects of reversible renal denervation on haemodynamic and excretory functions of the ipsilateral and contralateral kidney in the cat." J Hypertension, 4: 181-188 (1986)("Stella").
Stipulation Modifying Schedule, dated Dec. 30, 2022 in the Patent Trial and Appeal Board, United States Patent and Trademark Office, Petition No. PTAB-IPR2022-00431.
Stipulation Modifying Schedule, dated Feb. 16, 2023 in the Patent Trial and Appeal Board, United States Patent and Trademark Office, Petition No. PTAB-IPR2022-00431.
Stoeckel, D. et al., A Survey of Stent Designs, Min Invas Ther & Allied Technol 2002: 11(4) 137-147 (2002).
Swartz, John F. et al., Radiofrequency Endocardial Catheter Ablation of Accessory Atrioventricular Pathway Atrial Insertion Sites, 87 Circulation 487 (1993).
Tanaka, Kazushi et al., "A New Radiofrequency Thermal Balloon Catheter for Pulmonary Vein Isolation," Journal of the American College of Cardiology vol. 38, No. 7, 2001.
Teigen et al., Segmental Renal Artery Embolization for Treatment of Pediatric Renovascular Hypertension, J. Vasco Interv. Radiol. 3, 111-7 (1992).

(56) References Cited

OTHER PUBLICATIONS

Thatipelli, Mallik R., et al., CT angiography of renal artery anatomy for evaluating embolic protection devices, 18 J. Vasc. Interv. Radiol. 842 (2007).
The Doctors and Experts at WebMD, Webster's New World Medical Dictionary (3rd ed. 2008) ("WebsterMD").
Transcript of the Mar. 2, 2023 deposition of Dr. John Moriarty.
Transcript of the Mar. 3, 2023 deposition of Dr. Chris Daft.
Transcript of deposition of the Jan. 1, 2023 deposition of Dr. Robert Tucker.
Transcript of the Jan. 14, 2023 deposition of Dr. Daniel van der Weide.
Transcript of the Sep. 30, 2022 deposition of Dr. Chris Daft.
Transcript of the Oct. 1, 2022 deposition of Dr. Farrell Mendelsohn.
Tsao, Hsuan-Ming et al., Evaluation of Pulmonary Vein Stenosis after Catheter Ablation of Atrial Fibrillation, 6 Card. Electrophysiol. Rev. 397 (2002).
Turner, et al., "Initial Experience Using the Palmaz Corinthian Stent for Right Ventricular Outflow Obstruction in Infants and Small Children", Catheterization and Cardiovascular Interventions 51:444-449 (2000).
Uchida, et al., "Effect of radiofrequency catheter ablation on parasympathetic denervation: A comparison of three different ablation sites." PACE, 21 :2517- 2521 (1998).
Ulmsten, Ulf et al., "The Safety and Efficacy of Meno TreatTM, a new balloon device for thermal endometrial ablation," Acta Obstet Gynecol Scand 2001; 80: 52-57.
Vaezy, Shahram et al., Image-Guided Acoustic Therapy, Annual Review Biomedical Engineering, vol. 3, 375-390 (2001).
Valente, John F. et al., Laparoscopic renal denervation for intractable ADPKD-related pain, 16 Nephrol. Dial. Transplant. 160 (2001).
Vujaskovic, Z. et al., (1994) Effects of intraoperative hyperthermia on canine sciatic nerve: histopathologic and morphometric studies, International Journal of Hyperthermia, 10:6, 845-855 (1994) ("Vujaskovic 1994").
Wanchoo, Nishey, Medtronic Gets European and Australian Approval for Symplicity Spyral Multi-Electrode Renal Denervation Catheter, Medgadget (2013).
Weinstock, Marta et al., "Renal Denervation Prevents Sodium Retention and Hypertension in Salt-Sensitive Rabbits with Genetic Baroreflex Impairment", 90 Clinical Science 287 (1996).
Zazgornik, "Bilateral Nephrectomy: The best, but often overlooked, treatment for refractory hypertension in hemodialysis patients," Am. J. Hypertension, 11:1364-1370 (1998).
Ziegler et al., Sources of Urinary Catecholamines in Renal Denervated Transplant Recipients, 8 J. Hypertension No. 10, 927 (1990).
U.S. Appl. No. 17/453,636, filed Nov. 4, 2021, File History.
U.S. Appl. No. 10/408,665, File History.
U.S. Appl. No. 60/624,793, File History.
U.S. Appl. No. 60/370,190, File History.
U.S. Appl. No. 60/415,575, File History.
U.S. Appl. No. 60/442,970, File History.
U.S. Appl. No. 60/616,254, File History.
U.S. Appl. No. 60/747,137, File History.
U.S. Appl. No. 60/808,306, File History.
U.S. Appl. No. 60/816,999, File History.
U.S. Appl. No. 61/405,472.
U.S. Appl. No. 11/532,814, Non-Final Office Action mailed Mar. 29, 2012.
U.S. Appl. No. 14/683,966, PTO Response to Rule 312 Communication mailed Mar. 29, 2018, 2 pgs.
U.S. Appl. No. 14/683,966, Corrected Notice of Allowance mailed May 22, 2018, 4 pgs.
U.S. Appl. No. 15/204,349, Preliminary Amendment filed Nov. 30, 2016, 3 pgs.
U.S. Appl. No. 15/204,349, Response filed Jun. 24, 2019 to Final Office Action mailed Apr. 22, 2019, 12 pgs.
U.S. Appl. No. 15/261,732, Notice of Allowance dated Sep. 25, 2018.
U.S. Appl. No. 16/219,874, Final Office Action mailed Dec. 21, 2020, 7 pages.
U.S. Appl. No. 17/453,636, filed Nov. 4, 2021.
File History of U.S. Appl. No. 12/754,337.
File History to U.S. Pat. No. 9,943,666.
File History to U.S. Pat. No. 9,981, 108.
File History to U.S. Pat. No. 10,039,901.
Borchert, Bianca et al., "Lethal Atrioesophageal Fistual After Pulmonary Vein Isolation using High-Intensity Focused Ultrasound (HIFU)" J. Hrthm vol. 5, Issue 1, p. 145-148, Jan. 2008.
Calkins, Hugh et al., "Temperature Monitoring During Radiofrequency Catheter Ablation Procedures Using Closed Loop Control," Circulation vol. 90, No. 3, p. 1279-1286, Sep. 1994.
Deardorff, Dana L. et al., "Control of interstitial thermal coagulation: Comparative evaluation of microwave and ultrasound applicators," Medical Physics vol. 28, No. 1, p. 104-117, Jan. 2001.
Dinerman, Jay L. et al., "Temperature Monitoring During Radiofrequency Ablation," Journal of Cardiovascular Electrophysiology, vol. 7 No. 2, p. 163-173, Feb. 1996.
Esler, Murray et al., "The future of renal denervation," Autonomic Neuroscience: Basic and Clinical, vol. 204, p. 131-138, May 2017.
Filonenko, E.A. et al., "Heating of Biological Tissues by Two-Dimensional Phased Arrays with Random and Regular Element Distributions," Acoustical Physics, vol. 50 No. 2, p. 222-231, 2004.
Fry, William J., "Action of Ultrasound on Nerve Tissue—A review," The Journal of the Acoustical Society of America, vol. 25 No. 1, p. 1-5, Jan. 1953.
Fry, Frank J., "Precision High Intensity Focusing Ultrasonic Machines for Surgery," High Intensity Focused U.S., 152-156, Sep. 6-7, 1957.
Haines, David, "Biophysics of Ablation: Application to Technology," Journal of Cardiovascular Electrophysiology, vol. 15, No. 10, p. S2-S11, Oct. 2004.
Hynynen, K. et al., "Design of Ultrasonic Transducers for Local Hyperthermia," Ultrasound in Med. & Biol., vol. 7, No. 4, p. 397-402, Feb. 1981.
Hynynen, K. et al., "Temperature measurements during ultrasound hyperthermia," Medical Physics vol. 16, No. 4, p. 618-626, Jul./Aug. 1989.
Jolesz, Ferenc A. et al., "MR Imaging—Controlled Focused Ultrasound Ablation: A Noninvasive Image-Guided Surgery," Magnetic Resonance Imaging Clinics of North America, vol. 13, Issue 3, p. 545-560, 2005.
Kandzari, David A., et al., "Reply to letter to the editor by Kintur Sanghvi, MD; Allen McGrew, DO; and Kiran Hegde, BE, MBA," American Heart Journal, vol. 180, p. e3-e4, Oct. 2016.
Lafon, C. et al., "Design and Preliminary Results of an Ultrasound Applicator for Interstitial Thermal Coagulation," Ultrasound in Medicine & Biology, vol. 24, No. 1, p. 113-122, 1998.
Lewis, Matthew A. et al., "Thermometry and Ablation Monitoring with Ultrasound," Int. J. Hyperthermia vol. 31, Issue 2, p. 163-181, Mar. 2015.
Liu, Xinmeng et al., "Visualization and mapping of the right phrenic nerve by intracardiac echocardiography during atrial fibrillation ablation," Europace vol. 25, p. 1352-1360, 2023.
Mendelsohn, Farrell O., "Microanatomy of the Renal Sympathetic Nervous System," Endovascular Today, p. 59-62, Oct. 2013.
Okamura, Keisuke et al., "Intravascular Ultrasound Can Be Used to Locate Nerves, but not Confirm Ablation, During Renal Sympathetic Denervation," J. Clin. Med. Res., vol. 13, No. 12, p. 556-562, 2021.
Quadri, Syed A. et al., "High-intensity focused ultrasound: past, present, and future in neurosurgery," Neurosurgical Focus, vol. 44, No. 2, p. 1-9, Feb. 2018.
Ross, Anthony B. et al., "Highly directional transurethral ultrasound applicators with rotational control for MRI-guided prostatic thermal therapy," Physics in Medicine & Biology, vol. 49, p. 189-204, Jan. 2004.
Sakaoka, Atsushi, et al., "Accurate Depth of Radiofrequency-Induced Lesions in Renal Sympathetic Denervation Based on a Fine Histological Sectioning Approach in a Porcine Model," Cir. Cardiovasc. Interv., vol. 11, p. 1-8, 2018.
Sanghvi, Kintur et al., "Rationale and design for studies of renal denervation in the absence (Spyral HTN Off-Med) and presence

(56) References Cited

OTHER PUBLICATIONS (Spyral HTN On-Med) of antihypertensive medications," American Heart Journal, vol. 180, p. e1-e2. Oct. 2016.
Satou, Shunsuke et al., "Observation of renal sympathetic nerves by intravascular ultrasound," Hypertension Research vol. 42, p. 1092-1094, 2019.
Schmidt, Boris et al., "Balloon Catheters for Pulmonary Vein Isolation," Herz vol. 33, p. 580-584, 2008.
Smith, Nadine Barrie et al., "Transrectal Ultrasound Applicator for Prostate Heating Monitored Using MRI Thermometry," Int. J. Radiation Oncology Biol. Phys. vol. 43, No. 1, p. 217-225, 1998.
Stauffer, P.R. et al., "13 Interstitial Heating Technologies," Thermoradiotherapy and Thermochemotherapy, p. 279-320, 1995.
Swanson, David K. et al., "Tissue temperature Feedback Control of Power, The Key to Successful Ablation," Innovations, vol. 6 No. 4, p. 276-282, Jul./Aug. 2011.
Tabei, Makoto et al., "A k-space method for coupled first-order acoustic propagation equations," J. Acoust. Soc. Am., vol. 111, No. 1, pt. 1, p. 53-63, Jan. 2002.
Tzafriri, Abraham R. et al., "Innervation Patterns May Limit Response to Endovascular Renal Denervation," Journal of the American College of Cardiology, vol. 64, No. 11, p. 1079-1087, Sep. 2014.
Umemura, Shin-ichiro, "Focused ultrasound transducer for thermal treatment," International Journal of Hyperthermia, vol. 31, No. 2, p. 216-221, 2015.
Wan, Hong et al., "Thermal Dose Optimization for Ultrasound Tissue Ablation," IEE Transactions on Ultrasonics, Ferroelectrics, and Frequency Control, vol. 46, No. 4, p. 913-928, Jul. 1999.
Zivin, Adam, et al., "Temperature Monitoring versus Impedance Monitoring during RF Catheter Ablation," Radiofrequency Catheter Ablation of Cardiac Arrhythmias, Basic Concepts and Clinical Applications, Second Edition, Edited by Shoei K. Stephen Huang, MD & David J. Wilber, MD, p. 103-112, 2000.

\* cited by examiner

INTRALUMINAL MICRONEUROGRAPHY PROBES AND RELATED SYSTEMS AND METHODS

PRIORITY CLAIM

This application claims priority to U.S. Provisional Patent Application No. 63/110,920, titled "INTRALUMINAL MICRONEUROGRAPHY PROBES AND RELATED SYSTEMS AND METHODS by Shimada et al., filed Nov. 6, 2020, which incorporated by reference herein in its entirety.

This application is a continuation-in-part (CIP) of and claims priority to U.S. patent application Ser. No. 16/517, 180, filed on Jul. 19, 2019, which is a continuation of U.S. patent application Ser. No. 15/299,694, filed Oct. 21, 2016, which is a continuation of U.S. patent application Ser. No. 15/204,349, filed Jul. 7, 2016, which claims priority to U.S. Provisional Application No. 62/198,382, filed Jul. 29, 2015. This application is also a continuation-in-part (CIP) of and claims priority to U.S. patent application Ser. No. 15/943, 354, filed Apr. 2, 2018, which is continuation of U.S. patent application Ser. No. 14/683,966, filed Apr. 10, 2015, which claims priority to U.S. Provisional Patent Application No. 61/979,339, filed Apr. 14, 2014. Each of the applications recited above is incorporated herein by reference in its entirety.

FIELD

The invention relates generally to neural measurements, and more specifically to intraluminal microneurography probes that can be used to obtain neural measurements.

BACKGROUND

The human body's nervous system includes both the somatic nervous system that provides sense of the environment (vision, skin sensation, etc.) and regulation of the skeletal muscles, and is largely under voluntary control, and the autonomic nervous system, which serves mainly to regulate the activity of the internal organs and adapt them to the body's current needs, and which is largely not under voluntary control. The autonomic nervous system involves both afferent or sensory nerve fibers that can mechanically and chemically sense the state of an organ, and efferent fibers that convey the central nervous system's response (sometimes called a reflex arc) to the sensed state information. In some cases, the somatic nervous system is also influenced, such as to cause vomiting or coughing in response to a sensed condition.

Regulation of the human body's organs, can therefore be somewhat characterized and controlled by monitoring and affecting the nerve reflex arc that causes organ activity. The course of nerves associated with a specific organ generally follow the artery supplying the organ. The nerves are often distributed about the circumference of the vessel lumen and aligned with its longitudinal axis. For example, the renal nerves leading to a kidney can often cause a greater reflexive reaction than desired, contributing significantly to hypertension. Measurement of the nerve activity near the kidney, and subsequent ablation of some (but not all) of the nerve can therefore be used to control the nervous system's overstimulation of the kidney, improving operation of the kidney and the body as a whole.

Because proper operation of the nervous system is therefore an important part of proper organ function, it is desired to be able to monitor and change nervous system function in the human body to characterize and correct nervous system regulation of internal human organs.

New medical therapies have been practiced whereby a probe such as a needle, catheter, wire, etc. is inserted into the body to a specified anatomical location and destructive means are conveyed to nerves by means of the probe to irreversibly damage tissue in the nearby regions. The objective is to modulate (e.g., abolish) nerve function in the specified anatomic location. The result is that abnormally functioning physiological processes can be terminated or modulated back into a normal range. Unfortunately such medical therapies are not always successful because there is no means to assess that the nervous activity has been successfully abolished. An alternative objective can be to increase a physiologic process or modulate it to an abnormal range.

An example is renal nerve ablation to relieve hypertension. Various studies have confirmed the relationship of renal nerve activity with blood pressure regulation. In various renal ablation procedures, a catheter is introduced into a hypertensive patient's arterial vascular system and advanced into the renal artery. Renal nerves are located in the arterial wall and/or in regions adjacent to the artery. Destructive means are delivered proximate to the renal artery wall to an extent intended to cause destruction of nerve activity. Destructive means include energy such as RF, microwave, cryotherapy, ultrasound, laser or chemical agents. The objective is to abolish the renal nerve activity. Such nerve activity is an important factor in the creation and/or maintenance of hypertension and abolishment of the nerve activity reduces blood pressure and/or medication burden.

Unfortunately not all patients respond to this therapy. Renal nerve ablation procedures are often ineffective, potentially due to a poor probe/tissue interface. Accordingly, insufficient quantities of destructive means are delivered to the nerve fibers transmitting along the renal artery. One reason is that the delivery of destructive means to the arterial wall does not have a feedback mechanism to assess the destruction of the nerve activity. As a consequence an insufficient quantity of destructive means is delivered and nervous activity is not abolished. Clinicians therefore, require a means of improving the probe/tissue interface or better targeting of nerves, and a technology to monitor the integrity of the nerve fibers passing through the arterial wall in order to confirm destruction of nerve activity prior to terminating therapy. Current technology for the destruction of nerve activity does not provide practitioners with a feedback mechanism to detect when the desired nervous activity destruction is accomplished. Nerve destructive means are applied empirically without knowledge that the desired effect has been achieved.

It is known that ablation of the renal nerves, with sufficient energy, is able to effect a reduction in both systolic and diastolic blood pressure. Current methods are said to be, from an engineering perspective, open loop; i.e., the methods used to effect renal denervation do not employ any way of measuring, in an acute clinical setting, the results of applied ablation energies. It is only after application of such energies and a period of time (3-12 months) that the effects of the procedure are known.

The two major components of the autonomic nervous system (ANS) are the sympathetic and the parasympathetic nerves. The standard means for monitoring autonomic nerve activity is situations such as described is to insert very small electrodes into the nerve body or adjacent to it. The nerve activity creates an electrical field that the electrodes convert to an electrical voltage which is communicated to a monitoring means such that a clinician can assess nerve activity. This practice is called microneurography and its practical application is by inserting the electrodes transcutaneously to the desired anatomical location. This is not possible in the case of the ablation of many autonomic nerves proximate to arteries, such as the renal artery, because the arteries and nerves are located within the abdomen and cannot be accessed transcutaneously with any reliability. Thus the autonomic nerve activity cannot be assessed in a practical or efficacious manner.

The autonomic nervous system is responsible for regulating the physiological processes of circulation, digestion, metabolism, hormonal function, immune function, reproduction, and respiration among others. The sympathetic nerves and parasympathetic nerves most often accompany the blood vessels supplying the body organs which they regulate. Examples of such include but are not limited to the following: (1) Nerves regulating liver function accompany the hepatic artery and the portal vein; (2) Nerves regulating the stomach accompany the gastroduodenal, the right gastroepiploic artery, and the left gastric artery; (3) Nerves regulating the spleen accompany the splenic artery; (4) Nerves from the superior mesenteric plexus accompany the superior mesenteric artery, where both the artery and the nerves branch to the pancreas, small intestine, and large intestine; (5) Nerves of the inferior mesenteric plexus accompany the inferior mesenteric artery and branch with the artery to supply the large intestine, the colon, and the rectum; (6) Nerves accompanying the pulmonary artery that regulated the lungs and/or cardiac function; and (7) Greater splanchnic nerves regulating venous pooling.

When monitoring ANS activity, one must generally differentiate between the electrical signals generated by the ANS and those generated by muscle activity, which is commonly called electromyography (EMG) signals. EMG signals possess amplitudes several orders of magnitude larger than compared to those of the ANS. Probes possessing electrodes have been used to assess the EMG of the heart, stomach, intestines, and other muscles of the body. Such probes and their means and methods for detecting and analyzing the electric signals are not suitable for use with signals generated by the ANS.

Deficiencies in the use of existing therapeutic protocols in denervation of autonomic nerves proximate arteries include: 1) The inability to determine the appropriate lesion sites along the artery that correspond to the location of nerves; 2) The inability to verify that the destructive devices are appropriately positioned adjacent to the arterial wall, normalizing the tissue/device interface and enabling energy transfer through the vessel wall; and 3) Inability to provide feedback to the clinician intraoperatively to describe lesion completeness or the integrity of the affected nerve fibers. As a consequence, current autonomic nerve ablation procedures are performed in a 'blind' fashion; the clinician performing the procedure does not know where the nerves are located; and further, whether the nerves have truly been ablated. Instead, surrogates such as calf muscle sympathetic activity (MSNA) or catecholamine spillover into the circulating blood have been used to attempt to evaluate the reduction in organ specific autonomic activity such as renal nerve activity. It is entirely likely that this deficiency could at least partly be responsible for the current variability in clinical responses coming from clinical trials. Therefore, a system designed to indicate with precision, and in real time, whether ablation was successful is urgently needed.

SUMMARY

One example embodiment of the invention comprises an intraluminal microneurography probe, having a probe body that is substantially cylindrical and that is configured to be introduced into an artery near an organ of a body without preventing the flow of blood through the artery. An expandable sense electrode is fixed to the probe body at one end of the sense electrode and is movable relative to the probe body at a second end of the sense electrode such that movement of the movable end toward the fixed end causes the sense electrode to expand from the probe body toward a wall of the artery, and an expandable stimulation electrode is fixed to the probe body at one end of the stimulation electrode and movable relative to the probe body at a second end of the stimulation electrode such that movement of the movable end toward the fixed end causes the sense electrode to expand from the probe body toward a wall of the artery. An ablation element is configured to ablate nerve tissue in the vicinity of the expandable sense and stimulation electrodes. A ground electrode is configured to couple to the body, and a plurality of electrical connections are operable to electrically couple at least the expandable sense electrode, expandable stimulation electrode, ground electrode, and radio frequency ablation element to electrical circuitry.

In further examples, the ablation element (e.g., a radio frequency ablation element) comprises one or more monopole, dipole, loop, or ring antennas, or a phase-steered array of antennas. In further examples, the probe further comprises at least one of a cooling element configured to cool the probe in the vicinity of the radio frequency ablation element, and a reflector or shield configured to direct energy from the radio frequency ablation element in a specific direction.

In another example nerve activity associated with a body organ is characterized by introduction of a probe into artery to a location proximate to the body organ, and expansion of an expandable sense electrode and an expandable stimulation electrode comprising a part of the probe to contact the artery wall. An electricity source coupled to the stimulation electrode is used to excite the stimulation electrode (i.e., cause an evoked neural response), and the expanded sense electrode is used to measure the evoked neural response as a result of exciting the stimulation electrode. Additionally or alternatively, the sense electrode can be used to sense intrinsic nerve activity (e.g., in the absence of providing electrical stimulation to evoke a neural action potential). An ablation element is used to ablate nerves in the vicinity of the location proximate to the body organ such as via a radio frequency or other type of ablation element comprising a part of the probe, and re-excitation of the stimulation electrode using an electricity source coupled to the stimulation electrode, and re-measurement of the evoked neural response as a result of exciting the stimulation electrode using the expanded sense electrode are performed to confirm the effects of the ablation. Various other types of ablation elements can alternatively be used, as described herein. In certain embodiments the expandable sense electrode and the expandable stimulation electrode are designed to permit blood flow while they are expanded within an artery. In other embodiments, the expandable sense electrode and the expandable stimulation electrode are designed to inhibit blood flow while they are expanded within an artery.

Certain aspects of the disclosure are generally toward systems and methods for interfacing with the autonomic nervous system of a patient via an interior wall of a blood vessel, in other words, from within the lumen of a blood vessel. In some embodiments, a system includes a probe having at least one electrode capable of detecting electrical signals from an interior wall of a blood vessel. The system can include an electrical control unit (ECU) in electrical communication with the probe and capable of receiving an electrical signal from the at least one electrode of the probe. The ECU can process the received signal to produce an output signal, and present information including information about the output signal, the received signal, or processed information. Such systems can be used, for example, in diagnostic procedures for assessing the status of a patient's nervous activity proximate the blood vessel.

In some examples, the system can include a stimulation electrode for providing an electrical stimulus into the interior wall of the blood vessel. The electrical stimulus can be sufficient to provoke an elicited potential in the patient's nerves. The system can receive and process a signal including the elicited potential. Embodiments of the system can further perform a nerve destruction process to destroy nervous tissue or function proximate the blood vessel. The system can evoke and detect elicited potentials before and after the nerve destruction process and compare the detected potentials to determine the effective amount of destruction that has taken place.

In further examples, nerve destruction processes can be performed after at least one diagnostic procedure. For example, a diagnostic procedure can be performed to determine the level of nervous activity in nerves proximate a patient's blood vessel. The level of activity can be analyzed to determine whether or not a nerve destruction process is likely to be effective therapy for a patient. If so, nerve destruction processes can be performed. The level can also be analyzed during a procedure to ascertain if sufficient nerve destruction has happened or if additional nerve destruction is warranted.

Certain embodiments of the present technology are related to a system for use in analyzing neural activity of nerves that surround a biological lumen near an organ of a body. In certain embodiments the system includes a probe body configured to be introduced into the biological lumen near the organ of the body without preventing flow of blood through the biological lumen. A plurality of electrodes are supported by the probe body and electrically isolated from one another. A stimulator is electrically coupled to and configured to deliver electrical stimulation via a first pair of the electrodes to test for an evoked neural response, to the electrical stimulation, by the nerves that surround the biological lumen. The spacing between the pair of electrodes, at least in part, the extent of the electrical field produced by the stimulation. In certain embodiments, the spacing should be equal to or greater than the radial distance to the farthest nerve of interest. Furthermore, the spacing should be limited such that nerves which are not of interest will not be stimulated. An amplifier is configured to produce a sensed signal indicative of the evoked neural response, to the electrical stimulation, by the nerves that surround the biological lumen. The amplifier includes a pair of input terminals, an output terminal, and a ground reference terminal. A second pair of the electrodes is electrically coupled to the pair of input terminals of the amplifier, to thereby enable the amplifier to produce the sensed signal indicative of the evoked neural response, to the electrical stimulation, by nerves that surround the biological lumen, wherein at least one of the electrodes included in the second pair of the electrodes is not included in the first pair of the electrodes. In certain embodiments, neither of the electrodes included in the second pair of the electrodes is included in the first pair of the electrodes. In accordance with certain embodiments, the spacing between the electrodes coupled to the to the input terminals of the amplifier is equal to or greater than the radial distance to the furthest nerve of interest, but not to the extent that electrical fields generated away from the nerves of interest are also detected. The electrical field strength decreases by a quadratic factor of radial distance from the source of the electrical field, Thus increasing the spacing between electrodes does not produce a commensurate risk of detecting an electrical field from outside the region of the nerves of interest. A remaining one of the electrodes, which is not included in the first and the second pairs of the electrodes, is electrically coupled to the ground reference terminal of the amplifier.

In accordance with certain embodiments, the probe body includes a distal end and a proximal end, with the distal end being configured to be placed closer to the organ than the proximal end. The plurality of electrodes include electrodes E1, E2, E3, E4, and E5. The first pair of the electrodes, which is electrically coupled to the stimulator, comprises the electrodes E1 and E2. The second pair of the electrodes, which is electrically coupled to the pair of input terminals of the amplifier, comprises the electrodes E3 and E5. The remaining one of the electrodes, which is electrically coupled to the reference ground terminal of the amplifier, comprises the electrode E4.

In accordance with certain embodiments, each of the electrodes E2 and E3 comprises a deployable electrode that can be selectively transitioned between a non-deployed position and a deployed position. When such a deployable electrode is in the deployed position, at least a portion of the deployable electrode extends away from the probe body such that an outer circumference of the deployable electrode in the deployed position contacts an inner circumference of the biological lumen in which the probe body is introduced. In accordance with certain embodiments each deployable electrode is connected to one electrical lead, thus acting a single electrode. This single electrode provides substantially 360° coverage of the lumen circumference. As all the nerves essentially run parallel to the axis of the lumen, the deployed electrode can sense all of the nerve activity traveling between the organ of interest and the Central Nervous System. In this manner a decrease in or abolishment of nerve activity associated between the organ and the Central Nervous System can be determined.

In accordance with certain embodiments, an axial distance between the electrodes E1 and E2 is within a range of 1 cm to 6 cm, inclusive (which distance should be selected such that an electrical field strength of the stimulus is sufficient to evoke a neural response in nerves that surround the biological lumen); an axial distance between the electrodes E2 and E3 is within a range of 1 cm to 10 cm, inclusive, when the electrode E3 is in the deployed position (which distance should be selected such that the evoked action potential of the neural response do not reach the electrode E3 until any stimulus artifact effect has subsided); an axial distance between the electrodes E3 and E4 is within a range of 0.25 cm to 2.5 cm, inclusive, when the electrode E4 is in the deployed position (which distance should be selected such that it is at least as great a distance from the contact of the electrode with the lumen wall and to the nerve of interest furthest from the lumen wall); and an axial distance between the electrodes E4 and E5 is within a range of 0.25 cm to 2.5 cm, inclusive.

In accordance with certain embodiments, at least one of the deployable electrodes E2 and E3 comprises a deployable helical electrode.

In accordance with certain embodiments, at least one of the deployable electrodes E2 and E3 comprises a deployable mesh electrode made from a respective plurality of wires that are braided together and electrically connected to one another. Alternatively, the deployable electrodes E2 and/or E3 can be deployable basket electrodes, but are not limited thereto. The aforementioned deployable electrodes can be made from one or more wires, or can be made from an electrically conductive tube (e.g., made of nitinol, or some other alloy or metal) having a laser cut pattern. Other variations are also possible and within the scope of the embodiments describe herein.

In accordance with certain embodiments, a portion of such a deployable electrode, which portion does not contact the biological lumen when the deployable electrode is in the deployed position, is coated with an electrical insulator in order to provide one or more benefits such as: (a) reduced capacitance associated with the deployable electrode compared to if the portion was not coated with the electrical insulator; (b) reduced electrical field variability, making nerve capture more reliable, and (c) reduction of the electrical stimulus current that is necessary to stimulate the nerves of interest. More generally, in accordance with certain embodiments a portion of at least one of the deployable electrodes, which portion does not contact the biological lumen when the deployable electrode is in the deployed position, is electrically insulated. For example, a laterally outward facing peripheral portion of a unitary deployable electrode can be uninsulated, so as to permit electrical contact with surrounding biological tissue of the lumen in which the deployable electrode is exposed. When so deployed, an opposing laterally inward facing portion of the unitary deployable electrode can be electrically insulated, such as to help obtain one or more of the benefits described above. Further, other portions of the deployed electrode that do not make contact with the surrounding biological tissue of the lumen (e.g., such as portions of a supporting mesh that are located within the lumen in contact with blood flowing through the lumen, but not in contact with the lumen wall itself) can also be electrically insulated. In an example, the uninsulated laterally outward facing peripheral portion of a unitary deployable electrode can be arranged to permit circumferentially or semi-circumferentially or helically or otherwise peripherally contiguous electrical contact with surrounding biological tissue of the lumen in which the deployable electrode is exposed, such as preferably around an entire 360 degree circumference of the inner lumen wall, or at least around substantial portion thereof (e.g., with the cumulative intraluminal electrical contact length constituting at least 245 degrees of the 360 degree circumference of the inner lumen wall). Such a circumferentially, semi-circumferentially, or helically or otherwise peripherally contiguous intraluminal electrical contact can help provide better sensing of evoked or intrinsic neural signals from the nerves surrounding the lumen of the blood vessel.

In another example, the exposed electrical contact with surrounding biological tissue of the lumen can include gaps in the exposed electrical contact region, but with a cumulative intraluminal electrical contact length extending substantially around an entire 360 degree circumference of the inner lumen wall, or at least around substantial portion thereof (e.g., with the cumulative intraluminal electrical contact length constituting at least 245 degrees of the 360 degree circumference of the inner lumen wall). Delivery of electrical stimulus and sensing of either or both of intrinsic neural activity and evoked neural activity can be further improved by combining this aspect with electrically insulating portions of the unitary electrode that do not contact the inner lumen wall when the electrode is deployed such that portions of it contact the inner lumen wall.

In accordance with certain embodiments, a deployable electrode includes a plurality of openings through which blood can flow when the deployable electrode is in the deployed position, wherein a least some openings in a first portion of the deployable electrode, which first portion does not contact the biological lumen in which the probe body is introduced when the deployable mesh electrode is in the deployed position, are at least twice as large as all openings in a second portion of the deployable electrode, which second portion contacts the biological lumen in which the probe body is introduced when the deployable electrode is in the deployed position.

In accordance with certain embodiments, the electrodes E1, E2, E3, E4, and E5 are axially spaced apart from one another in that order, with the electrode E1 being a one of the electrodes at or closest to the distal end of the probe body, and the electrode E5 being a one of the electrodes at or closest to the proximal end of the probe body. In accordance with alternative embodiments, the electrodes E1, E2, E3, E4, and E5 are axially spaced apart from one another in that order, with the electrode E5 being a one of the electrodes at or closest to the distal end of the probe body, and the electrode E1 being a one of the electrodes at or closest to the proximal end of the probe body.

In accordance with specific embodiments, a system for use in analyzing neural activity of nerves that surround a biological lumen, comprises a probe body, a plurality electrodes, a stimulator, and an amplifier, wherein the plurality of electrodes includes electrodes E1, E2, E3, E4, E5, E6, and E7 electrically isolated from one another, with at least the electrodes E1, E2, E3, E5, E6, and E7 are supported by the probe body and axially spaced apart from one another in that order. The stimulator is electrically coupled to and configured to deliver electrical stimulation via a selected two of the electrodes to test for an evoked neural response, to the electrical stimulation, by the nerves that surround the biological lumen. The amplifier is configured to produce a sensed signal indicative of the evoked neural response, to the electrical stimulation, by the nerves that surround the biological lumen. The amplifier includes first and second input terminals, an output terminal, and a ground reference terminal. First switches enable a selection between connecting the electrodes E1 and E3 to the stimulator when the first switches are in a first configuration, and connecting the electrodes E7 and E5 to the stimulator when the first switches are in a second configuration. Second switches enable a selection between connecting the electrodes E5 and E6 to the first and second input terminals of the amplifier when the second switches are in a first configuration, and connecting the electrodes E3 and E2 to the amplifier when the second switches are in a second configuration. The electrode E4 is electrically coupled to the ground reference terminal of the amplifier. In one embodiment the electrode E4 comprises a non-implantable skin electrode. In another embodiment, the electrode E4 is supported by the probe body. In one such embodiment, the electrode E4, that is supported by the probe body, is located between the electrodes E3 and E5. In certain embodiments, each of the electrodes E3 and E5 comprises a deployable electrode that can be selectively transitioned between a non-deployed position and a deployed position. When such a deployable electrode is in the deployed position, at least a portion of the deployable electrode extends away from the probe body such that an outer circumference of the deployable electrode in the deployed position contacts an inner circumference of the biological lumen in which the probe body is introduced. In certain embodiments, the first switches and the second switches are configured to simultaneously be in their respective first configurations and to simultaneously be in the respective second configurations.

In accordance with certain embodiments, at least one of the electrodes of the second pair of electrodes comprises a deployable unitary electrode that can be selectively transitioned between a non-deployed position and a deployed position and is configured as a sense electrode to sense neural activity by the nerves that surround the biological lumen. In accordance with certain embodiments, the deployable unitary electrode, that is configured to be used as the sense electrode, has an outer periphery that simultaneously contacts multiple contiguous and/or non-contiguous locations, spaced about a 360 degree segment of an inner wall of the biological lumen, when the deployable unitary electrode is in its deployed position. In certain such embodiments, where the outer periphery simultaneously contacts multiple non-contiguous locations, the deployable unitary electrode, that is configured to be used as the sense electrode, is configured such that there are gaps of no more than 30 degrees between where the outer periphery of the deployable unitary electrode contacts multiple non-contiguous locations about a 360 degree segment of an inner wall of the biological lumen. In accordance with certain embodiments, the deployable unitary electrode, that is configured to be used as the sense electrode, is configured to cumulatively contact at least 245 degrees of a 360 degree segment of an inner wall of the biological lumen, when the deployable unitary electrode is in its deployed position.

In accordance with certain embodiments, an entire electrically conductive portion of the deployable unitary electrode, that is configured to be used as the sense electrode, is electrically connected to a same one of the terminals of the amplifier configured to produce the sensed signal. In certain such embodiments, the entire electrically conductive portion of the deployable unitary electrode, that is configured to be used as the sense electrode, is electrically connected to the same one of the terminals of the amplifier via a single electrically conductive wire that extends through a channel or lumen within the probe body that supports the deployable unitary electrode. In accordance with alternative embodiments, a pair or some other number of multiple wires can be used to electrically connect the entire electrically conductive portion of the deployable unitary electrode, that is configured to be used as the sense electrode, to the same one of the terminals of the amplifier. For example, such a pair of wires can be parallel to one another.

In accordance with certain embodiments, a system includes a probe body configured to be introduced into a renal artery, wherein the probe body includes a distal end and a proximal end, with the distal end being configured to be placed closer to a kidney than the proximal end. The system also includes a plurality of electrodes supported by the probe body and electrically isolated from one another. A stimulator is electrically coupled to and configured to deliver electrical stimulation via a first pair of the electrodes to evoke neural activity by the nerves that surround the biological lumen. An amplifier is configured to produce a sensed signal indicative of evoked neural activity and/or indicative of intrinsic neural activity by renal nerves that surround the renal artery. The amplifier includes a pair of input terminals, an output terminal, and a ground reference terminal. A second pair of the electrodes is electrically coupled to the pair of input terminals of the amplifier to thereby enable the amplifier to produce the sensed signal indicative of the evoked and/or intrinsic neural activity by the renal artery nerves. A fifth electrode electrically is coupled to the reference ground terminal of the amplifier. One of the first pair of electrodes comprises a first unitary mesh electrode configured to simultaneously contact multiple non-contiguous locations spaced about a 360 degree segment of an inner wall of the renal artery. One of the second pair of electrodes comprises a second mesh unitary electrode configured to substantially simultaneously contact multiple non-contiguous locations spaced about a second 360 degree segment of an inner wall of the renal artery. In certain such embodiments, the fifth electrode, which is electrically coupled to the reference ground terminal of the amplifier, is also supported by the probe body. Alternatively, the fifth electrode, which is electrically coupled to the reference ground terminal of the amplifier, comprises a non-implantable skin electrode. In certain such embodiments, the second mesh unitary electrode is configured to cumulatively contact at least 245 degrees of the second 360 degree segment of the inner wall of the renal artery.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE FIGURES

The details of one or more examples of the invention are set forth in the accompanying drawings and the description below. Other features and advantages will be apparent from the description and drawings, and from the claims.

FIG. 10A is a plot showing a stimulus signal and a detected elicited response before performing a destructive operation on the arterial nerves, FIG. 10B illustrates a stimulus signal and a detected elicited response, and FIG. 10C illustrates a stimulus signal and a detected elicited response after still more arterial nerve destruction has been performed.

DETAILED DESCRIPTION

Figure 1:
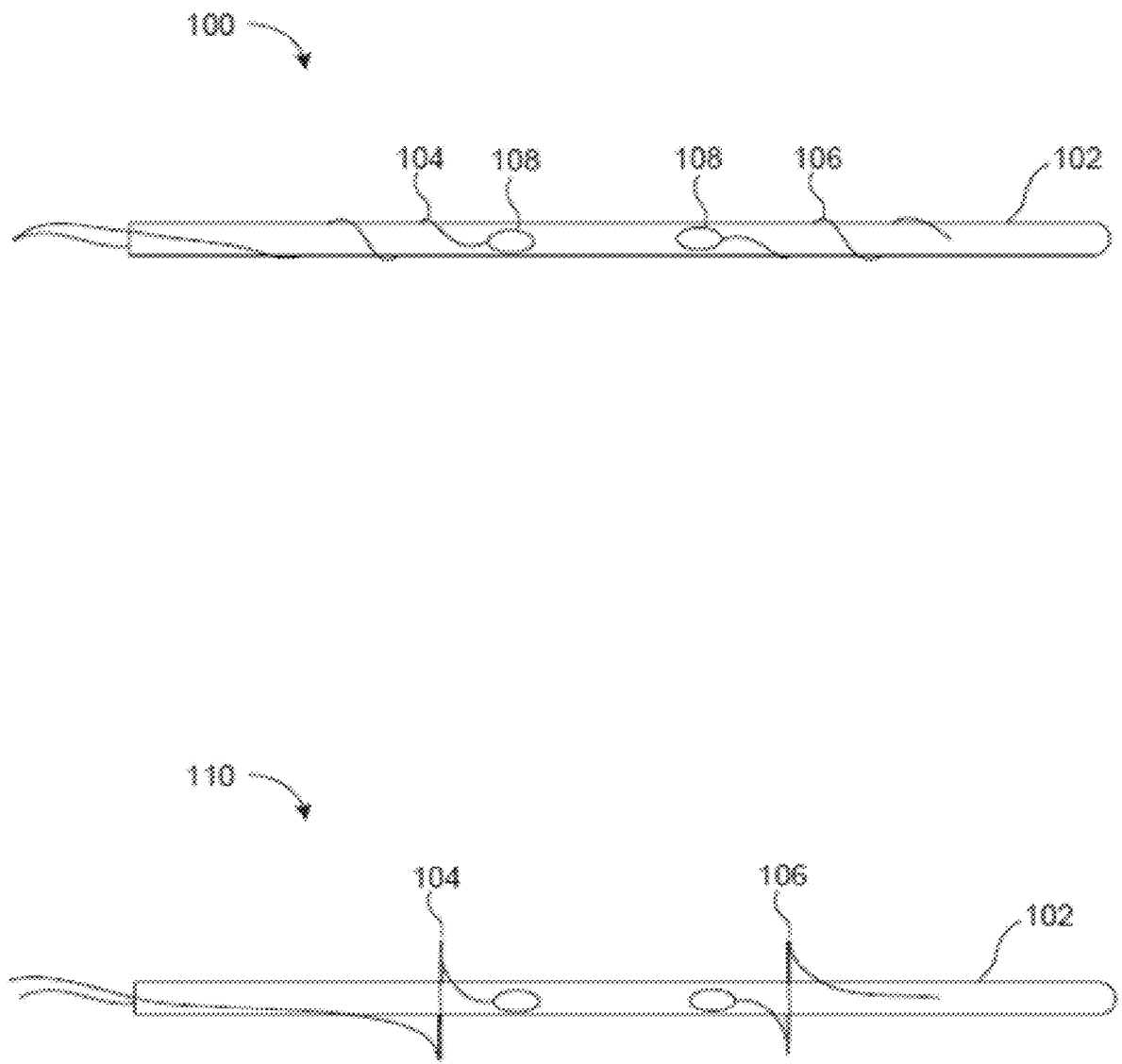
FIG. 1 illustrates an intraluminal microneurography probe having expandable helical wire electrodes, consistent with an example.

In the following detailed description of example embodiments, reference is made to specific example embodiments by way of drawings and illustrations. These examples are described in sufficient detail to enable those skilled in the art to practice what is described, and serve to illustrate how elements of these examples may be applied to various purposes or embodiments. Other embodiments exist, and logical, mechanical, electrical, and other changes may be made. Features or limitations of various embodiments described herein, however important to the example embodiments in which they are incorporated, do not limit other embodiments, and any reference to the elements, operation, and application of the examples serve only to define these example embodiments. Features or elements shown in various examples described herein can be combined in ways other than shown in the examples, and any such combination is explicitly contemplated to be within the scope of the examples presented here. The following detailed description does not, therefore, limit the scope of what is claimed.

Regulating operation of the nervous system to characterize nerve signaling and modulate organ function includes in some examples introduction of a probe such as a needle, catheter, wire, or the like into the body to a specified anatomical location, and partially destroying or ablating nerves using the probe to destroy nerve tissue in the region near the probe. By reducing nerve function in the selected location, an abnormally functioning physiological process can often be regulated back into a normal range. It would also be possible to modulate nerve function to purposely cause an abnormally functioning that is beneficial to the patient.

Unfortunately, it is typically very difficult to estimate the degree to which nerve activity has been reduced, which makes it difficult to perform a procedure where it is desired to ablate all nerves, or to ablate some, but not all, nerves to bring the nervous system response back into a desired range without destroying the nervous system response entirely.

One such example is renal nerve ablation to treat hypertension. Various studies have confirmed that renal nerve activity has been associated with hypertension, and that ablation of the nerve can improve renal function and reduce hypertension. In a typical procedure, a catheter is introduced into a hypertensive patient's arterial vascular system and advanced into the renal artery. Renal nerves located in the arterial wall and in regions adjacent to the artery are ablated by destructive means such as radio frequency waves, microwave, cryotherapy, ultrasound, laser or chemical agents to limit the renal nerve activity, thereby reducing hypertension in the patient.

Unfortunately, renal nerve ablation procedures are sometimes ineffective, such as due to either insufficiently ablating the nerve or destroying more nerve tissue than is desired. Also, it may be desirable to avoid ablating other off-target tissues. Clinicians often estimate based on provided guideline estimates or past experience the degree to which application of a particular ablative method will reduce nerve activity, and it can take a significant period of time (e.g., 3-12 months) before the clinical effects of the ablation procedure are fully known.

Some attempt has been made to monitor nerve activity in such procedures by inserting very small electrodes into or adjacent to the nerve body, which are then used to electrically monitor the nerve activity. Such microneurography practices are not practical in the case of renal ablation because the renal arteries and nerves are located within the abdomen and cannot be readily accessed, making monitoring and characterization of nerve activity in a renal nerve ablation procedure a challenge.

Prior methods such as inserting electrodes into the arteries of a patient's heart and analyzing received electrical signals are not readily adaptable to renal procedures. In the heart, the ablated tissue is heart muscle which itself is electrically conductive. Further, the cardiac muscle electrical signals are generally large and of longer duration relative to neural electrical signals near the renal arteries, which tend to be smaller in size and produce smaller signals that propagate more quickly through the nerves. In the case of renal denervation, the target of the ablation is renal nerves which lie outside the lumen of the blood vessel, with the objective to effectively terminate the neural communication between the kidneys and the Central Nervous System. The primary objective of cardiac ablation is to terminate select cardiac muscle activation pathways in order to eliminate harmful cardiac muscle rhythms. As such, intracardiac techniques used in heart measurements are not readily adaptable to similar renal procedures.

Because nerve activity during procedures to ablate or neuromodulate enervation of organs such as renal nerve ablation cannot be readily measured, it is also difficult to ensure that an ablation probe is located at the most appropriate sites along the renal artery, or to measure the efficiency of the nerve ablation process in a particular patient.

Some examples presented herein therefore provide an improved probe and method for characterizing nerve activity near an organ such as a kidney, including electrodes configured specifically to measure nerve activity in an environment different from the heart. In a more detailed example, the probe includes a sense electrode and a stimulation electrode that are expandable from a body of the probe, which can be introduced via a sheath. The sheath in a further embodiment comprises one or more electrodes, such as one or more sense electrodes, reference electrodes, or ground electrodes.

FIG. 1 illustrates an example of such a probe. Here, a probe assembly is shown generally at 100, including probe body 102, and first and second helical electrodes 104 and 106 that are not yet deployed. Accordingly, the helical electrodes 104 and 106 can be said to be in the non-deployed positions. Each of the helical electrodes is attached to the probe body at one end, shown here as an attachment point 108, such as an epoxy bead or other suitable attachment mechanism. The opposite end of each of the helical electrodes is constrained in the example shown, such as by emerging through a hole in the probe as shown by helical electrode 106, and extends from the left end of the probe assembly to connect to electronic instrumentation to perform various functions. The configuration of the helical electrode wires is such that the wires will expand about the axis of the probe body 102 when the wire of each helical electrode is forced toward the attachment points 108, causing the wire to form a circular shape having a diameter substantially larger than the helical electrode wires in the collapsed position, as shown at 100. When the helical electrodes 104 and 106 are in their non-deployed positions, they can conform to or remain close to the outer surface of the probe body 102, e.g., as shown in FIG. 1. In an alternative embodiment, the helical electrodes 104 and 106 are retained within one or more inner cavities of the probe body 102 when they are in their non-deployed positions.

The probe assembly is shown again at 110, here with the helical electrode wires 104 and 106 forced toward the attachment points 108, causing the wire to expand away from the probe body 102. In other words, in the probe assembly shown at 110 the first and second helical electrodes 104 and 106 have been deployed. Accordingly, at 110 the helical electrodes 104 and 106 can be said to be in their deployed positions, where they expand away from the probe body 102. This helical expansion allows the helical electrodes to expand in an environment such as an artery such as to contact the artery walls while allowing blood to flow around the probe body 102 and past the helical electrodes 104 and 106. When the probe 102 is inserted into an artery or other vasculature, it is the distal end of the probe that is initially inserted into the artery or other vasculature, and the proximal end of the probe 102 that is used to maneuver the probe 102. In the embodiment shown in FIG. 1, the electrode 106 can also be referred to as a distal electrode 106, since it located closer to the distal end of the probe 102 than to the proximal end of the probe 102; and the electrode 104 can also be referred to as a proximal electrode 104 since it is located closer to the proximal end of the probe 102 than to the distal end of the probe 102.

Figure 2:
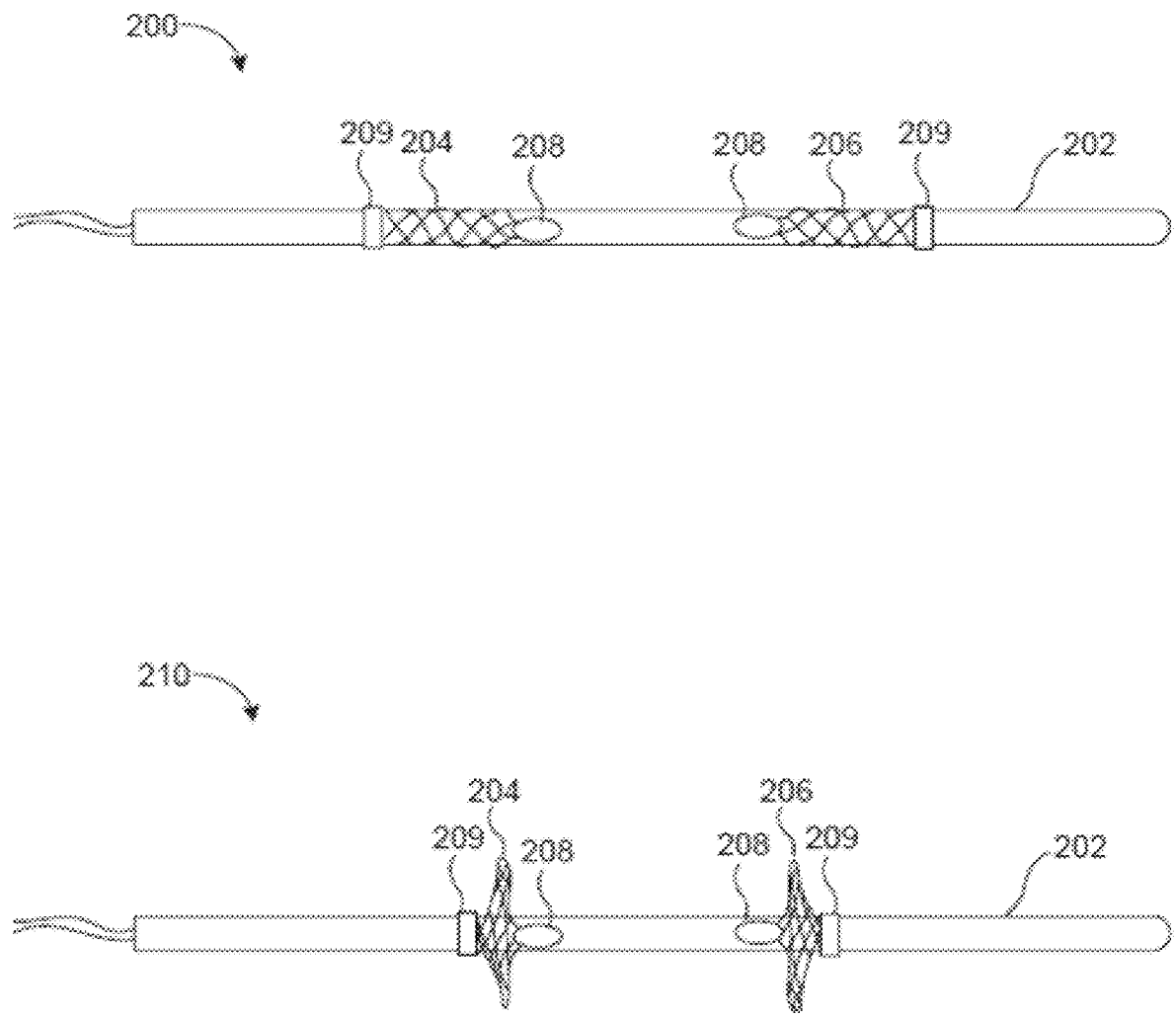
FIG. 2 illustrates an intraluminal microneurography probe having expandable wire mesh electrodes, consistent with an example.

Another example of a probe configured to characterize nerve activity near an organ such as a kidney is shown in FIG. 2, wherein a probe assembly is shown generally at 200. Here, a probe body is shown at 202, having mesh electrodes 204 and 206 affixed thereto at attachment points 208. The mesh electrodes are substantially similar to the helical wire electrodes of FIG. 1, except that several such electrodes are interwoven to form a mesh that is closely wrapped around the probe body 202. In this example, each mesh electrode also has a sliding collar element 209 located at the end of the mesh electrode opposite attachment point 208. In the probe assembly shown generally at 200 the mesh electrodes 204 and 206 can be said to be in non-deployed positions. When the mesh electrodes 204 and 206 are in their non-deployed positions, they can conform to or remain close to the outer surface of the probe body 202, e.g., as shown in FIG. 2. In an alternative embodiment, the mesh electrodes 204 and 206 are retained within one or more inner cavities of the probe body 202 when they are in their non-deployed positions.

This sliding collar 209 when moved toward the attachment point 208 causes the mesh to expand around the probe body 202, as shown generally at 210. In other words, in the probe assembly shown at 210 the first and second mesh electrodes 204 and 206 have been deployed. Accordingly, at 210 the mesh electrodes 204 and 206 can be said to be in their deployed positions, where they expand away from the probe body 202. Here, the expanded mesh electrodes 204 and 206 are configured to provide electrical contact, such as with an artery wall, in a diameter significantly larger than the diameter of the probe body 202. This enables insertion of the probe body into an artery, and expansion of the electrodes 204 and 206 to contact the artery walls, without blocking blood flow through the artery. Although the examples of FIGS. 1 and 2 show two probe configurations that can achieve such functions, probe configurations other than those shown here may also be configured to achieve these or similar functions.

Figure 3:
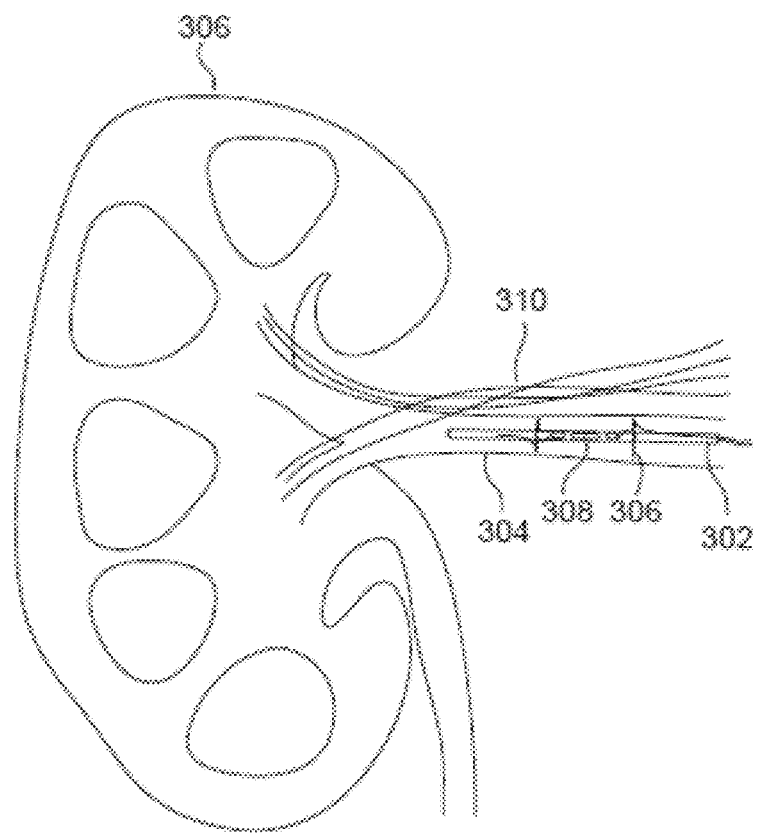
FIG. 3 shows introduction of an intraluminal microneurography probe into an artery in a location near a kidney, consistent with an example.

FIG. 3 illustrates one example of use of such a probe, in which a probe 302 such as that shown in FIG. 1 or FIG. 2 (or FIGS. 17A and 17B discussed below) is introduced into a blood vessel, such as an artery 304, in a location near a body organ such as kidney 306. The probe is introduced via a sheath in some examples, such as where a sheath is advanced to the intended probe location in the artery, and then withdrawn sufficiently to expose the probe 302 to the artery 304. The probe 302 here comprises a stimulation electrode such as electrodes 104 and 204 of FIGS. 1 and 2, and a sense electrode such as electrodes 106 and 206 of the same Figures.

When deployed, the electrodes are expanded as shown at 308, such that they are near or touch the walls of the artery 304. The electrodes are thereby located nearer the nerve bundle 310 connecting the kidney to the central nervous system, as the nerve bundle tends to approximately follow the artery leading to most body organs. As shown at 310, the nerve bundle tends to follow the artery more closely at the end of the artery closer to the kidney, while spreading somewhat as the artery expands away from the kidney. As a result, it is desired in some examples that the probe is small enough to introduce relatively near the kidney or other organ, as nerve proximity to the artery is likely to be higher nearer the organ.

When in place, a practitioner can use instrumentation coupled to the sense electrode and stimulation electrode to stimulate the nerve, and sense and monitor for nerve response signals used to characterize the nervous system response to certain stimulus. The practitioner can also use the instrumentation coupled to the sense electrode to sense and monitor intrinsic nerve signals. In a further example, an ablation element 308 is configured to ablate nerve tissue, such as by using radio frequency, microwave, cryotherapy, ultrasound, or other energy, such that the probe can actively stimulate the nerve and sense resulting neural signals in between applications of energy via the ablation element 308, enabling more accurate control of the degree and effects of nerve ablation. In other examples, a probe 302 lacking an ablation element can be remove via the sheath, and an ablation probe inserted, with the ablation probe removed and the probe 302 reinserted to verify and characterize the effects of the ablation probe.

Figure 4:
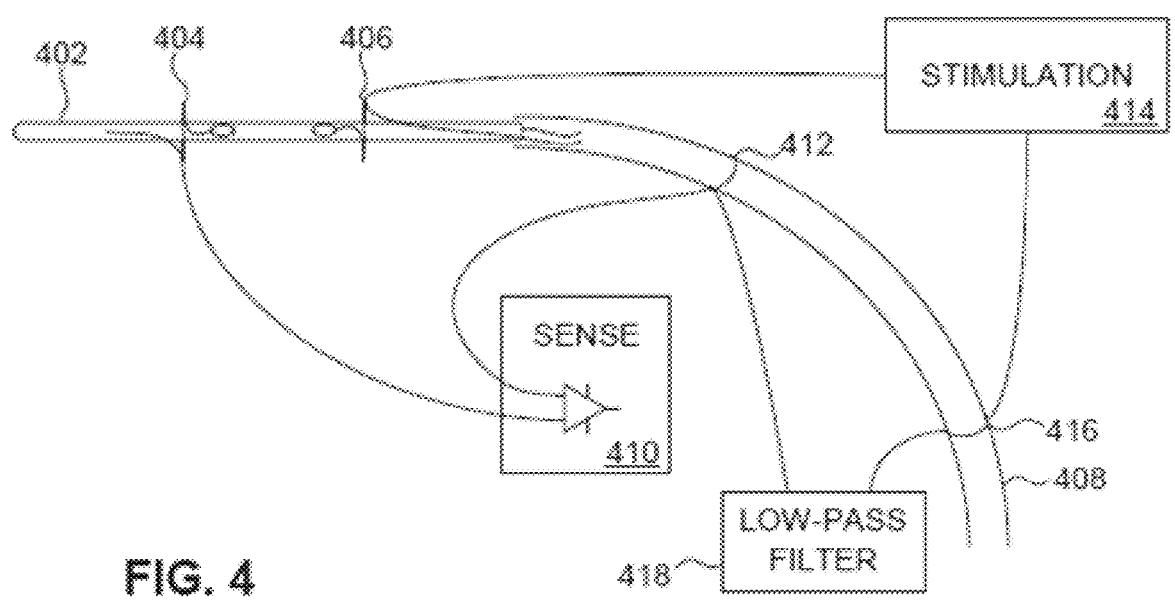
FIG. 4 shows an intraluminal microneurography probe and sheath assembly coupled to associated instrumentation, consistent with an example.

FIG. 4 shows an intraluminal microneurography probe and sheath assembly coupled to associated instrumentation, consistent with an example. Here, a probe body 402 has an expandable sense electrode 404 and an expandable stimulation electrode 406, couple via wires to instrumentation. A sheath 408 is used to introduce the probe into an artery or other biological lumen or suitable location, and to carry instrumentation wires and mechanical connections used to manipulate the expandable electrodes. The electrodes are not shown here running through the sheath, but are instead shown as schematic links between the electrodes and various instrumentation circuitry for clarity.

In this example, the expandable sense electrode 404 is coupled to a sense circuit, such as a differential amplifier as shown at 410, with the other input to the sense amplifier circuit coupled to a ground electrode such as local ground electrode 412 coupled to the sheath 408. In another example, local ground electrode is located elsewhere, such as on the probe body 404. The expandable stimulation electrode 406 is similarly coupled to a stimulation circuit 414 that is operable to provide a stimulation voltage or current signal of a desired pulse shape, intensity, and duration to the expandable stimulation electrode 406, with reference to body ground. Body ground is established in this example by a body ground electrode 416, which is here also shown as coupled to the sheath 408, but which in other embodiments will take other forms such as an electrode coupled to the body's skin. Here, the body ground electrode 416 is further coupled to the local ground electrode 412 by use of a low-pass filter, having a frequency response or time constant selected such that the local ground electrode does not drift significantly from the body ground level but retains the ability to accurately detect and characterize local nerve impulses.

The electrodes in this example comprise electrical wires that are significantly smaller than are used in other applications such as cardiac probes, in part because the pulse duration in the nerve bundle leading to most body organs is typically much shorter than a cardiac muscle excitation signal. In one embodiment, the sense electrode 404 therefore comprises a wire or mesh of wires having a diameter of 8-10 thousandths of an inch, while in other examples the wire diameter is 5-10 thousandths, 5-15 thousandths, or any size under 15, 10, 8, or 5 thousandths of an inch. The sense electrode is thereby configured to accurately detect a typical nerve action potential of 2 milliseconds traveling at a meter per second without smearing or distorting the measured pulse due to an overly large electrode.

The stimulation electrode in various examples comprises a wire or mesh of wires having any of the above sizes, but in another example, it is desired that the stimulation electrode 406 be substantially larger than the sense electrode 404 to avoid hyperpolarization of the nerve in the region of the electrode during stimulation.

Wire size of electrodes such as the sense electrode 404 is selected in further examples based on a typical nerve conduction velocity range of 0.4-2 meters/second, with nerve impulses ranging from 1-3 milliseconds. Also, the sense electrode 404 and stimulation electrode 406 are desirably placed a sufficient distance apart, such as 3 centimeters, to accurately detect a typical nerve action potential of 2 milliseconds without interference from the stimulation electrode.

Because the size of organ arteries such as the renal artery are typically in the range of 5 millimeters in diameter, it is desired to have a probe body that is a fraction of this size, such as having a diameter of 2.5 mm, 2 mm, 1 mm, or similar. This enables introduction of the probe without interfering with blood flow through the artery, such that the expandable electrodes can still expand to the artery walls without further significantly impeding blood flow.

Figure 5:
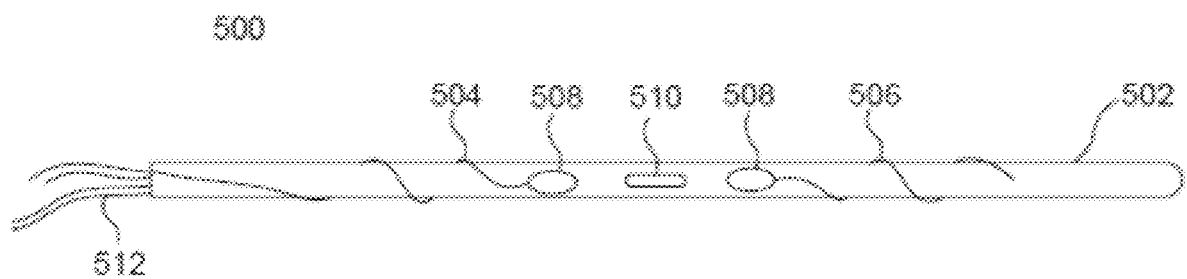
FIG. 5 shows an intraluminal microneurographic probe having an RF ablation antenna, consistent with an example.

FIG. 5 shows an intraluminal microneurographic probe having an RF ablation antenna, consistent with an example. The probe 500 in this example has a probe body 502 and first and second helical electrodes 504 and 506 as in the previous examples, and each of the helical electrodes is again attached to the probe body at one end as shown at 508. A Radio Frequency (RF) ablation antenna, such as a microwave antenna, is shown at 510, such as is shown at 308 in FIG. 3. The RF ablation antenna 510 is connected to a signal source using coaxial cable 512, such that the probe can actively stimulate the nerve and sense resulting neural signals using helical electrodes 504 and 506 in between applications of energy via the ablation element RF ablation antenna 510, providing more accurate control of the degree and effects of nerve ablation. The RF ablation antenna in various examples comprises a coil, a monopole or dipole, a reflector, a slot, a feedhorn, one or more rings, or combination of such elements to control ablation direction and heating in the region of the antenna. In a further example, a cooling element such as a liquid jacket or tube is provided to cool tissue not targeted by the RF ablation antenna, and in some examples to shield RF energy from such tissue.

Figure 6:
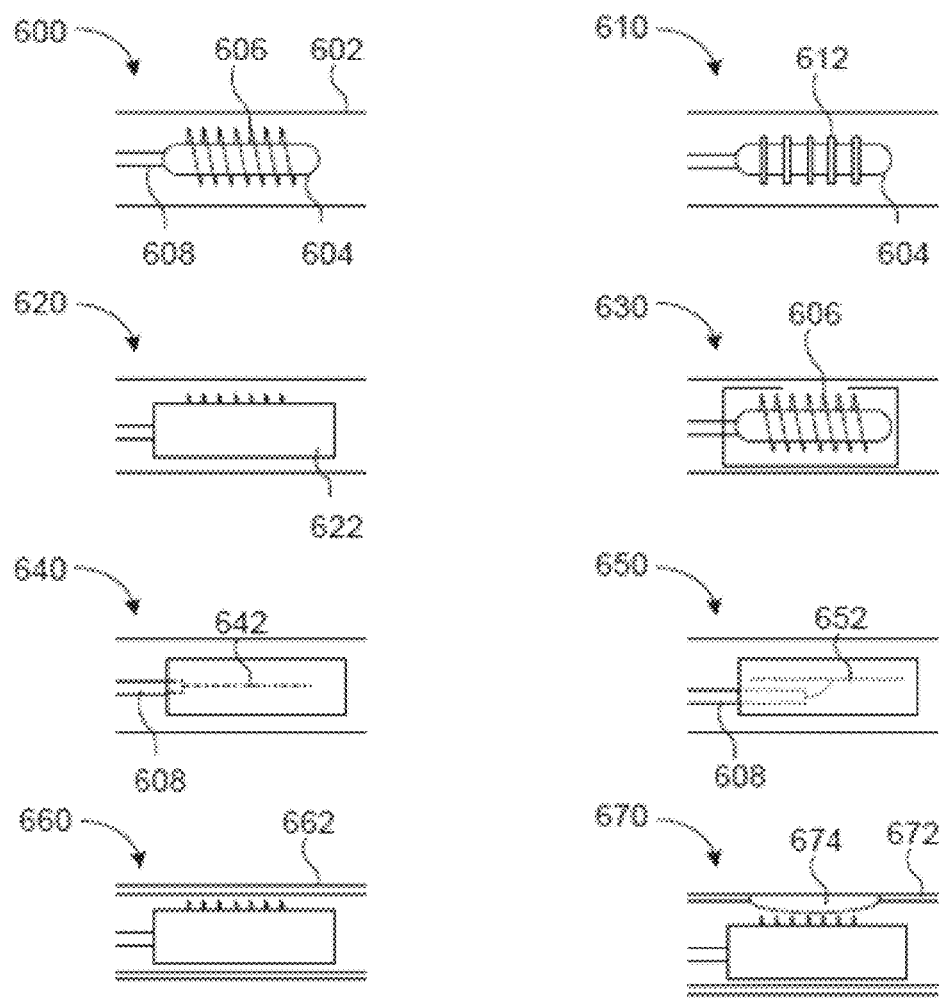
FIG. 6 shows a variety of RF ablation antenna configurations for an intraluminal microneurographic probe, consistent with various examples.

FIG. 6 shows RF ablation antenna configurations for an intraluminal microneurographic probe, consistent with various examples. In the example shown at 600, a probe body 602 includes an RF microwave ablation element having a core 604, and a coil element 606 coupled to a coaxial cable 608. In this example, the coil 606 serves as the microwave antenna, and in various examples it is wound around a ferrite or other ferromagnetic core, oriented differently than as shown, or shielded to restrict the direction of RF emission.

Another example microwave antenna configuration is shown at 610, in which a core 604 includes two or more rings or windings 612 that are spaced at least a fraction of a wavelength apart from one another. The phase of the signal provided to the two or more windings 612 can therefore be varied to control the radiation pattern of the microwave antenna, directing energy to adjacent tissue as desired. In a more detailed example, the phase, frequency, or other parameters of the energy supplied to the windings is controlled such as in a phase-steered array to target tissue at a certain depth or distance from the microwave probe for ablation.

Because the radiation pattern of the microwave antennas shown at 600 and 610 is approximately the same around the circumference of probe body 602, the example microwave antenna shown at 620 further comprises a reflector 622. Here, the reflector 622 wraps around the sides and bottom of the side view of the coil antenna as shown at 600, absorbing or reflecting radiation that is not directed upward as shown. This enhances the microwave antenna's capacity to target specific tissue, such as nerves, that are present in a known direction from the probe body 602.

In a similar example, the microwave antenna configuration shown at 630 includes a coil antenna 606 such as was shown at 600, but also includes a shield 632 around the antenna having an aperture 634 on the side of the shield configured to let radiation pass. The size, position, and other configuration parameters of the aperture 634 are therefore configured to pass radiation in the direction of nerve tissue to be ablated, while shielding radiation from being emitted in other directions unnecessarily. Combining technologies such as shielding and phase steering can be used in a further example to control both the direction and depth of emitted radiation, targeting tissue with greater discrimination than a simple coil antenna such as that shown at 600.

The microwave antenna in other examples comprises a configuration other than a coil or coils, such as a monopole or dipole antenna. A monopole microwave antenna is shown in the example at 640, where a coaxial cable 608 is coupled to an antenna element 642. Here, the coaxial cable is connected to one end of the antenna element 642, and the coaxial cable provides microwave energy to the antenna to ablate nearby nerve tissue. The frequency of the microwave energy and the antenna are typically configured so that the antenna is a quarter wavelength or longer relative to the microwave energy being provided.

At 650, a dipole antenna 652 is similarly configured, coupled to the coaxial cable and to a microwave power source in the center of the antenna 652 rather than at one end. This configuration makes the antenna 652 a dipole antenna rather than a monopole as shown at 640/642. Although the radiation pattern from a monopole antenna is primarily perpendicular to the antenna, it can vary in width and have lobes at varying angles from perpendicular depending on the wavelength of the microwave energy signal provided and the length of the antenna. The dipole antenna shown at 650/652 can be configured to have a single, narrow lobe of radiated energy perpendicular to the antenna, which may be of greater value in targeting tissue for ablation. In a further example, multiple monopole or dipole antenna elements are provided, such as shown at 610, and phase steering or other such methods are used to enhance control over the direction and depth of radiated microwave power.

Because the nerve or other tissue being ablated is typically on only one side of the probe body 602, shields or apertures such as those shown at 620 and 630 may be employed with various microwave antenna configurations to limit emission of RF energy to the direction of the tissue to be ablated. Because microwave antennas can cause significant heating in tissue surrounding the antenna, some probe examples also include one or more cooling elements, such as a coolant jacket, in the vicinity of the microwave antenna. At 660, an antenna with a shield such as is shown at 620 is provided, along with a probe body having both an inner and outer wall forming a cooling jacket 662. The cooling jacket in this example reduces heating from the antenna in the region immediately surrounding the probe body, such as from a heated antenna coil or other element, or from a reflector or shield. In a more detailed example, cooling fluid is circulated within the cooling jacket, such as by a cooling fluid pump feeding coolant to the probe assembly.

In another example shown at 670, a probe assembly has a cooling jacket 672 that does not extend around the entire probe body in the vicinity of the microwave antenna. In a more detailed example, the cooling jacket 672 is interrupted by probe body portion through which coolant does not flow, such as the cooling jacket aperture shown at 674. In a further example, the cooling jacket comprises a metallic material that can also shield microwave energy from traversing through the cooling jacket, while the cooling jacket aperture 674 comprises a material that not metallic and that allows microwave energy to be emitted through that portion of the probe body. Such a configuration provides for selective microwave radiation in the desire direction, and also places cooling fluid or other cooling elements in close contact with metallic shield portions of the probe to more effectively cool the metallic shield elements.

An intraluminal microneurography probe such as those shown in FIGS. 1-6 can be introduced into an artery via a sheath, and used to monitor nerve activity during normal operation of an organ. This enables characterization of nerve activity in the organ, such as to diagnose or treat a variety of conditions. In one such example, a probe is used for characterization of overactive nerves reaching the kidney in patients suffering from hypertension, and to monitor ablation of the nerves to a point where nerve activity is in the desired range as measured using the probe. In other examples, the probe may be used while other actions are performed, such as to monitor nerve activity to a patient's prostate while surgery or other methods remove material to treat prostate cancer or enlarged prostate problems. Because it is desirable that significant nerve connection to the prostate be preserved during such procedures, a probe such as those presented here can be used to minimize the chances of nerve damage that may affect normal function of the prostate.

A probe such as those shown here can also be used to diagnose various organ dysfunctions, such as where an organ overreacts to nerve impulses or overstimulates the nerve in response to organ activity. The probe is here described in some examples as an intraluminal probe, meaning the probe may be introduced into various lumina or pathways in the body, such as arteries, veins, the gastrointestinal tract, pathways of bronchi in the lungs, pathways of the genitourinary tract, and other such pathways. The probe is neurographic in the sense that it enables characterization, such as measurement, recording, and visualization of neurologic activity in the vicinity of the probe. Because the autonomic nervous system regulates a wide variety of functions within the body, including circulation, digestion, metabolism, respiration, reproduction, etc. by a network of parasympathetic and sympathetic nerves that typically accompany the blood vessels supplying blood to the organs they regulate, an intraluminal neurographic probe such as those described here can be used to measure or characterize the regulation of many of these functions by introducing the probe into the blood vessels near the organ of interest.

Although the example of FIG. 3 illustrates ablation of nerves near the kidney to regulate kidney function in treating hypertension, nerves regulating liver function accompany the hepatic artery and the portal vein, nerves regulating the stomach accompany the gastroduodenal arteries, nerves from the superior mesenteric plexus accompany the superior mesenteric artery and branch to the pancreas, small intestine and large intestine, and nerves of the inferior mesenteric plexus accompany the inferior mesenteric artery and branch to the large intestine, colon and rectum. These examples illustrate other organs that can be characterized and regulated using probes and techniques such as those described herein.

In treating kidney function, it is significant that renal sympathetic nerves have been identified as a major contributor to the complex pathophysiology of hypertension. Patients with hypertension generally have increased sympathetic drive to the kidneys, as evidenced by elevated rates of the renal norepinephrine "spillover." It is therefore believed that ablating renal sympathetic nerve function with sufficient energy will cause a reduction in both systolic and diastolic blood pressure, relieving hypertension in the patient.

Studies have shown that most nerves surrounding the renal arteries are within 6 mm to 7 mm of the renal artery lumen, with nerves clustered more closely around the artery near the kidney, making measurement and treatment of the nerves from the renal artery practical. Monitoring nerve activity prior to, during or between nerve ablations, such as via the probes described herein, is an important tool in characterizing and regulating the degree to which nerve activity has been reduced. Before introduction of probes such as those described herein, clinicians were unable to readily determine an extent of renal nerve modification during a procedure in a clinically relevant timeframe, and could not measure durability of nerve damage during a follow-up period after denervation. Now, with probes such as those described herein available, a clinician can take such measurements, and can assess health of renal nerves pre-procedurally to select or screen patients for denervation.

In operation, a clinician can measure nerve activity such as renal nerve activity by emitting an electrical pulse through stimulation electrodes in the probe, and recording propagation along renal nerve fibers using the sense electrode or electrodes on the probe. The clinician can then compare renal nerve activity pre- and post-denervation to determine the degree of nerve ablation incurred, thereby more accurately achieving the desired degree of nerve ablation during treatment of the patient. More specifically, a clinician can apply an electrical stimulus to a site in the proximal renal artery, and then monitor or record the nerve activity between the stimulus site and the kidney, thereby measuring the resultant downstream action potential in the nerve. Nerve ablation is then performed, and the stimulus and measurement of the nerve is repeated to verify a reduced or eliminated evoked potential detected in the nerve as a result of stimulation via the probe's electrodes, and can also be used to decide if further denervation should be performed.

The probe examples described in the examples here can therefore provide real-time feedback on functionality of renal nerves, providing integrated evaluation of all nerve fibers surrounding a renal artery, at the artery proximal, distal, and renal branch locations. The probe is easily deployed via catheter-based delivery, and can be used as a standalone product or integrated with an ablation element. The probe system's low hardware and software costs and easy learning curve for clinical users make the probe system well-adapted for widespread adoption for treatment of nerve conditions such as those described herein.

A variety of experiments have been conducted to verify operation of probes such as those described herein, including using an isolated canine/porcine kidney and the associated vasculature to conduct certain tests. In one such test, probes such as those of FIGS. 1-6 were used to verify renal nerve health by measuring spontaneous renal nerve activity using intraluminal microneurography, demonstrating that such probes cause effective stimulation and recording of renal nerve activity. In the tests, stimulus-elicited response established a baseline recording of renal nerve activity, and the circumferential section of renal nerve fibers were damaged using a scalpel. Re-measuring the stimulus-elicited response and comparing the response to the established baseline recording of renal nerve activity confirmed that spontaneous renal nerve activity had been reduced.

Figure 7:
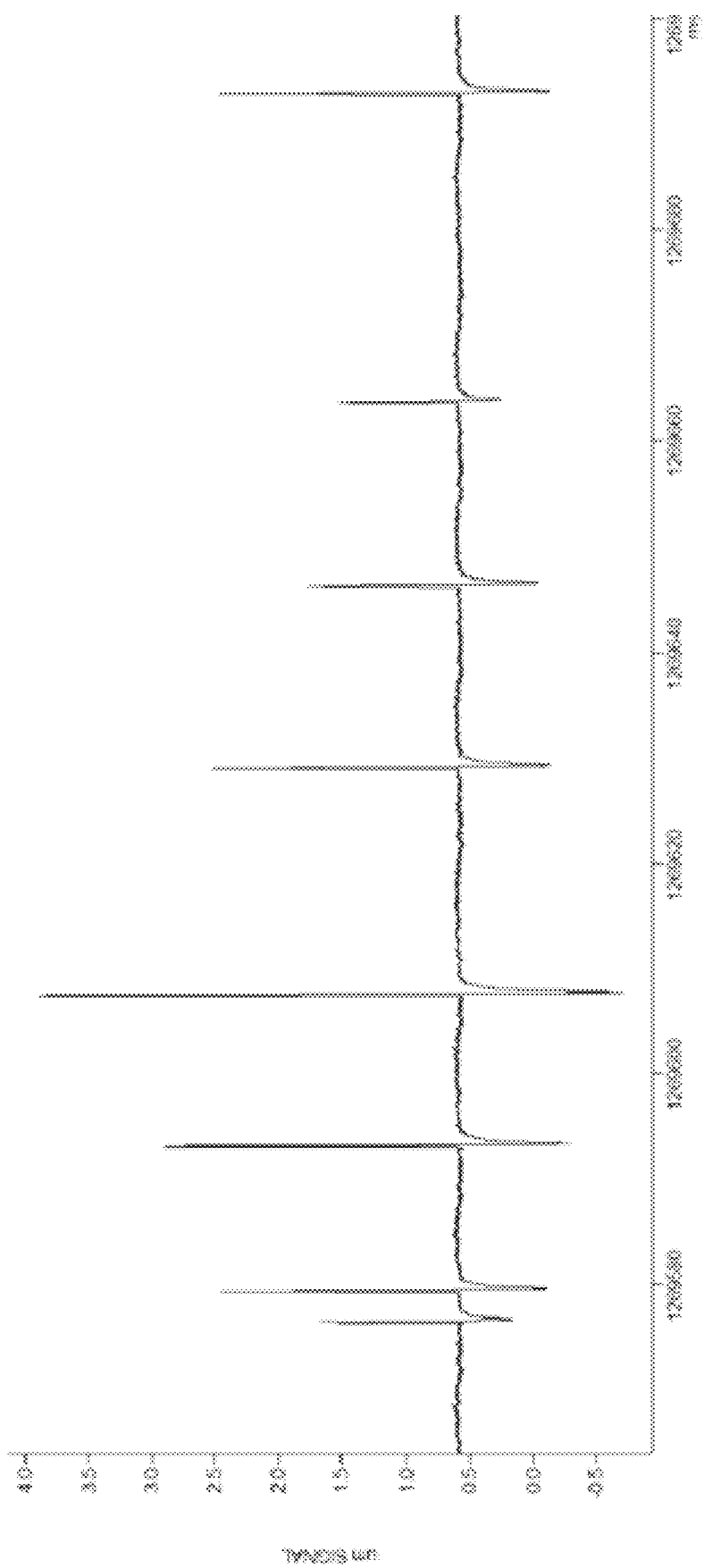
FIG. 7 shows spontaneous nerve activity, measured from the wall of the renal artery of an explanted kidney, consistent with an example.

FIG. 7 shows spontaneous nerve activity, measured from the wall of the renal artery of an explanted kidney. Here, the measurements are taken using needles placed in the wall of the renal artery, using relatively invasive microneurography techniques.

Figure 8:
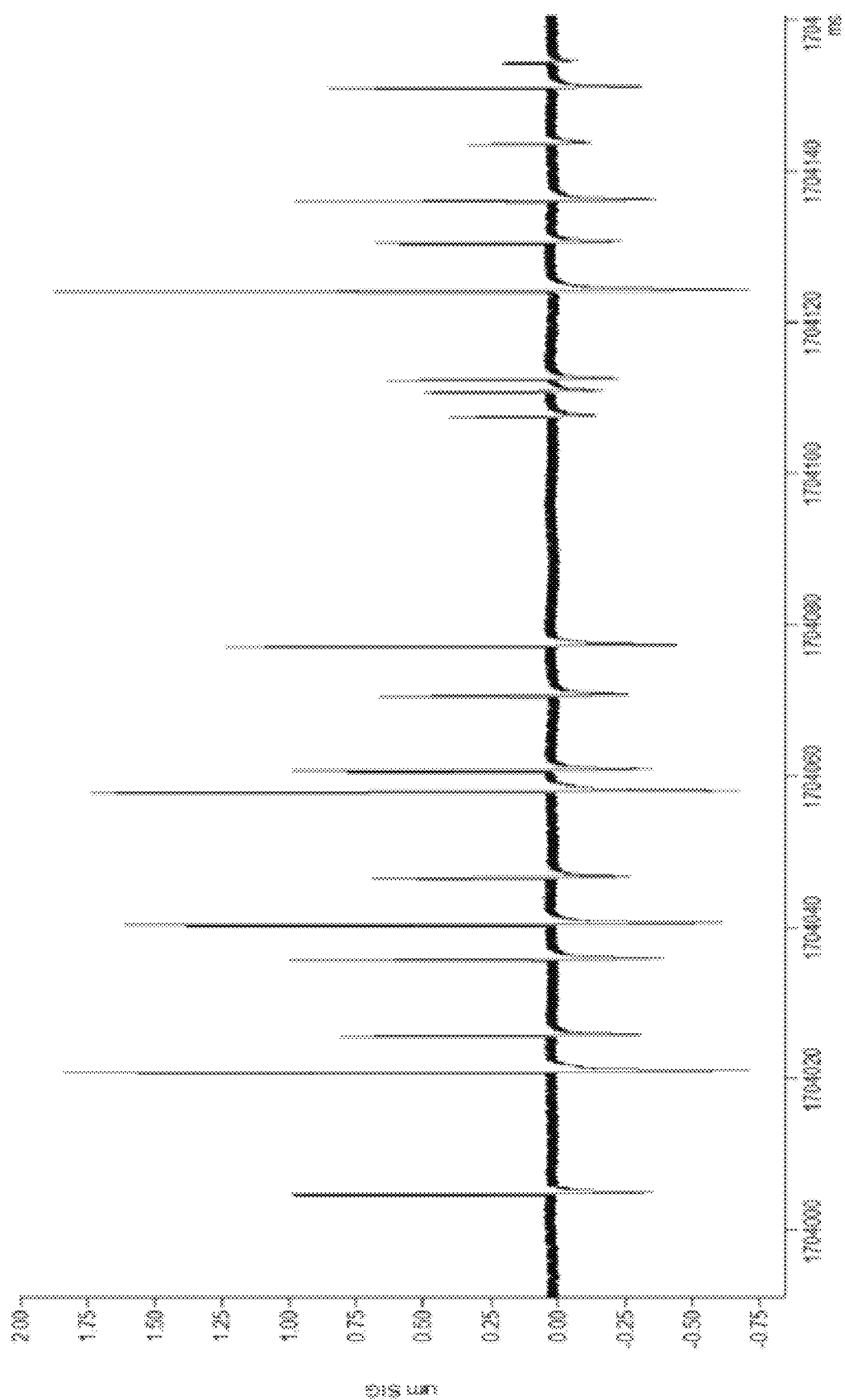
FIG. 8 shows spontaneous nerve activity in the wall of the renal artery of an explanted kidney using an intraluminal microneurography probe, consistent with an example.

FIG. 8 shows spontaneous nerve activity in the wall of the renal artery of an explanted kidney, using an intraluminal microneurography probe. Here, the peak signal levels are somewhat reduced relative to the method of FIG. 5, but accurate detection, measurement, and recording of spontaneous renal nerve activity signals is shown to be achieved.

Figure 9:
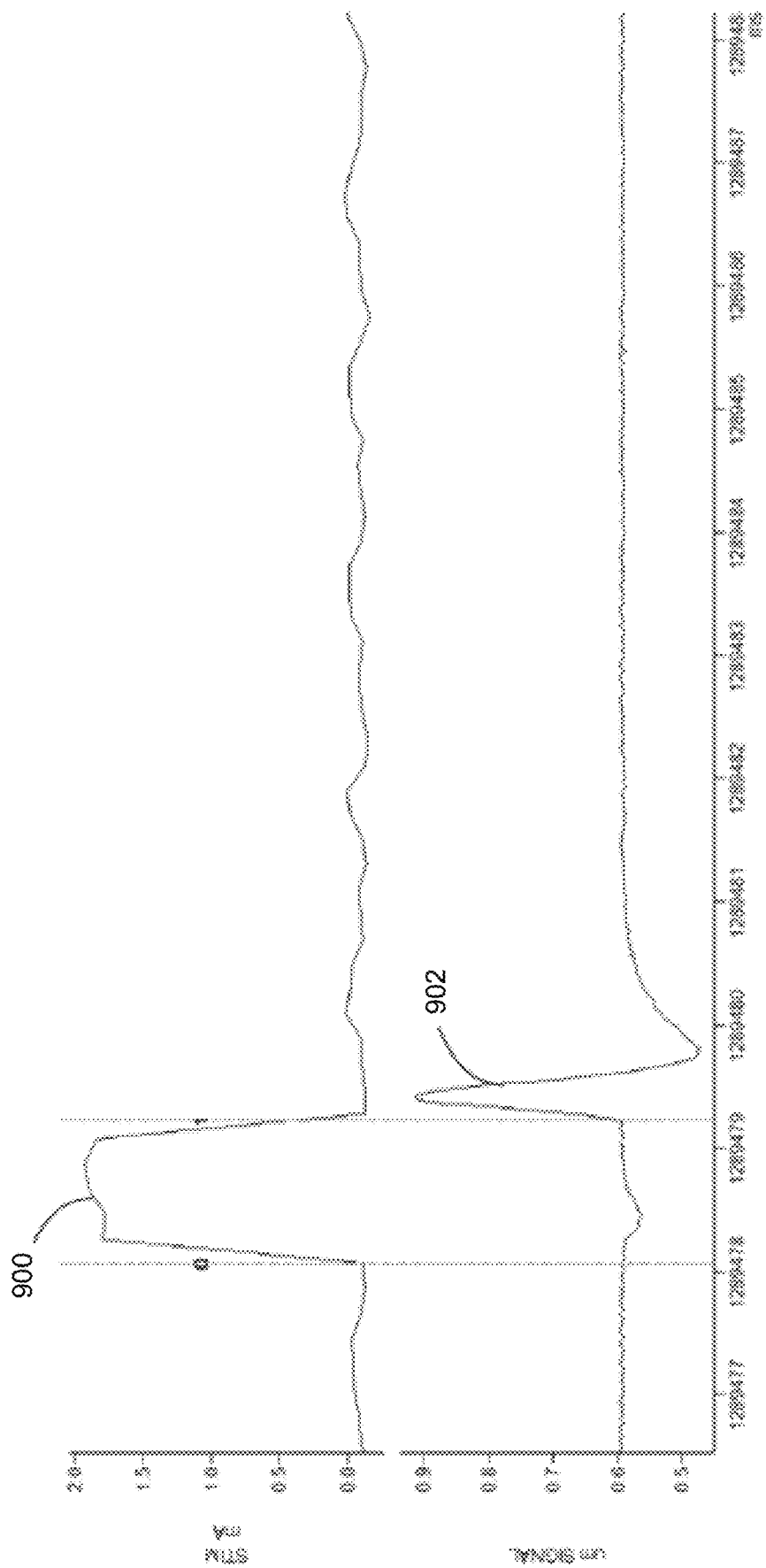
FIG. 9 shows a stimulus signal and the resulting measured renal nerve activity action potential, consistent with an example.

In FIG. 9, a stimulus signal 900 and the resulting measured renal nerve activity action potential 902 are shown. Here, the renal nerve action potential is measured using needles in the artery wall, using a stimulus time of approximately 1.3 milliseconds, configured to avoid overlapping the stimulus and response signals based on the expected conduction velocity and the selected stimulus and sense electrode spacing.

Subsequent testing on live animals also proved successful, with a series of experiments conducted in a live rat model to confirm detection of renal nerve activity in a living animal with competing signals from cardiac electrical activity and respiratory movement. Excellent results were achieve using probes having configurations such as those described herein, based on an experimental procedure in which an evoked renal nerve activity baseline was determined in the intact renal artery, and renal nerve activity was measured as the renal artery was transected.

Figures 10A, 10B, 10C:
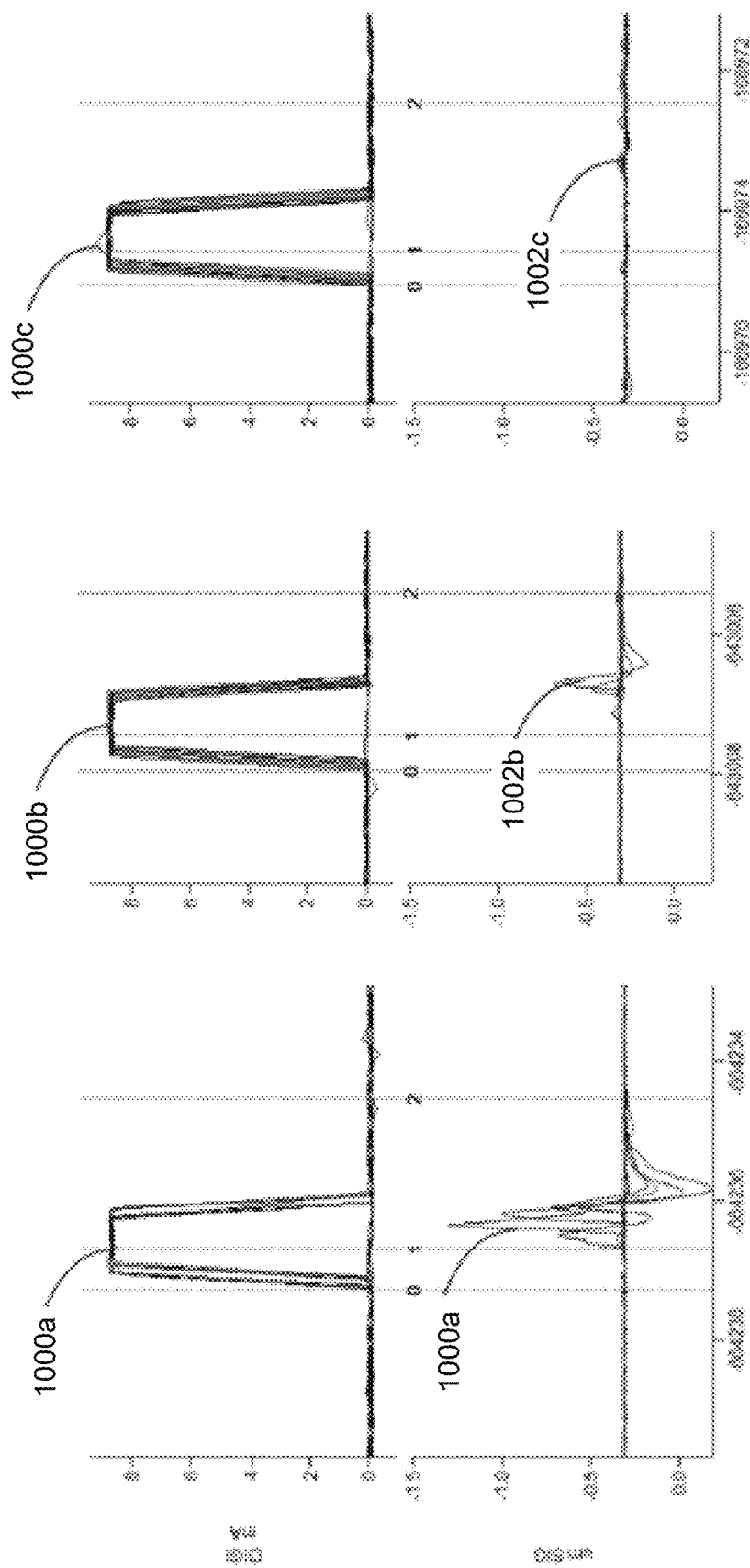
FIGS. 10A-10C also show the progression of elicited potentials in arterial nerves in response to a stimulus pulse as the relative amount of nerve destruction increases. More specifically.

Destruction of the renal nerves, and the resulting effects on renal nerve activity signals measured as a result of an applied stimulus signal, are shown in FIGS. 10A-10C, which can be referred to collectively as FIG. 10. Here, ten sets of data are overlaid to generate a graph representative of typical levels and distribution of renal nerve activity response to a stimulus signal as varying degrees of arterial transection.

At 1000a, the evoked renal nerve activity baseline measurements taken prior to cutting across the artery are taken as a reference. At 1000b, the artery is 50% transected, resulting in significant reduction in observed renal nerve activity response, and at 1000c, the artery is 100% transected, and little to no renal nerve activity response is observed. In this example, transection of the renal arteries was used to destroy renal neural pathways because rat renal arteries are too small for effective radio frequency ablation. FIGS. 10A-10C also show the progression of elicited potentials in arterial nerves in response to a stimulus pulse as the relative amount of nerve destruction increases. FIG. 10A is a plot showing a stimulus signal 1000a and a detected elicited response 1002a before performing a destructive operation on the arterial nerves. In some examples, FIG. 10A can represent a baseline measurement. FIG. 10B illustrates a stimulus signal 1000b and a detected elicited response 1002b. As can be seen, the elicited response 1002b is significantly smaller than elicited baseline response 1002a, indicating that significant destruction of arterial nerves has been performed. FIG. 10C illustrates a stimulus signal 1000c and a detected elicited response 1002c after still more arterial nerve destruction has been performed. As can be seen, the elicited response 1002c is much smaller than that of either the elicited baseline response 1002a or the response 1002b, and is almost non-existent. This implies that further, or possibly complete, arterial nerve destruction has taken place.

Figure 11:
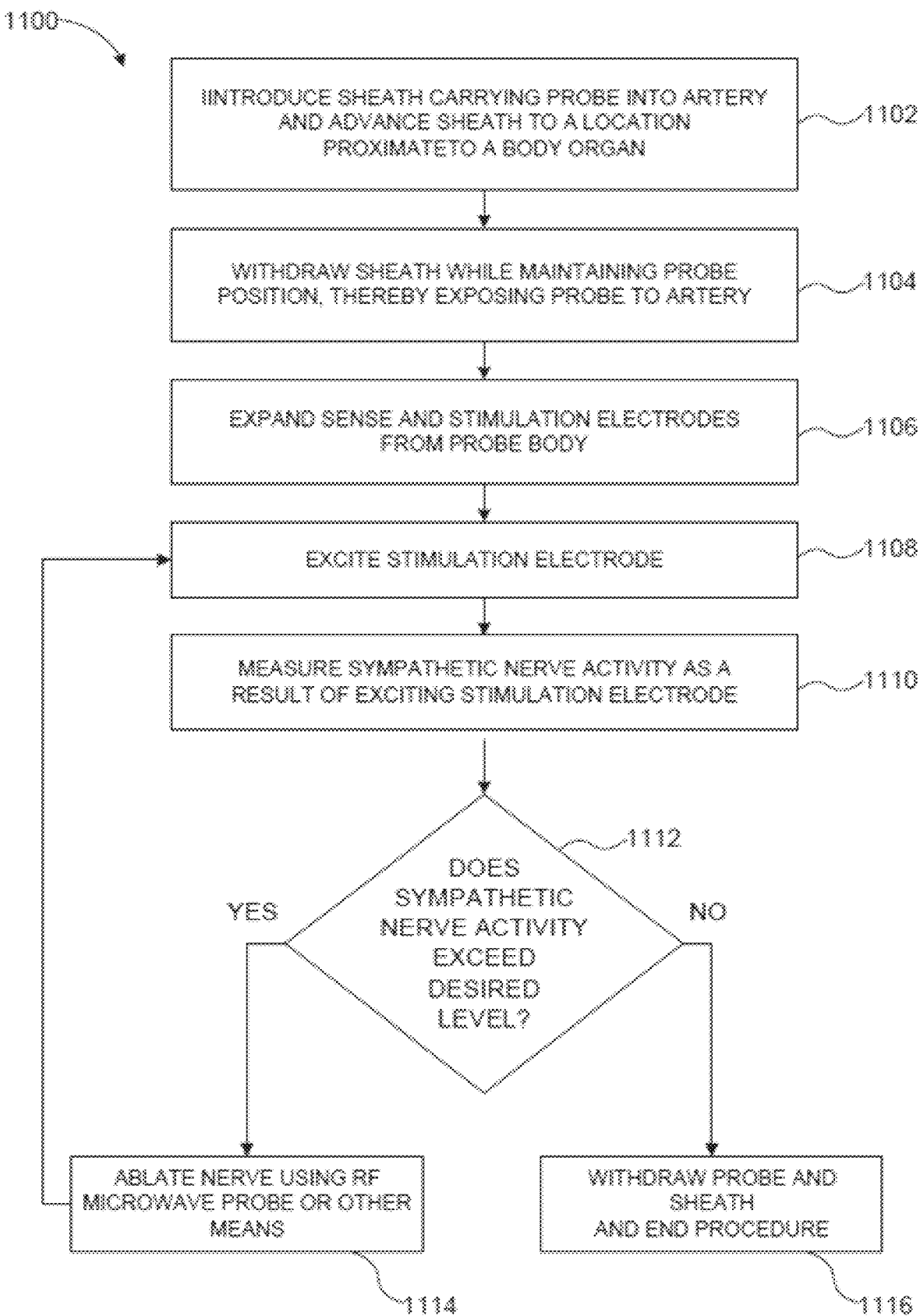
FIG. 11 is a flowchart illustrating a method of using an intraluminal microneurography probe to treat a medical condition, consistent with an example.

FIG. 11 is a flowchart illustrating a method of using an intraluminal microneurography probe to treat a medical condition, consistent with an example. As shown generally at 1100, a method of treating a medical condition involves using probe to excite and measure nerve activity near an organ, and selectively ablating nerve tissue near the probe until the desired nerve activity in response to the excitation is observed.

A sheath carrying the probe into the artery is inserted at 1102, and is advanced to a location in the artery near a body organ that is the subject of the medical condition and treatment, such as treating a kidney's neural response to treat hypertension. The sheath is withdrawn slightly at 1104, exposing at least part of the probe including an expandable sense electrode and an expandable stimulation electrode to the artery. At 1106, the expandable stimulation and sense electrodes are expanded, such that the electrodes contact the arterial wall. At this point, the probe is properly deployed and ready to perform measurement.

The expandable stimulation electrode is excited at 1108, inducing an electrical signal into the nerves adjacent to the arterial wall. The nerves propagate the signal from the stimulation electrode, which can be observed at 1110 as nerve activity as a result of exciting the stimulation electrode. The observed nerve activity can then be measured, characterized, stored, viewed, etc., to determine whether the nerve activity exceeds a desired level at 1112. If a desired level of nerve activity is exceeded, nerves proximate the probe are ablated at 1114, such as using an radio frequency or microwave ablation element comprising a part of the probe located between the sense electrode and the stimulation electrode, as shown in FIGS. 5 and 6. Steps 1108-1112 are then repeated and the nerve is optionally ablated again, until the nerve activity is determined not to exceed the desired level at 1112. At that point, the measurement and nerve ablation is complete, and the probe and sheath can be withdrawn at 1116.

Certain embodiments of the present technology enable the real-time assessment of sympathetic and parasympathetic nerve activity by comparing stimulus-elicited potentials before and after the delivery of a destructive means to the selected nerves. Electrical stimulation is delivered to the arterial wall in a fashion to reliably elicit maximal nerve activity. The resultant activity transmits distally past a destructive means and towards a system used to record the elicited activity. Comparisons of the neural bursts elicited before and after ablation can be used to indicate the continuity and integrity of the interposed nerve fibers.

Various methods of eliciting and assessing autonomic nerve activity can include inserting a probe containing both therapeutic means for performing destructive processes and stimulating and recording electrodes for eliciting and assessing nervous activity into the patient's body to a desired anatomic location. In some examples, the probe can be inserted through a blood vessel of the patient in order to elicit and assess nerve activity associated with nerves proximate that blood vessel. In still further embodiments, the probe is inserted into an artery into an organ, for example, those described above.

In some embodiments, a clinician may first use the electrodes in a monitoring fashion to establish baseline nervous system function. Alternatively, the clinician may first use the electrodes in a stimulation mode to initiate a nervous activity response which can be measured by the electrodes in a monitoring mode. The clinician may then apply destructive means to the tissue. The clinician may next apply the cycle of nerve stimulation and monitoring to assess whether or not the nerve activity has been abolished. If nervous activity still exists, then the device may indicate to the clinician a value indicative of nerve destruction completeness. For example, the device may estimate an amount of nerve destruction based on the magnitude of detected nervous activity compared to the magnitude of detected nervous activity prior to nerve destruction. The estimated amount of nerve destruction may be in the form of a percentage, for example. At this time, the clinician may assess the level of denervation or destruction and stop, or proceed to deliver another application of destructive means for a more complete lesion. The cycle of application, stimulation, and monitoring may be repeated until nervous activity is abolished, and/or the clinician has reached an intended level of denervation.

Various systems and devices can be used for performing such processes. Some embodiments of the invention comprise a probe for inserting into the patient, for example into a patient's renal artery or any other appropriate lumen in the patient's vasculature. The probe can include a plurality of electrodes directing an electrical stimulus into the patient's body, and for detecting electrical signals elicited within the patient. In various embodiments, electrodes can be arranged along the axis of the probe, around the circumference of the probe, or in any other appropriate arrangement for carrying out various methods according to the present invention. In some configurations, the probe and electrodes are such that, when the probe is inserted into a patent's artery, the electrodes are placed in contact with the artery lumen wall. Such contact permits the application of electrical stimulation from the electrodes to the wall, and the detection of electrical signals from the wall via the electrodes. Various example electrode configurations including a varying number of electrodes are shown in FIGS. 12A-12D and described below.

Figures 12A, 12B, 12C, 12D:
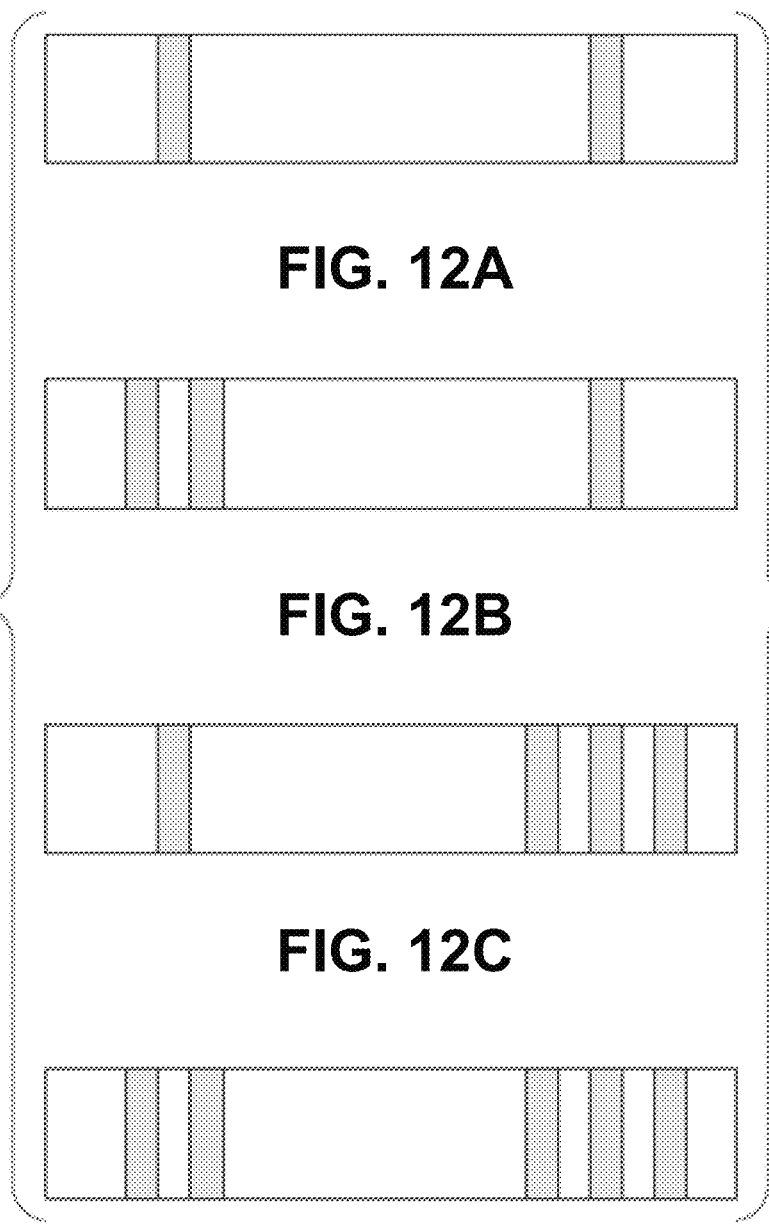
FIGS. 12A-12D are example probe designs according to various embodiments.

In some embodiments, such as that shown in FIG. 12A, the probe comprises a first electrode and a second electrode. Such a system can further include a third electrode applied on the patient's skin (not shown). A first electrode mounted on the probe can be used to deliver an electrical stimulus to the surrounding tissue in a monopolar fashion, with the electrode placed on the person's skin being used as the return electrode during stimulation. Distal to the stimulating electrode, the second electrode can be used to record elicited bursts of autonomic activity resulting from the stimulus from the first electrode to the third electrode. In some embodiments, during a recording session, the electrode placed on the skin can be used as the indifferent electrode of the electrode pair.

An alternate configuration, such as is shown in FIG. 12B, can include three (3) electrodes on the probe. In such a configuration two electrodes would be dedicated to stimulation and the third would be paired with the external electrode for monitoring.

Another alternative configuration, shown in FIG. 12C, can include four (4) electrodes on a single probe: one stimulating electrode, and three recording electrodes. The three recording electrodes can be setup to include an active electrode, an inactive electrode and a common electrode, for example. The one stimulating electrode can operate in a monopolar fashion, wherein an external surface electrode positioned on the patient's skin can serve as a return electrode. Alternatively, two electrodes on the probe can be used as stimulating electrodes and can operate in a bipolar fashion, while the remaining two electrodes could be used for recording/detecting signals, such as in the form of an active and inactive pair.

Still another alternative configuration, such as is shown in FIG. 12D, can include five (5) electrodes on a single probe: two stimulating electrodes to deliver stimulation in a bipolar fashion, and three recording electrodes, for example active, inactive and common electrodes. In general, any number of electrodes can be used for any number of purposes, such as delivering stimulation in a monopolar or bipolar fashion, recording/detecting electrical signals, or measuring any other electrical parameter that might be desired (e.g., resistance, capacitance, etc.). In various embodiments, properties of the recording electrodes can be adjusted to best receive action potentials or other signals passing along the arterial wall. For instance, in some examples, the impedance, separation distance, and size and geometry of the recording electrodes can be adjusted.

It will be appreciated that, while various examples are shown in FIGS. 12A-12D, suitable probes can include any number of electrodes for performing a variety of functions. For instance, further embodiments of a probe can include three or more stimulating electrodes. In some such examples, stimulating electrodes can include a pair of electrodes for bipolar stimulation as well as a reference electrode or a blocking electrode, as will be described below. In other embodiments, additional electrodes (e.g., third electrode, fourth electrode, etc.) can be used as alternative electrodes in the event that a first pair of electrodes does not make adequate electrical contact with the arterial wall of the patient. In such embodiments, alternate stimulating electrodes can be used to provide unipolar or bipolar stimulation to the patient's arterial wall.

In some embodiments, means for applying destructive energy to nerves within or proximate the probe are provided. Such destructive means can include, for example, radiofrequency (RF), ultrasonic, microwave, laser or chemical agents. In some embodiments, the destructive means are applied between the stimulating electrode(s) and the recording electrode(s). Accordingly, the stimulating electrode(s) applies a stimulus to the arterial wall and elicits a potential within the patient that travels at some propagation velocity (e.g., between approximately 0.2 m/s and approximately 8 m/s) toward the recording electrode(s), where it can be detected. When a destructive process is performed between the stimulating and recording electrode(s), subsequent elicited potentials traveling from proximate the stimulating electrode(s) toward the recording electrode(s) must traverse the region of nerves to which destructive means has been applied. Accordingly, any effect that the destruction process has on the elicited potential can be observed at the recording electrode(s).

Figure 13:
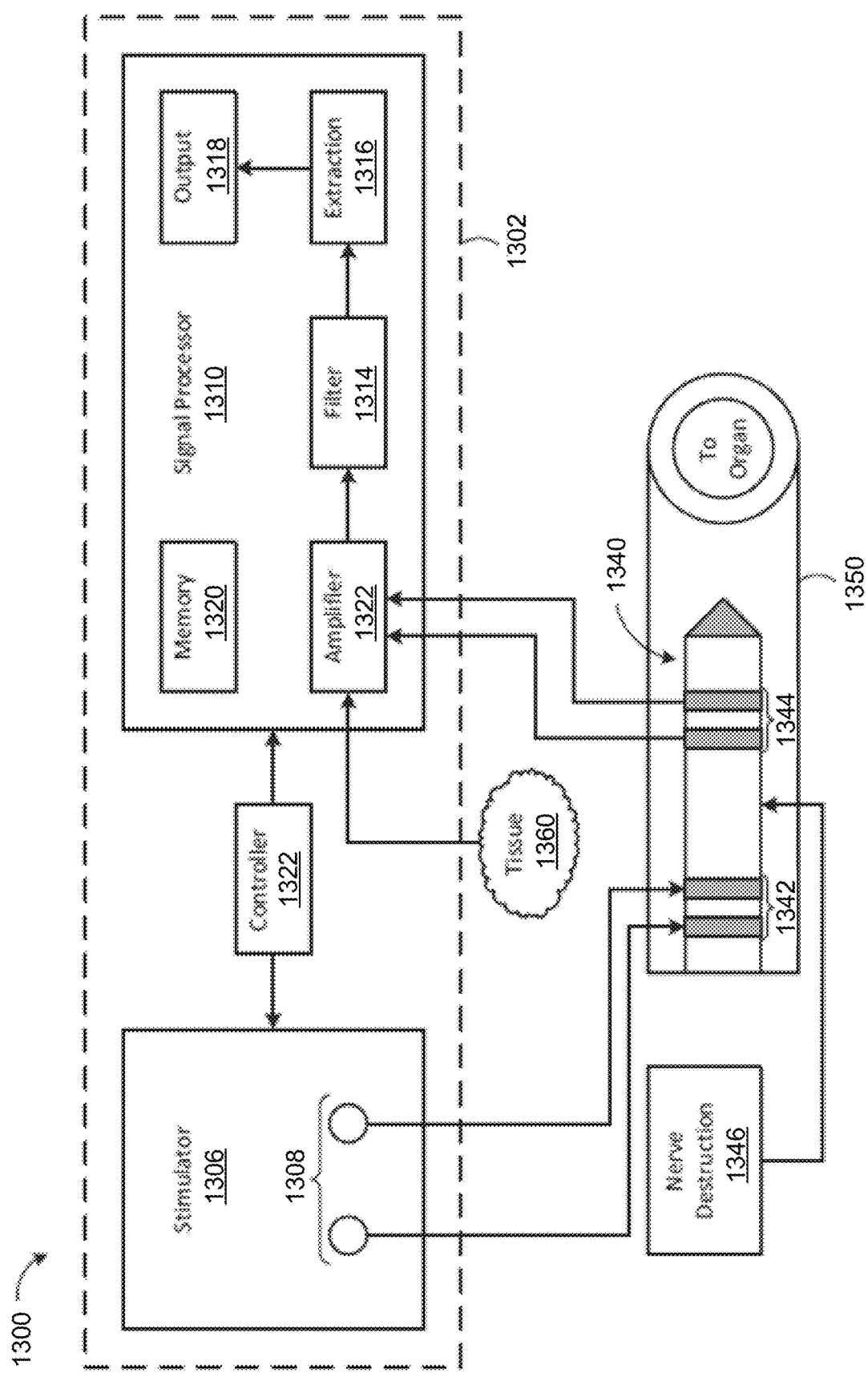
FIG. 13 is a schematic diagram of an example system for interfacing with a patient's arterial nerves.

As shown in FIGS. 12A-12D, the stimulating electrodes are shown on the left side of the probe, while the recording electrodes are shown on the right side. In some embodiments, the probe is inserted into an artery such that the recording electrodes are more proximate an organ associated with the artery than are the stimulating electrodes, such as shown in FIG. 13. However, in alternative embodiments, the stimulating electrodes can be more proximate the organ than the recording electrodes.

Any number of electrodes on the probe can generally be in electrical communication with electrical circuitry for applying electrical signals (e.g., stimulation signals) stimulating electrodes or for receiving and/or processing signals from the electrodes. In some examples, circuitry can include various components, such as a processor and operational amplifier with capacitance control in electrical communication with an active recording electrode on the probe for processing received electrical signals. In some embodiments, the active electrode can possess high impedance. Additionally or alternatively, the active electrode can be a part of an active electrode circuit (e.g., an active electrode in communication with circuitry such as amplifier, processor, etc.), which can itself be configured to have a high input impedance. This design can block electrical noise generated by the various sources inherent to the intravascular space, such as blood flow or vascular muscular contraction from being amplified. In addition, such circuitry can limit the detection of nerve firing to a selective region within the vessel's wall. In some configurations, the amount of impedance and applied electrical signal can be dependent on the size and number of recording electrodes, as the interference effects are proportional to the total surface area of the electrode(s) used. In various embodiments, impedance loading can be positioned prior to an amplifier or can be incorporated into the amplifier design.

In some embodiments, the probe and electrical circuitry can be a part of a system for stimulating, monitoring, and destructing nervous tissue. In some such systems, the electrical circuitry can be a part of or otherwise in electrical communication with an electronic control unit (ECU). In various embodiments, the ECU can include a signal emitting portion and/or a signal receiving portions, and can be configured to emit electrical signals to and/or to receive electrical signals from the probe, respectively.

FIG. 13 is a system diagram of an example system for interfacing with a patient's arterial nerves. As shown, the system 1300 of FIG. 13 includes an ECU 1302 in electrical communication with a probe 1340 inserted in an artery 1350 of a patient. The ECU 1302 includes a stimulator 1306 having electrodes 1308 in electrical communication with stimulating electrodes 1342 on the probe 1340. The stimulator 1306 can emit electrical signals to the stimulating electrodes 1342 via electrodes 1308. When emitting a signal to the probe, the signal can have specific voltage, amperage, duration, and/or frequency of application that will cause nerve cell activation. In an example embodiment, the electrodes 1308 can include an anode and a cathode. Further, in some such embodiments, the cathode can be electrically coupled to a stimulating electrode 1342 that is located distally from a stimulating electrode 1342 that is electrically coupled to the anode. It will be appreciated that, in such an example, stimulating electrodes 1342 can similarly be referred to as the anode and cathode due to the respective electrical connection between stimulating electrodes 1342 and electrodes 1308. That is, electrodes 1342 may include an anode and a cathode based on functional operation associated with respectively connected electrodes 1308. Thus, in some examples, the probe 1340 includes an anode and a cathode for applying a stimulation signal to the arterial wall. In some such examples, the cathode can be located distally with respect to the anode. The nerve destruction block 1346 can be implemented, e.g., using any one of the RF ablation antenna described above with reference to FIG. 6, but is not limited thereto.

Upon receiving the signal, the stimulating electrodes of the probe can apply electrical energy to a patient's nerves through the arterial wall based on the received signal. The stimulus can have any of a variety of known waveforms, such as a sinusoid, a square wave form or a triangular wave form, as taught, for example, in the paper "Selective activation of peripheral nerve fiber groups of different diameter by triangular shaped stimulus pulses," by Accornero (Journal of Physiology. 1977 December; 273(3): 539-560). In various examples, the stimulation can be applied for durations between approximately 0.05 ms and approximately 2 ms. Such signals can be applied through a single, unipolar electrode or a bipolar electrode, for example, as described with regard to the various probe configurations of FIGS. 12A-12D. In some examples, stimulation signals can be applied via a bipolar electrode with "anodal blocking," as will be described below.

The probe 1340 includes recording electrodes 1344, in the illustrated embodiment positioned distally from stimulating electrodes 1342. The recording electrodes 1344 can be configured to detect electrical signals in the patient's nerves at a location separate from the stimulating electrodes 1342. For example, the recording electrodes 1344 can be used to detect an elicited potential caused by a stimulus from the stimulating electrodes 1342 and propagating toward the organ.

In some configurations, the stimulation of nerves to evoke an elicited potential can cause such a potential to propagate in every direction along the nerve fibers. In some situations, it can be undesirable for such a potential to propagate unnecessarily through the nerve for patient safety and/or desired signal isolation purposes. In some configurations, the propagation of elicited action potentials can be "blocked" by applying an electrical signal to a portion of the nerve. Accordingly, in some embodiments, a probe or additional component can include electrodes configured to reduce or eliminate an elicited potential from propagating undesirably. For example, with reference to FIG. 13, the probe 1340 can include a third stimulating electrode (not shown) further from the organ along the arterial wall than the first and second stimulating electrodes 1342. During the application of a stimulation signal, a blocking stimulation pulse can be applied via the third electrode to prevent elicited action potentials from travelling proximally along the patient's nerves while permitting the action potential to propagate toward the recording electrodes 1344.

In some embodiments, the ECU 1302 can digitally sample the signal on the recording electrode(s) 1344 to receive the electrical signal from the probe 1340. In alternate embodiments, the signal can be recorded as an analog signal. When receiving an electrical signal from the probe 1340, the ECU 1302 can perform filtering and/or other processing steps on the signal. Generally, such steps can be performed to discriminate the signal from the probe from any background noise within the patient's vasculature such that the resulting output is predominantly the signal from nerve cell activation. In some instances, the ECU 1302 can modulate the electrical impedance of the signal receiving portion in order to accommodate the electrical properties and spatial separation of the electrodes mounted on the probe in a manner to achieve the highest fidelity, selectively and resolution for the signal received. For example, electrode size, separation, and conductivity properties can impact the field strength at the electrode/tissue interface.

Additionally or alternatively, the ECU 1302 can comprise a headstage (e.g., a preamplifier) and/or another amplifier to perform any of offsetting, filtering, and/or amplifying the signal received from the probe. In some examples, a headstage applies a DC offset to the signal and performs a filtering step. In some such systems, the filtering can comprise applying notch and/or band-pass filters to suppress particular undesired signals having a particular frequency content or to let pass desired signals having a particular frequency content. An amplifier can be used to amplify the entire signal uniformly or can be used to amplify certain portions of the signal more than others. For example, in some configurations, the amplifier can be configured to provide an adjustable capacitance of the recording electrode, changing the frequency dependence of signal pick-up and amplification. In some embodiments, properties of the amplifier, such as capacitance, can be adjusted to change amplification properties, such as the resonant frequency, of the amplifier.

In the illustrated embodiment of FIG. 13, the ECU 1302 includes an amplifier 1312 in communication with the recording electrodes 1344 of the probe 1340 in order to receive electrical signals therefrom. The amplifier 1312 can include any appropriate amplifier for amplifying desired signals or attenuating undesired signals. In some examples, the amplifier has a high common-mode rejection ratio (CMRR) for eliminating or substantially attenuating undesired signals present in each of the recording electrodes 1344. In the illustrated embodiment, the amplifier 1312 is electrically coupled to tissue 1360 of the patient for providing a reference signal to the amplifier. In some embodiments, amplifier 1312 can be adjusted as described above, for example, via an adjustable capacitance or other attributes of the amplifier.

In the example system 1300 of FIG. 13, the ECU 1302 further includes a filter 1314 for enhancing the desired signal in the signal received from recording electrodes 1344. As described, the filter 1314 can include a band-pass filter, a notch filter, or any other appropriate filter to isolate desired signals from the received signals. Similar to the amplifier 1312 discussed above, in some embodiments, various properties of the filter 1314 can be adjusted to manipulate its filtering characteristics. For example, the filter may include an adjustable capacitance or other parameter to adjust its frequency response.

At least one of amplification and filtering of the signal received at the recording electrodes 1344 can allow for extraction of the desired signal at 1316. In some embodiments, extraction 1316 comprises at least one additional processing step to isolate desired signals from the signal received at recording electrodes 1344, such as preparing the signal for output at 1318. In some embodiments, the functionalities of any combination of amplifier 1312, filter 1314, and extraction 1316 may be combined into a single entity. For instance, the amplifier 1312 may act to filter undesired frequency content from the signal without requiring additional filtering at a separate filter.

In some embodiments, the ECU 1302 can record emitted stimuli and/or received signals. Such data can be subsequently stored in permanent or temporary memory 1320. The ECU 1302 can comprise such memory 1320 or can otherwise be in communication with external memory (not shown). Thus, the ECU 1302 can be configured to emit stimulus pulses to electrodes of the probe, record such pulses in a memory, receive signals from the probe, and also record such received signal data. While shown in FIG. 13 as being a part of the processor, it will be appreciated that the memory in or associated with the ECU 1302 can be internal or external to any part of the ECU 1302 or the ECU 1302 itself.

The ECU 1302 or separate external processor can further perform calculations on the stored data to determine characteristics of signals either emitted or received via the probe. For example, in various embodiments, the ECU 1302 can determine any of the amplitude, duration, or timing of occurrence of the received or emitted signals. The ECU 1302 can further determine the relationship between the received signal and the emitted stimulus signal, such as a temporal relationship therebetween. In some embodiments, the ECU 1302 performs signal averaging on the signal data received from the probe. Such averaging can act to reduce random temporal noise in the data while strengthening the data corresponding to any elicited potentials received by the probe. An example data collection procedure is outlined below:

1. Generate a stimulus pulse
2. Sample or record data from the receiving over a time period of interest; stop sampling or recording after period of interest (e.g., after any elicited potential might be detected)
3. Repeat steps 1 and 2; add the resulting samples to those already sampled
4. Repeat steps 1 through 3 as needed Averaging as such can result in a signal in which temporally random noise is generally averaged out and the signal present in each recorded data set, such as elicited potentials, will remain high. In some embodiments, each iteration of the process can include a synchronization step so that each acquired data set can be temporally registered to facilitate averaging the data. That is, events that occur consistently at the same time during each iteration may be detected, while temporally random artifacts (e.g., noise) can be reduced. In general, the signal to noise ratio resulting in such averaging will improve by the square root of the number of samples averaged in order to create the averaged data set.

The ECU 1302 can further present information regarding any or all of the applied stimulus, the signal, and the results of any calculations to a user of the system, e.g., via output 1318. For example, the ECU 1302 can generate a graphical display providing one or more graphs of signal strength vs. time representing the stimulus and/or the received signal. FIG. 9, discussed above, is an example plot of signal strength vs. time illustrating a stimulus signal (shown at the top in FIG. 9) and an associated elicited potential (shown at the bottom in FIG. 9). Time stamp 0 is indicative of the triggering of the stimulus signal, while time stamp 1 represents the onset of the elicited potential. In alternative embodiments, the ECU 1302 can present information representative of such signals to the user via an audio alert or any other appropriate method of communication.

In some embodiments, the ECU 1302 can include a controller 1322 in communication with one or both of stimulator 1306 and signal processor 1310. The controller 1322 can be configured to cause stimulator 1306 to apply a stimulation signal to the probe 1340. Additionally or alternatively, the controller 1322 can be configured to analyze signals received and/or output by the signal processor 1310. In some embodiments, the controller 1322 can act to control the timing of applying the stimulation signal from stimulator 1306 and the timing of receiving signals by the signal processor 1310.

Example electrical control units have been described. In various embodiments, the ECU 1302 can emit stimulus pulses to the probe, receive signals from the probe, perform calculations on the emitted and/or received signals, and present the signals and/or results of such calculations to a user. In some embodiments, the ECU 1302 can comprise separate modules for emitting, receiving, calculating, and providing results of calculations. Additionally or alternatively, the functionality of controller 1322 can be integrated into the ECU 1302 as shown, or can be separate from and in communication with the ECU.

In some embodiments, the ECU 1302 can include a switching network configured to interchange which of electrodes 1342, 1344 of the probe are coupled to which portions of the ECU. For instance, in some examples, the ECU 1302 as shown in FIG. 13 can be adjusted so that the stimulator 1306 is in electrical communication with electrodes 1344 of the probe and the signal processor 1310 is in electrical communication with electrodes 1342 of the probe. Additionally or alternatively, the ECU 1302 includes inputs for receiving connectors electrically coupling the ECU 1302 to the electrodes (1342, 1344) of the probe 1340. In some such embodiments, a user can manually switch which inputs receive connections to which electrodes of the probe 1340. Such configurability allows for a system operator to adjust the direction of propagation of the elicited potential as desired.

Figure 14:
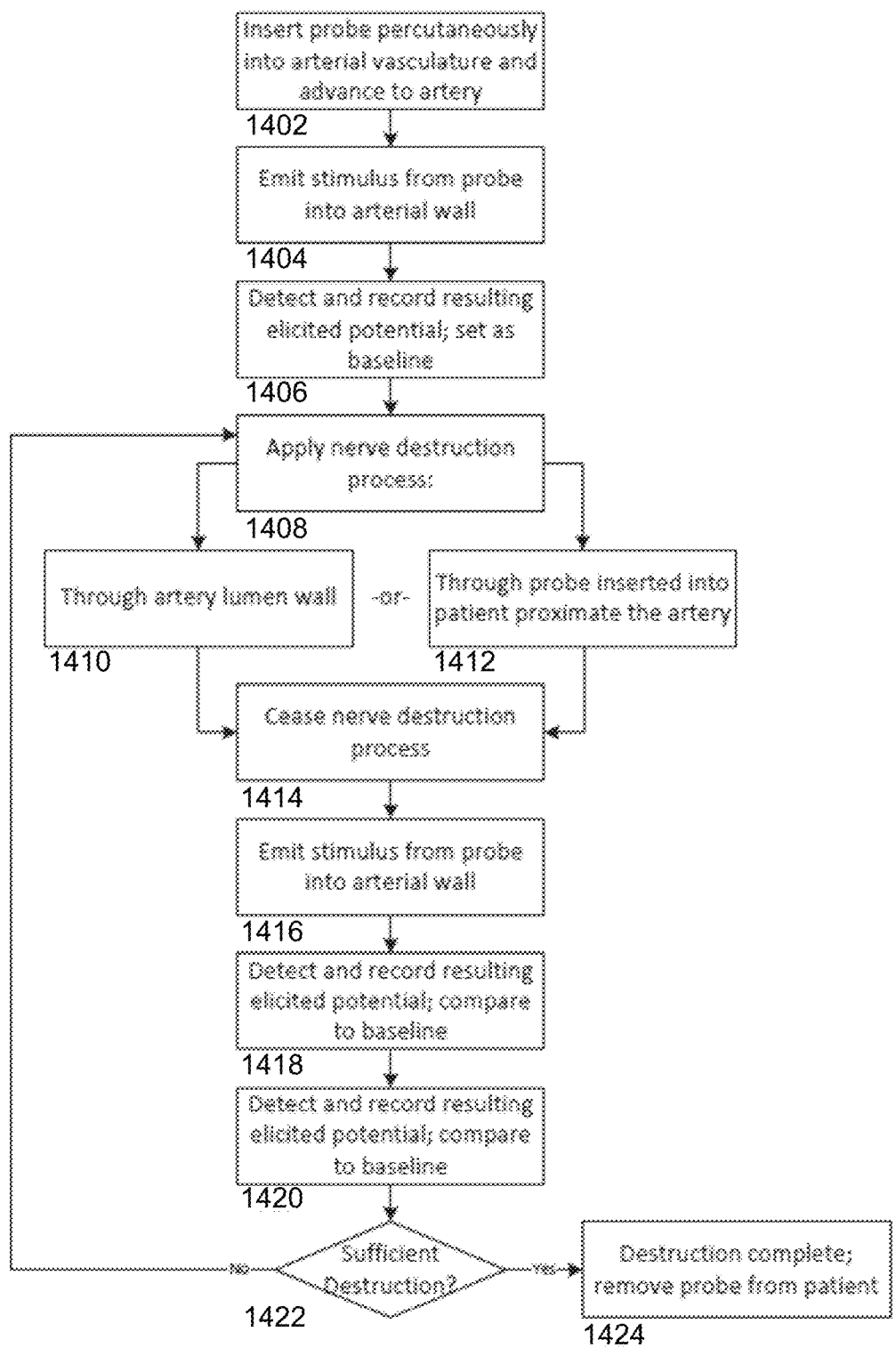
FIG. 14 is a process-flow diagram illustrating an example nerve analysis and destruction process.

Some aspects of the invention include methods of using systems such as those described above. An example method is illustrated in FIG. 14. During use, according to some embodiments, a probe is inserted percutaneously into the arterial vasculature and advanced into an artery (1402) such that the electrodes are placed in contact with the arterial lumen wall. Any appropriate probe can be used, such as example probes described above, or the probes described below (e.g., with reference to FIGS. 15, 17A, 17B, and 19). Additionally, while the method of FIG. 14 is generally directed toward interfacing with an arterial wall, similar methods can be employed in other blood vessels. A stimulus can be emitted into the arterial lumen wall via the probe (1404), and the resulting signal (e.g., elicited signal or action potential) can be detected via the probe and recorded to the ECU. Such a measurement can be set as a baseline measurement (1406), since no destruction to the nerves has yet been applied. The recorded baseline signal can be stored in a memory in the system.

After recording a baseline measurement, a nerve destruction process can be applied (1408) to the nerves within or proximate the artery. Among various embodiments, the nerve destruction means can be applied (i) through the artery lumen wall (1410) (e.g., for the purposes of terminating nerve activity) or (ii) through a probe inserted into the patient's abdomen to a position in proximity to the artery (1412) (e.g., for the purposes of terminating nerve activity). The destruction process can be ceased (1414) after an amount of time, and a stimulus can once again be emitted via the probe (1416) and the resulting elicited signal can be detected (1418) via the probe.

The detected and recorded elicited signal can be stored in memory and/or compared to the baseline signal (1420) previously stored. Based on the comparison, a relative amount of nerve destruction performed by the destructive means can be determined. In some embodiments, the comparison is calculated automatically and a relative amount of destruction is communicated to a user. A user can then determine (1422) whether additional destruction is appropriate, or if sufficient destruction has been performed. Alternatively, in some configurations, the determination can be automated. That is, if the controller 1322 (as a part of or separate from the ECU 1302) can determine whether or not a sufficient amount of destruction has been performed based on an automated comparison. For example, the controller 1322 can determine if the comparison satisfies a predetermined condition, the predetermined condition indicating a sufficient amount of destruction has been performed.

Satisfying the predetermined condition can include, in various examples, a reduction of the magnitude of the elicited potential by a predetermined percentage or absolute amount, or a complete elimination of the elicited potential. In such automated embodiments, if it is determined (1422) that insufficient destruction has taken place (e.g., the predetermined condition is not met), the controller 1322 can cause the destructive means to perform additional destructive processes (1408) to the patient's nerves. In other embodiments, a user can manually apply additional destructive processes (1408) of insufficient destruction is detected. If sufficient destruction has been performed (e.g., the predetermined condition is met), then the destruction process is complete (1424).

In general, this process can be repeated (aside from reacquiring a baseline measurement) until it has been determined that sufficient destruction has been performed. That is, when nerve activity is reduced to an acceptable level. Then, the process is terminated and the probe can be withdrawn from the patient's body (1424). FIGS. 10A-10C, previously discussed above, show the progression of elicited potentials in arterial nerves in response to a stimulus pulse as the relative amount of nerve destruction increases. FIG. 10A is a plot showing a stimulus signal 1000a and a detected elicited response 1002a before performing a destructive operation on the arterial nerves. In some examples, FIG. 10A can represent a baseline measurement. FIG. 10B illustrates a stimulus signal 1000b and a detected elicited response 1002b. As can be seen, the elicited response 1002b is significantly smaller than elicited baseline response 1002a, indicating that significant destruction of arterial nerves has been performed. FIG. 10C illustrates a stimulus signal 1000c and a detected elicited response 1002c after still more arterial nerve destruction has been performed. As can be seen, the elicited response 1002c is much smaller than that of either the elicited baseline response 1002a or the response 1002b, and is almost non-existent. This implies that further, or possibly complete, arterial nerve destruction has taken place.

During such stimulating, detecting, and destruction procedures, many factors can be considered and/or manipulated to improve system performance. Several factors can be manipulated or taken into account while stimulating nerves to elicit a response, including:

(a) Stimulus Strength—In general, the stimulus must be of a sufficient strength (voltage) to induce an elicited potential. In some embodiments, the stimulus can be of sufficient strength such that most of the nerves along the artery are stimulated. In some situations, such as with the renal artery, many nerves are known to run along the outside of the artery, which may require a stimulus from a probe inside the artery to be sufficiently large for eliciting action potentials in the nerves. In some examples, probes can be configured to provide stimulus signals based on a desired level of current (e.g., in a constant current mode of operation), for example, between approximately 1 mA and approximately 25 mA, while providing whatever voltage is necessary for such currents, in some cases up to or above 100 V. In other examples, stimulations are based only on a desired voltage (e.g., in a constant voltage mode of operation), such as approximately 1 V, or range of voltages, such as between 0.1 V and 1 V, between 1 V and 10 V, etc.

(b) Electrode Separation—In general, for any given voltage, the closer the electrodes are, the stronger the resulting electric field gradient. However, electrodes spaced too close together can result in a short circuit along the tissue itself such that the current is shunted and a voltage gradient is not allowed to develop. In some embodiments, electrodes are separated by approximately 1-3 mm. In some examples, electrode spacing can be designed based on expected action potential magnitude, duration, and/or propagation velocity.

(c) Pulse Width—To elicit such potentials, the pulse often will be applied for a sufficient duration such that the voltage gradient developed by the stimulus pulse has enough time to effect an action (elicited) potential, but not so long as keep the nerves in a constant state of depolarization. In some embodiments, pulse widths can be between 50 to 100 μs; in other systems, pulse widths of approximately 1-10 ms can be used.

(d) Frequency—Finally, the frequency or repetition rate of the stimulus needs to be considered. In some embodiments, a frequency that is too fast can exhaust the nerve while a frequency that is too slow can unnecessarily delay the process. In various embodiments, frequencies within approximately 5-40 Hz can be used.

In addition to considerations of the nerve stimulation pulses, some parameters of the system are configured to maximally elicit bursts of autonomic activity via electrodes placed within the arterial lumen, as well as to enable sufficient detection of autonomic activity. For example, in some embodiments, parameters such as stimulation type, delivery fashion, pulse frequency, pulse duration, phase duration, current intensity, pulse period and pulse train of the electrical stimulation can be selected to have a maximum effect on eliciting autonomic neural activity and be amenable to recording the elicit bursts nearby. In some examples, electrodes can be spaced apart and/or sized according to applied stimulation signals in order to maximize the effect of the applied stimulation. For example, the electrodes can be spaced according to the propagation velocity and/or stimulation pulse width so that the entire duration of a desired pulse shape is used for stimulation purposes between the anode and the cathode.

Further, in some embodiments, various aspects of recording electrodes can be configured to better receive or distinguish elicited potential. For example, in some embodiments, the size of the recording electrodes can be selected based on at least one of the propagation velocity of elicited potentials in the patient's nerves and the pulse width of the elicited potentials. In some embodiments, the recording electrodes have a width that is approximately the same as the pulse width of the elicited potential. In further embodiments, the recording electrodes have a width that is smaller than the pulse width of the elicited potential. In general, a narrow electrode can minimize the amount of noise present at the surface of electrode simultaneously with the elicited potential.

As previously discussed, elicited potentials in autonomic nerves are generally small and are often difficult to detect. Further, the position of autonomic nerves proximate an arterial lumen can make detection of elicited potentials from within the artery difficult. For example, renal nerves encircle the renal artery and lie proximate to the renal artery. As such, detection of elicited potentials by an indwelling probe is made difficult both by the barrier presented by the arterial wall itself as well as the distance from the sensing electrodes to the nerves. Thus, it is important to be able to both detect and distinguish such signals from other noise in the patient and system.

One process to enhance the detection of elicited potentials involves expecting any such potentials to be present at a certain time. That is, a known action potential propagation/conduction velocity and electrode spacing allows for creating a temporal window in which the elicited potential can be predicted to arrive at the recording electrode. Accordingly, methods according to the present invention can include receiving elicited signals via the probe within a predetermined time window. For example, with respect to FIGS. 10A-10C, numeral 0 represents the time at which the stimulus potential is applied, while numerals 1 and 2 represent the start and end times in which an elicited potential is expected based on the electrode spacing and the elicited potential propagation velocity. As shown, the detection elicited potentials are generally present within the defined temporal window. Detecting nerve signals within only a predefined temporal window can help prevent the system from receiving noise or other artifacts not associated with elicited potentials and falsely relating them to such potentials.

Additionally or alternatively, various steps can be employed to isolate the detection of elicited potentials from detection of the stimulation signal at the recording electrodes. In general, the stimulation pulse will reach the recording electrodes before the elicited potential arrives. This is because the elicited potential propagates by a different mechanism than the stimulation pulse. While the stimulation pulse propagates toward the recording electrodes due to electrical conduction through body tissues and fluids, elicited potentials propagate along axons via a sequential cell membrane process. Such propagation occurs having a velocity between approximately 0.2 m/s and approximately 200 m/s, which is comparatively slower than the stimulation pulse. Thus, in some instances, the recording electrodes can be blanked for a period of time following the application of the simulation pulse, allowing the stimulation pulse to effectively pass by the recording electrodes without being recorded. Monitoring by the recording electrodes can be resumed after blanking in time to receive the elicited potential following the stimulation pulse.

In some embodiments, the probe can be configured to allow for a maximum separation between the simulating electrode(s) and the recording electrode(s). Such a configuration results in a greater temporal separation of the stimulation pulse and the elicited potential at the recording electrodes when compared to more closely-spaced electrodes. In some examples, the practical distance between the stimulating electrode(s) and the recording electrode(s) is limited by the length of the artery in which the probe is inserted for operation. Thus, in some embodiments, the probe comprises an adjustable distance between the stimulating electrode(s) and the recording electrode(s) in order to allow for the distance between the sets of electrodes to be maximized while allowing the probe to adequately fit within the artery of the patient.

Figure 15:
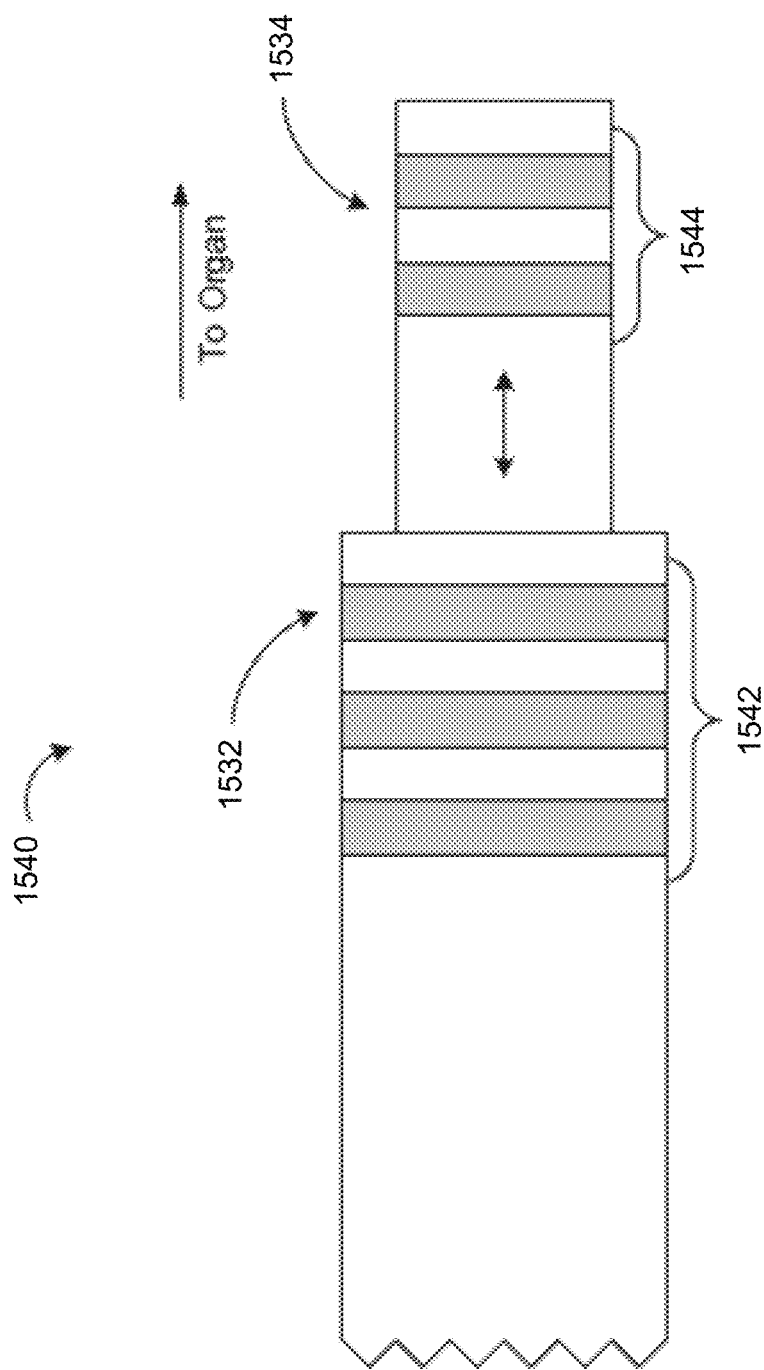
FIG. 15 is an example probe design for inserting into a patient's artery.

FIG. 15 is an example probe configured for adjustable separation of the stimulating and recording electrode(s). As shown, stimulating electrodes 1542 are present on a first portion 1532 of the probe 1540, while recording electrodes 1544 are present on a second portion 1534 of the probe 1540. In the illustrated embodiment, the second portion 1534 is located distally from the first portion 1532 in a patient's artery, for example, toward an organ. The second portion 1534 can be configured to translate relative to first portion 1532, allowing for the adjustment of the probe length and the separation between the stimulation 1542 and recording 1544 electrodes. In some examples, translation of the second portion 1534 relative to the first portion 1532 is achieved by a telescoping configuration between the first 1532 and second 1534 portions of the probe 1540.

As generally discussed previously, various processing steps can be performed by an ECU or other processor to further distinguish elicited potentials from other signals. As shown in the schematic diagram in FIG. 13, the ECU can include a signal processor comprising an amplifier, filter, and other signal extraction tools. The amplifier can comprise a common-mode rejection amplifier in order to emphasize an elicited signal over the background noise of the artery. In some embodiments, the amplifier comprises a common-mode rejection ratio (CMRR) of approximately 100 dB or more. A band-pass filter can be used to attenuate signals not within an expected frequency band indicative of elicited potentials. Additionally or alternatively, a band-reject filter can be used to specifically attenuate expected noise at an expected frequency. For example, a band-reject filter centered around approximately 60 Hz might be used. Various other signal processing and extraction techniques can similarly be employed, such as the averaging processes herein described.

In some embodiments, various characteristics (e.g., capacitance, resistance, etc.) of components such as the electrodes, circuitry, or parts of the ECU 1302, such as an amplifier or filter, can be adjusted either automatically (e.g., via software without requiring user-intervention or user-programming) or manually. For example, in some systems, the capacitance of a filter or amplifier can be adjusted to tune bandwidths or resonant frequencies of such components to better extract signals representative of elicited potentials. In some processes, a user or controller 1322 can adjust such values and observe the response to such adjustments in order to optimize system operation. That is, in some embodiments, such values are manually adjustable, and a user can adjust such values while observing signal detection performance. In some situations, specific probe types have known properties that affect the stimulation or detection of elicited potentials in the patient. Accordingly, in some embodiments, the ECU 1302 can detect or receive a "probe type" input and automatically adjust the capacitance and/or resistance accordingly to allow for enhanced stimulation or amplification and detection of elicited potential. In various embodiments, the "probe type" input can be entered manually, or the system can automatically detect the probe type.

Figure 16:
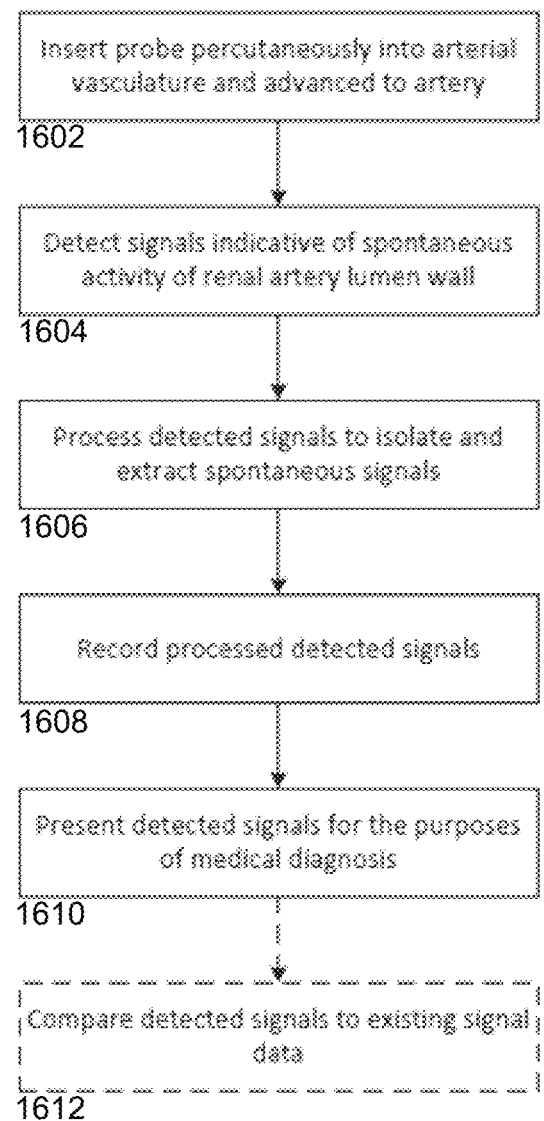
FIG. 16 is a process-flow diagram illustrating an example diagnostic process.

In some embodiments, systems such as those herein described can be utilized for diagnostic purposes. In an example procedure, such as illustrated in FIG. 16, a probe such as those herein described can be inserted into the vasculature of a patient. In various embodiments, the probe is inserted percutaneously, and further can be advanced into an artery (1602). The probe can be used to detect signals in the arterial wall indicative of spontaneous or native activity of nerves from within the wall (1604), for example, electrical signals. Such detected signals can be processed in order to isolate and extract the desired spontaneous signals (1606). Processing can include averaging to eliminate temporal noise, filtering the signal to amplify or to attenuate various frequency bands, or any other processing described herein or otherwise known in the art.

The processed signals can be recorded (1608), for example in a temporary or permanent memory, and presented to a user for the purposes of medical diagnosis. Signals can be presented (1610), for example, as a plot of signal vs. time on a display. Additionally or alternatively, the signals can be compared to existing signal data (1612) for comparing the patient's spontaneous nerve activity to a baseline. In some examples, the patient's spontaneous nerve activity can be compared to that of a healthy patient to assess organ or nervous health. Such a comparison can provide indication as to whether or not ablation may be an effective treatment for the particular patient. In other examples, the spontaneous nervous activity can be analyzed independently from any previously recorded nervous activity to determine the health of the patient's proximate nerves or the viability of nerve treatments on the patient.

An example display is shown in FIG. 7, previously discussed above, in which the signal is plotted against time, showing extracted spontaneous nerve activity proximate the artery containing the probe. Comparisons between detected nerve activity and a baseline nerve activity stored in memory can provide indications for possible next steps to be performed. For instance, in some examples, if a patient displays little or no spontaneous nerve activity, a clinician may determine that a nerve destruction process is not likely to significantly affect the patient, and may explore alternative treatment options. In other instances, if a patient exhibiting high levels of abnormal nerve activity, a clinician may determine that the patient may benefit from a nerve destruction process. As such, the diagnostic use of the probe recording electrodes can allow for the execution of an informed treatment plan rather than the arbitrary destruction of nerve function. Subsequently, if nerve destruction is desired, operations such as those described above, for example as in FIG. 14, can be carried out using the system.

Figure 17A:
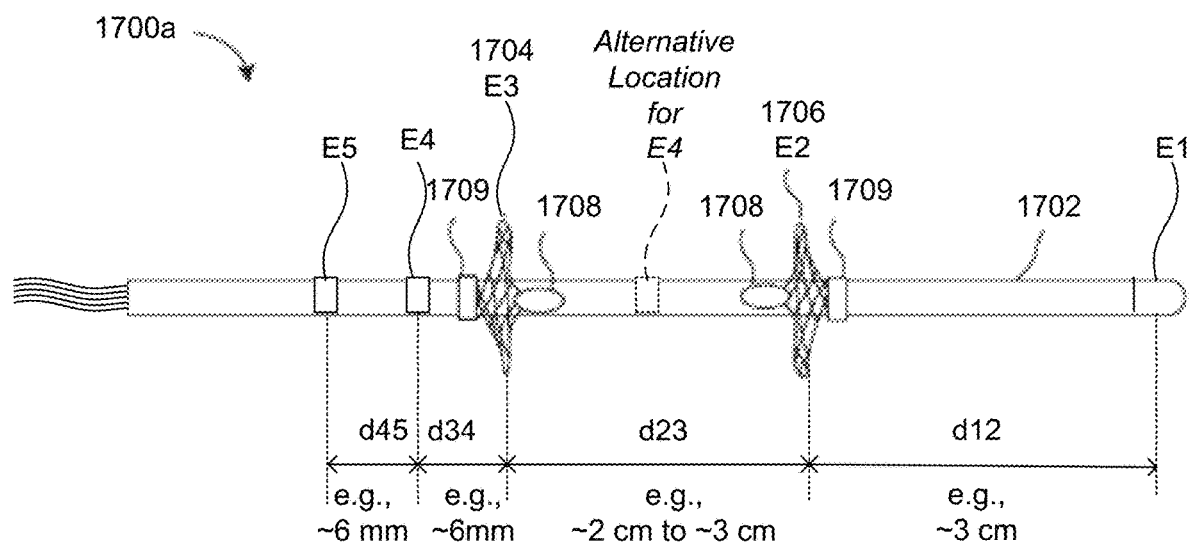
FIG. 17A illustrates an intraluminal microneurography probe according to a specific embodiment of the present technology.

FIG. 17A illustrates an intraluminal microneurography probe according to a specific embodiment of the present technology, wherein a probe assembly is shown generally at 1700a. The probe assembly 1700a can be more succinctly referred to as a probe 1700a. Here, a probe body is shown at 1702, having mesh electrodes 1704 and 1706 affixed thereto at attachment points 1708. The mesh electrode 1704 can also be referred to as the electrode E3, and the mesh electrode 1706 can also be referred as the electrode E4. More specifically, the probe assembly 1700a is shown as including electrodes E1, E2, E3, E4, and E5. Similar to the embodiment described above with reference to FIG. 2, each of the mesh electrodes E3 and E4 also has a respective sliding collar element 1709 located at the end of the mesh electrode opposite attachment point 1708. This sliding collar 1709 when moved toward the attachment point 1708 causes the mesh electrode to expand around the probe body 1702, or from an internal channel of the probe body 1702. In FIG. 17, the mesh electrodes E2 and E3 are shown as being expanded, or more generally, deployed, such that the mesh electrodes E2 and E3 can provide electrical contact with an artery wall. The mesh electrodes E2 and E3 when non-expanded, or more generally, not deployed, can look similar to the mesh electrodes 206 and 204 shown in and described above with reference to FIG. 2. More specifically, when the mesh electrodes E2 and E3 are in their non-deployed positions, they can confirm to an outer surface of the probe body 1702, or alternatively, they can be retained within one or more inner cavities of the probe body 1702 when they are in their non-deployed positions.

The probe body 1702 is configured to be inserted into an artery when the mesh electrodes E2 and E3 are not deployed, i.e., in their non-deployed positions. Then, after the probe body 1702 has been inserted into an artery, the mesh electrodes E2 and E3 can be deployed such that they contact the artery walls, without blocking blood flow through the artery. In accordance with certain embodiments, the mesh electrodes E2 and E3 are configured to be simultaneously in their non-deployed or deployed positions. In other embodiments, the mesh electrodes E2 and E3 are individually deployable, such that one of the mesh electrodes can be in its deployed position while the other one of the mesh electrodes is in its non-deployed position. It would also be possible to have both of the mesh electrodes E2 and E3 in their non-deployed positions, or to have both of the mesh electrodes E2 and E3 in their deployed positions.

Still referring to FIG. 17, the electrode E1, which is the most distal electrode, can be a tip electrode or a band electrode located at or in close proximity to the most distal end of the probe body 1702. A band electrode can also be referred to as a ring electrode. The electrode E2, which in this embodiment is a deployable mesh electrode (aka the mesh electrode 1706), is the electrode that is closest to the electrode E1, with the center-to-center axial distance between the electrodes E1 and E2 (when the electrode E2 is deployed) being referred to as the distance d12. In accordance with certain embodiment, the distance d12 is within the range of 1 cm to 6 cm (which distance d12 should be selected such that an electrical field strength of the stimulus is sufficient to evoke a neural response in nerves that surround the biological lumen), with d12 preferably being about 3 cm. The center-to-center axial distance between the two mesh electrodes E2 and E3 (aka the mesh electrodes 1706 and 1704), when they are both deployed, can be referred to as the distance d23. In accordance with certain embodiments, the distance d23 is within the range of 1 cm to 10 cm (which distance should be selected such that the evoked action potential of the neural response do not reach the electrode E3 until any stimulus artifact effect has subsided), with the d23 distance preferably being about 3 cm. The center-to-center axial distance between the electrodes E3 and E4 can be referred to as the distance d34. In accordance with certain embodiments, the distance d34 is within the range of 2.5 mm cm to 25 mm (i.e., 0.25 cm to 2.5 cm), (which distance should be selected such that it is at least as great a distance from the contact of the electrode with the lumen wall and to the nerve of interest furthest from the lumen wall), with the distance d3 preferably being about 6 mm. The center-to-center axial distance between the electrodes E4 and E5 can be referred to as the distance d45. In accordance with certain embodiments, the distance d45 is within the range of 2.5 mm to 25 mm (i.e., 0.25 cm to 2.5 cm), with the distance d3 preferably being about 6 mm. The term "about" as used herein, when used to refer to a distance or other value, means plus/minus 10% of the specified distance or other value. While the deployable electrodes E2 and E3 in FIG. 17 are show as being mesh electrodes, the deployable electrodes E2 and E3 can alternatively be helical electrodes, similar to the deployable helical electrodes 106 and 104 in FIG. 1. Alternatively, the deployable electrodes E2 and/or E3 can be deployable basket electrodes, but are not limited thereto. The aforementioned deployable electrodes can be made from one or more wires, or can be made from an electrically conductive tube (e.g., made of nitinol, or some other alloy or metal) having a laser cut pattern. Other variations are also possible and within the scope of the embodiments describe herein. In accordance with certain embodiment, the axial width of each of the band electrodes E1, E4, and E5 is about 1 mm. However, narrower and wider widths for the band electrodes are also possible and within the scope of the embodiments described herein.

The probe assembly 1700a can be used for sensing nerve activity, as well as for stimulating nerves to attempt to evoke a nerve response. More specifically, in accordance with certain embodiments, the electrodes E1 and E2 are used for stimulating nerves to evoke a nerve response, with the electrode E1 serving as the stimulation anode and the deployable electrode E2 serving as the stimulation cathode, wherein such nerve stimulation can be referred to more specifically as bi-polar nerve stimulation. In accordance with certain embodiments, the electrodes E3, E4, and E5 are used for sensing nerve activity, with the deployable electrode E3 serving as the active electrode (aka the sense electrode or the sense cathode), the electrode E4 serving as the common electrode (aka the reference ground electrode), and the electrode E5 serving as the return electrode (aka the sense anode). In order for the electrodes E3 and E5 to serve as active and return electrodes, respectively, the electrodes E3 and E5 are connected to non-inverting (+) and inverting (−) terminals of a sense amplifier (which can be pre-amplifier) that is used for sensing nerve activity. In order for the electrode E4 to serve as the common electrode when performing nerve sensing, the electrode E4 is connected to the reference ground terminal of the sense amplifier (e.g., 1812 in FIG. 18) that is used for sensing nerve activity. In such a configuration, the common electrode E4 serves as the reference voltage for the sensed electrical signal that is indicative of nerve activity, i.e., as the body ground, so that the sense amplifier is referenced to the electrical environment of the sense electrodes. The aforementioned evoked nerve response can also be referred to as an evoked neural response, or more generally, as an evoked potential.

Each of the aforementioned electrodes E1, E2, E3, E4, and E5 can be connected to a separate wire that passes through one or more internal channels of the probe body 1702. For example, all or some of the wires that are connected to individual ones of the electrodes can pass through a common chamber, or there can be a separate chamber for each wire or subsets of wires. The wires that are connected at their distal ends to the electrodes E1 and E2, which are used for delivering nerve stimulation, are connected at their proximal ends to a stimulator (e.g., 1806 in FIG. 18), which is used to generate the stimulation signals that are delivered via the electrodes E1 and E2 and used to attempt to provide an evoked nerve response. It is noted that where nerves have already been destroyed, e.g., via ablation, such nerves will not respond to being stimulated, i.e., their evoked response will be no or substantially no neural activity. The wires that are connected at their distal ends to the electrodes E3 and E5, respectively, are connected at their proximal ends to the non-inverting (+) and inverting (−) terminals of a sense amplifier (e.g., 1812 in FIG. 18) that is used for sensing nerve activity. The wire that is connected at its distal end to the common electrode E4 is connected at its proximal end to the reference ground terminal of the sense amplifier (e.g., 1812 in FIG. 18). In FIG. 17, the electrodes E2 and E3 that are configured to be moved between non-deployed and deployed positions are shown as being mesh electrodes, the same as or similar to the mesh electrodes 206 and 204 introduced above in the discussion of FIG. 2. Alternatively, the electrodes E2 and E3 that are configured to be moved between non-deployed and deployed positions can be helical electrodes that are the same as or similar to the helical electrodes 106 and 104 introduced above in the discussion of FIG. 1. Alternatively, the electrodes E2 and E3 that are configured to be moved between non-deployed and deployed positions can be deployable basket electrodes, but are not limited thereto. The aforementioned deployable electrodes can be made from one or more wires, or can be made from an electrically conductive tube (e.g., made of nitinol, or some other alloy or metal) having a laser cut pattern. Other variations are also possible and within the scope of the embodiments describe herein. When a deployable electrode is in its deployed position it can also be said to be in its expanded position. When a deployable electrode is in its non-deployed position it can also be set to be in its non-expanded position.

In certain alternative embodiments, instead of having the common electrode E4 between the deployable electrode E3 and the band electrode E5, the common electrode E4 can instead be located between the deployable electrodes E2 and E3 (e.g., about midway between the electrodes E2 and E3 when they are deployed), as shown in dotted line in FIG. 17A. In a specific implementation, a switching circuit within the probe assembly (or external to the probe assembly) can enable a user to select between a first configuration that utilizes the electrodes E1 and E2 for performing nerve stimulation and utilizes the electrodes E3, E4, and E5 for sensing nerve activity, and a second configuration that utilizes the electrodes E3 and E5 for performing nerve stimulation and utilizes the electrodes E1, E2, and E4 for sensing nerve activity. In such alternative embodiments, a center-to-center axial distance d12 between the electrodes E1 and E2 is preferably about the same as the center-to-center axial distance d35 between the electrodes E3 and E5.

In the embodiments described above, the center-to-center axial distance between the electrodes E1 and E2 that are used for delivering nerve stimulation are about an order of magnitude or more greater than the center-to-center axial distance between each adjacent pair of the electrodes E3, E4, and E5 that are used for sensing nerve activity. The relatively larger distance between the stimulating electrodes E1 and E2 is beneficial because there is a desire to recruit a relatively large number of nerves when delivering nerve stimulation for the purpose of evoking a neural response. On the other hand, the relatively smaller distance between the electrodes E3 and E5 is desirable because there is a desire to have a relatively small sensing aperture when sensing specific nerve activity of interest (e.g., renal nerve activity), so that the sensed signal does not include (or minimally includes) nerve activity that is not of interest (such as nerve activity from nearby arteries that are not being analyze or are otherwise not of interest).

Embodiments of the present technology can be used to analyze the neural activity (and potentially perform denervation) of various different types of nerves, including, but not limited to, renal nerves that are proximate the renal artery. The renal nerves, which are classified as C-fibers, are unmyelinated nerve fibers that have an action potential propagation velocity in the range of about 0.2 to 2.0 meters per second (m/s), which can also be expressed as about 0.2 to 2.0 millimeters per millisecond (mm/ms). The extracellular voltage produced by the nerve action potential of renal nerves are on the order of microvolts (μV), and thus, due to their low magnitude are difficult to detect. The renal nerves associated with the kidney, which is connected to the renal artery, run within the renal artery wall and the tunica adventitia, a distance of up to 10 mm from the luminal wall of the artery. In the embodiment introduced with reference to FIG. 17A, an outer periphery of each of the electrodes E2 and E3 of the probe assembly, when the electrodes E2 and E3 are in their deployed positions, are configured to contact the luminal wall of an artery, such as the renal artery.

The electrodes E1-E5 of the probe assembly 1702 provide for two subsystems, including a nerve activity sensing subsystem, and a nerve stimulation subsystem, as can be appreciated from the above discussion of FIG. 17A. The electrodes E1 and E2 provide the anode and the cathode, respectively, of a nerve stimulation circuit (STIM) and the remaining three electrodes E3, E4, and E5 form part of a nerve activity (action potential) sensing circuit (SENS). The SENS circuit should be able to detect the voltage signature of the action potential within the spectrum of bioelectrical activity within the human body. In a specific embodiment, the electrodes on the distal portion of the probe body 1702, namely the electrodes E1 and E2, are part of the STIM circuit, and the more proximate electrodes E3, E4, and E5 are part of the SENS circuit. In accordance with an embodiment, the electrode E3 is connected to the non-inverting (+) input terminal of an amplifier (e.g., 1812 in FIG. 18), the electrode E5 is connected to the inverting (−) input terminal of the amplifier, and the electrode E4 is connected to the reference or ground terminal of the amplifier, which can also be referred to as the reference ground terminal. This can be appreciated from FIG. 18, described below.

The aforementioned STIM circuit creates a short duration electric field with the objective of initiating an action potential with the nerve(s) being stimulated. The depth and intensity of the electric field is affected by the separation between cathode and anode electrodes (E2 and E1). In accordance with certain embodiments, an objective is to evoke action potentials out to a distance (i.e., depth) of about 10 mm beyond the arterial wall.

Figure 18:
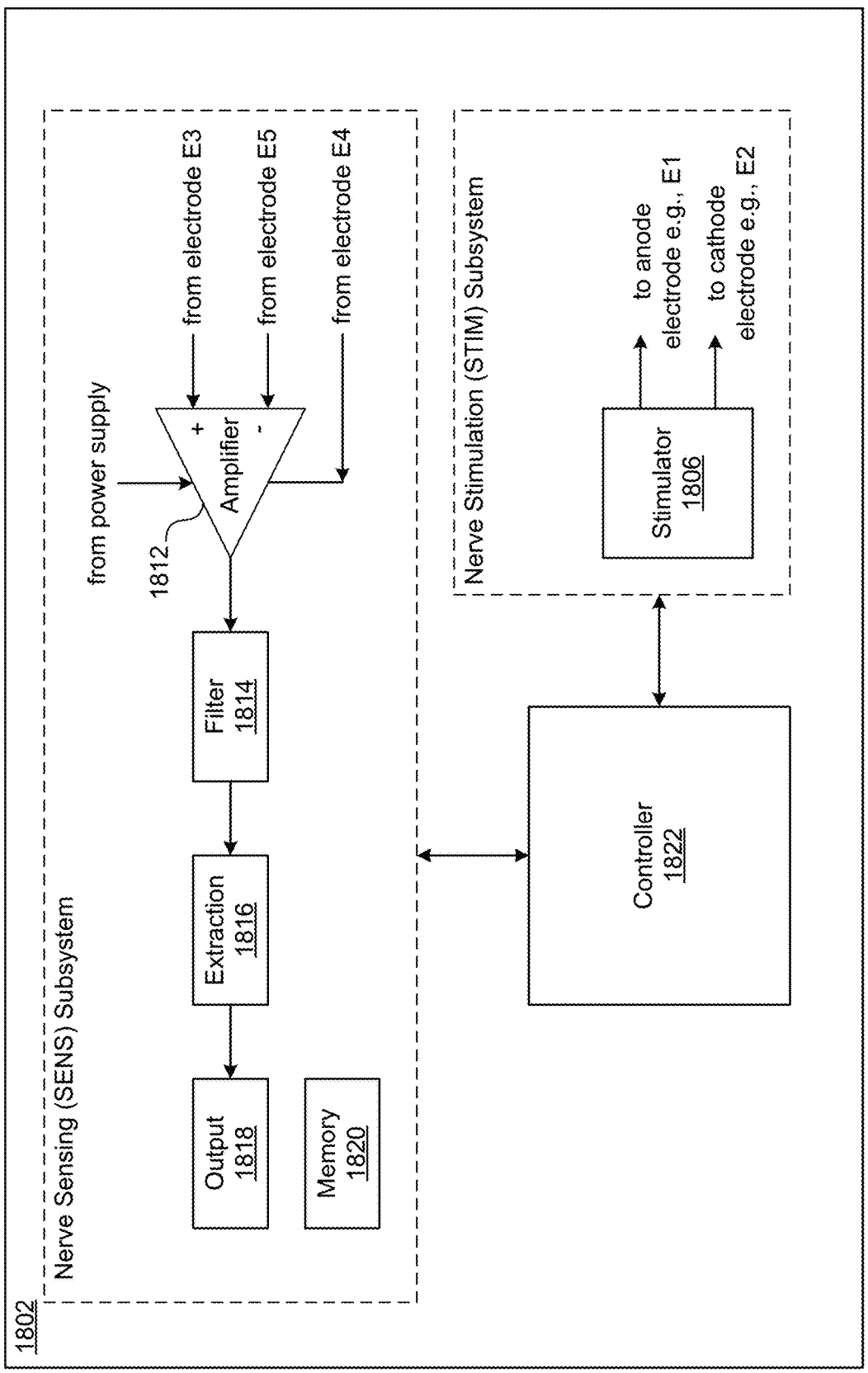
FIG. 18 is another schematic diagram of an example system for interfacing with a patient's arterial nerves.

In accordance with an embodiment, the SENS circuit is based on and includes an Op-Amp (e.g., the amplifier 1812 in FIG. 18). The short duration STIM field propagates instantaneously and saturates the Op-Amp of the SENS circuit for a time period dependent on the intensity of the stimulation that is delivered. The propagation of the evoked action potential typically translates to about 1.0-1.5 mm/ms. In accordance with an embodiment, the STIM circuit is designed to limit saturation of the Op-Amp of the SENS circuitry to about 10 milliseconds (ms), but allows for 20 ms of saturation as a safety factor. This translates to a 2.0 cm separation between the electrodes E2 and E3. Furthermore, another objective is to position the electrodes E2 and E3 such that they straddle the location where nerve destruction mechanism has been applied. In this manner, a failure to detect evoked action potentials indicate that the nerve destructive mechanism was successful.

A further potential design complication is due to the renal anatomy and physiology. Two types of C-fiber nerves communicate with the kidney, efferent and afferent. Efferent nerves communicate from the brain to the kidney, and afferent nerves communicate from the kidney to the brain. Where there is a desire to use the probe assembly to confirm nerve destruction, the probe assembly embodiment summarized above with reference to FIG. 17A is sufficient. However, where there is a desire to use a probe assembly for an objective that is diagnostic, it would be useful provide for nerve and sensing distal to proximal, as well as proximal to distal. Hence, the above mentioned switching circuit could be included such that the stimulation (STIM) circuit can transform from utilizing the electrodes E1 and E2 as anode and the cathode to utilizing the electrode E3 and E5 as the anode and cathode; and the sense (SENS) circuit can transform from utilizing the electrodes E3, E4, and E5 for sensing to utilizing the electrodes E1, E2, and E4 for sensing. Alternatively, as will be discussed below following the discussion of FIG. 17A, the probe 1700b discussed with reference to FIG. 17B can be used where the desire is to stimulate with proximal electrodes and sense with distal electrodes.

Where the probe 1700a in FIG. 17A stimulates using the electrodes E1 and E2 at the distal end of the probe body 1702, and senses an evoked neural response to the stimulation using the electrodes E3 and E5 at the proximal end of the probe body 1702, the probe 1700a is especially useful for analyzing the evoked response of afferent nerves that communicate from an organ (e.g., kidney) to the brain. By contrast, the probe 1700b shown in FIG. 17B, when stimulating using the electrodes E1 and E2 at the proximal end of the probe body 1702, and sensing an evoked neural response to the stimulation using the electrodes E3 and E5 at the distal end of the probe body 1702, is especially useful for analyzing the evoked response of efferent nerves that communicate from the brain to an organ (e.g., kidney). The description of the axial spacings between the electrodes E1-E5 shown in FIG. 17A also applies to the axial spacing between the electrodes E1-E5 shown in FIG. 17B.

Tests have shown that including all of the electrodes E1-E5 on the probe body 1702 provides for the best sensing fidelity, including the best signal-to-noise ratio (SNR), compared to embodiments where one or more of the electrodes that are used for sensing are located on the human body, i.e., is/are skin electrode(s). However, in an alternative embodiment the electrode E4 is located on the human body, i.e., is a skin electrode. This alternative embodiment still provides for a relatively good SNR, just not as good as where the electrode E4 is included on the probe body. In still another embodiment, the electrodes E1 and E4 are skin electrodes configured to be placed on the human body. In a further embodiment, the electrodes E1, E4 and E5 are all skin electrodes configured to be place on the human body. In a further embodiment, the electrode E4 is located on a sheath through which the probe is introduced into an artery. In such an embodiment, the electrode E4 can be located, e.g., near the distal end of the sheath through which the probe exits the sheath and enters an artery (or other blood vessel).

FIG. 18 is a high level block diagram of an electrical control unit (ECU) 1802 that is configured to be in electrical communication with a probe assembly including five electrodes (E1-E5), such as one of the probe assemblies described above with reference to FIG. 17A or 17B. The ECU 1802, and the probe to which the ECU 1802 is electrically coupled, can be referred to more generally as a system 1800. The ECU 1802 can process a received signal to produce an output signal, and present information including information about the output signal, the received signal, or processing information. Such a system can be used, for example, in diagnostic procedures for assessing the status of a patient's nervous activity proximate a blood vessel, wherein the blood vessel can be an artery or a vein.

The ECU 1802 includes a stimulator 1806 electrically coupled to the electrodes E1 and E2 on the probe body 1702. The stimulator 1806, which is part of a STIM circuit or subsystem, can selectively emit electrical signals having a specific voltage, amperage, duration, and/or frequency of application that will cause nerve cell activation. In the configuration shown, the electrode E1 is connected as the stimulation anode and the electrode E2 is connected as the stimulation cathode. Upon receiving the stimulation signal produced by the stimulator 1806, the stimulating electrodes of the probe assembly, i.e., E1 and E2 in this example, can apply electrical energy to a patient's nerves through the arterial wall based on the received signal. As was already discussed above, e.g., with reference to FIG. 13, such stimulus can have any of a variety of known waveforms, such as a sinusoid, a square wave form or a triangular wave form, but not limited thereto. In various examples, the stimulation can be applied for durations between approximately 0.05 ms and approximately 2 ms.

In some configurations, the stimulation of nerves to evoke an elicited potential can cause such a potential to propagate in every direction along the nerve fibers. In some situations, it can be undesirable for such a potential to propagate unnecessarily through the nerve for patient safety and/or desired signal isolation purposes. In some configurations, the propagation of elicited action potentials can be "blocked" by applying an electrical signal to a portion of the nerve. Accordingly, in some embodiments, a probe assembly can include electrodes configured to reduce or eliminate an elicited potential from propagating undesirably. For example, with reference to FIG. 17A, the probe assembly 1702 can include a third stimulating electrode (not shown) that functions as a second anode coupled with E1. The cathode (E2) is positioned between E1 and this third electrode. During the application of a stimulation signal, a blocking stimulation pulse can be applied via the third stimulating electrode to prevent elicited action potentials from travelling proximally along the patient's nerves while permitting the action potential to propagate toward the electrodes that are used to sense the evoke response, which electrodes include the electrodes E3, E4, and E5.

In the embodiment shown in FIG. 17A, discussed above, the electrodes E3, E4, and E5 that are used for sensing the evoked response to the stimulation (delivered by the electrodes E1 and E2) are positioned proximally relative to the electrodes E1 and E2. The electrodes E3, E4, and E5 can be configured to detect electrical signals in the patient's nerves at a location separate from the stimulating electrodes E1 and E2. For example, the electrodes E3, E4, and E5 can be used to detect an elicited potential caused by a stimulus from the electrodes E1 and E2 and propagating toward the organ.

In some embodiments, the ECU 1802 can digitally sample the signal sensed using the electrodes E3, E4, and E5 to receive the electrical signal from the probe. In alternate embodiments, the signal can be recorded as an analog signal. When receiving an electrical signal from the electrodes on the probe, the ECU 1802 can perform filtering and/or other processing steps on the signal. Generally, such steps can be performed to discriminate the signal from the probe from any background noise within the patient's vasculature such that the resulting output is predominantly the signal from nerve cell activation. In some instances, the ECU 1802 can modulate the electrical impedance of the signal receiving portion in order to accommodate the electrical properties and spatial separation of the electrodes mounted on the probe in a manner to achieve the highest fidelity, selectively and resolution for the signal received. For example, electrode size, separation, and conductivity properties can impact the field strength at the electrode/tissue interface.

Additionally or alternatively, the ECU 1802 can comprise a headstage and/or an amplifier to perform any of offsetting, filtering, and/or amplifying the signal received from the probe. In some examples, a headstage applies a DC offset to the signal and performs a filtering step. In some such systems, the filtering can comprise applying notch and/or band-pass filters to suppress particular undesired signals having a particular frequency content or to let pass desired signals having a particular frequency content. An amplifier can be used to amplify the entire signal uniformly or can be used to amplify certain portions of the signal more than others. For example, in some configurations, the amplifier can be configured to provide an adjustable capacitance of the recording electrode, changing the frequency dependence of signal pick-up and amplification. In some embodiments, properties of the amplifier, such as capacitance, can be adjusted to change amplification properties, such as the resonant frequency, of the amplifier.

In the illustrated embodiment of FIG. 18, the ECU 1802 includes an amplifier 1812 including a non-inverting (+) input terminal, an inverting (−) input terminal, a power supply input terminal, and a ground or reference terminal. As can be appreciated from FIG. 18, the non-inverting (+) input terminal is electrically coupled to the electrode E3, the inverting (−) input terminal is electrically coupled to the electrode E5, the power supply input terminal is electrically coupled to a voltage source (e.g., a reference voltage generator), and the ground or reference terminal is electrically coupled to the electrode E4. The amplifier 1812 can include any appropriate amplifier for amplifying desired signals or attenuating undesired signals. In some examples, the amplifier has a high common-mode rejection ratio (CMRR) for eliminating or substantially attenuating undesired signals present in each at each of the sensing electrodes E3 and E5.

In some embodiments, the amplifier 1812 can be adjusted, for example, via an adjustable capacitance or via other attributes of the amplifier.

In the example system 1800 of FIG. 18, the ECU 1802 further includes a filter 1814 for enhancing the desired signal in the signal received via the sensing electrodes E3 and E4. As described, the filter 1814 can include a band-pass filter, a notch filter, or any other appropriate filter to isolate desired signals from the received signals. Similar to the amplifier 1322 discussed above, in some embodiments, various properties of the filter 1812 can be adjusted to manipulate its filtering characteristics. For example, the filter may include an adjustable capacitance or other parameter to adjust its frequency response.

At least one of amplification and filtering of the signal received at the sensing electrodes E3 and E5 can allow for extraction of the desired signal at 1816. In some embodiments, extraction 1816 comprises at least one additional processing step to isolate desired signals from the signal sensed using the sensing electrodes E3 and E5, such as preparing the signal for output at 1818. In some embodiments, the functionalities of any combination of amplifier 1812, filter 1814, and extraction 1816 may be combined into a single entity. For instance, the amplifier 1812 may act to filter undesired frequency content from the signal without requiring additional filtering at a separate filter.

In some embodiments, the ECU 1802 can record emitted stimuli and/or received signals. Such data can be subsequently stored in permanent or temporary memory 1820. The ECU 1802 can comprise such memory 1820 or can otherwise be in communication with external memory (not shown). Thus, the ECU 1802 can be configured to emit stimulus pulses to electrodes of the probe, record such pulses in a memory, receive signals from the probe, and also record such received signal data. While shown in FIG. 18 as being a part of the processor, it will be appreciated that the memory in or associated with the ECU 1802 can be internal or external to any part of the ECU 1802 or the ECU 1802 itself.

The ECU 1802 or separate external processor can further perform calculations on the stored data to determine characteristics of signals either emitted or received via the probe. For example, in various embodiments, the ECU 1802 can determine any of the amplitude, duration, or timing of occurrence of the received or emitted signals. The ECU 1802 can further determine the relationship between the received signal and the emitted stimulus signal, such as a temporal relationship therebetween. In some embodiments, the ECU 1802 performs signal averaging on the signal data received from the probe. Such averaging can act to reduce random temporal noise in the data while strengthening the data corresponding to any elicited potentials received by the probe. An example data collection procedure was discussed above with reference to FIG. 13.

Averaging as such can result in a signal in which temporally random noise is generally averaged out and the signal present in each recorded data set, such as elicited potentials, will remain high. In some embodiments, each iteration of the process can include a synchronization step so that each acquired data set can be temporally registered to facilitate averaging the data. That is, events that occur consistently at the same time during each iteration may be detected, while temporally random artifacts (e.g., noise) can be reduced. In general, the signal to noise ratio (SNR) resulting in such averaging will improve by the square root of the number of samples averaged in order to create the averaged data set.

The ECU 1802 can further present information regarding any or all of the applied stimulus, the signal, and the results of any calculations to a user of the system, e.g., via output 1818. For example, the ECU 1802 can generate a graphical display providing one or more graphs of signal strength vs. time representing the stimulus and/or the received signal. FIG. 9, discussed above, is an example plot of signal strength vs. time illustrating a stimulus signal (shown at the top in FIG. 9) and an associated elicited potential (shown at the bottom in FIG. 9).

In some embodiments, the ECU 1802 can include a controller 1822 in communication with one or both of stimulator 1806 and SENS subsystem 1810. The controller 1822 can be configured to cause stimulator 1806 to apply a stimulation signal to a probe, e.g., the probe 1700*a* or 1700*b*. Additionally or alternatively, the controller 1822 can be configured to analyze signals received and/or output by the SENS subsystem 1810. In some embodiments, the controller 1822 can act to control the timing of applying the stimulation signal from stimulator 1806 and the timing of receiving signals by the SENS subsystem 1810.

Example electrical control units have been described. In various embodiments, the ECU 1802 can emit stimulus pulses to the probe, receive signals from the probe, perform calculations on the emitted and/or received signals, and present the signals and/or results of such calculations to a user. In some embodiments, the ECU 1802 can comprise separate modules for emitting, receiving, calculating, and providing results of calculations. Additionally or alternatively, the functionality of controller 1822 can be integrated into the ECU 1802 as shown, or can be separate from and in communication with the ECU.

In some embodiments, the ECU 1802 can include a switching network configured to interchange which of electrodes (e.g., E1-E5) of the probe are coupled to which portions of the ECU. In some such embodiments, a user can manually switch which inputs receive connections to which electrodes of the probe. Such configurability allows for a system operator to adjust the direction of propagation of the elicited potential as desired.

As noted above, where the probe 1700*a* in FIG. 17A stimulates using the electrodes E1 and E2 at the distal end of the probe body 1702, and senses an evoked neural response to the stimulation using the electrodes E3 and E5 at the proximal end of the probe body 1702, the probe 1700*a* is especially useful for analyzing the evoked response of afferent nerves that communicate from an organ (e.g., kidney) to the brain. As also noted above, where the probe 1700*b* in FIG. 17B stimulates using the electrodes E1 and E2 at the proximal end of the probe body 1702, and senses an evoked neural response to the stimulation using the electrodes E3 and E5 at the distal end of the probe body 1702, the probe 1700*b* is especially useful for analyzing the evoked response of efferent nerves that communicate from the brain to an organ (e.g., kidney).

Figure 19:
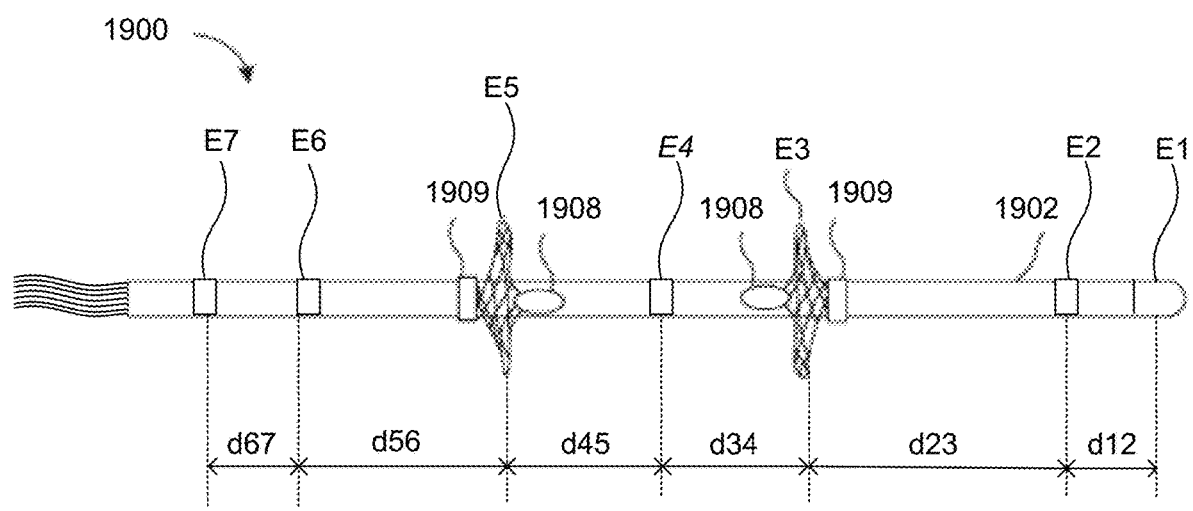
FIG. 19 illustrates an intraluminal microneurography probe according to a further embodiment of the present technology.

Referring now to FIG. 19, the probe assembly 1900 shown therein is designed to be used for analyzing the evoked response of afferent nerves that communicate from an organ (e.g., kidney) to the brain, as well as for analyzing the evoked response of efferent nerves that communicate from the brain to an organ (e.g., kidney). The probe assembly 1900, which can be more succinctly referred to as a probe 1900, includes a probe body 1902 that supports electrodes E1, E2, E3, E4, E5, E5, and E7, with the electrodes E3 and E5 being deployable mesh electrodes, example details of which were discussed above. The deployable mesh electrodes E3 and E5 are shown as being affixed to the probe body at attachment points 1908, and each of the mesh electrodes E3 and E5 is shown as having a respective sliding collar element 1909 located at the end of the mesh electrode opposite attachment point 1908. Details of the attachment points 1908 and the sliding collar elements 1909 can be appreciated from the above discussion of the attachment points 1708 and the sliding collar elements 1709 discussed above with reference to FIGS. 17A and 17B. The mesh electrodes E3 and E5 when non-expanded, or more generally, not deployed, can look similar to the mesh electrodes 206 and 204 shown in and described above with reference to FIG. 2. More specifically, when the mesh electrodes E3 and E5 are in their non-deployed positions, they can confirm to an outer surface of the probe body 1902, or alternatively, they can be retained within one or more inner cavities of the probe body 1902 when they are in their non-deployed positions.

Figure 20:
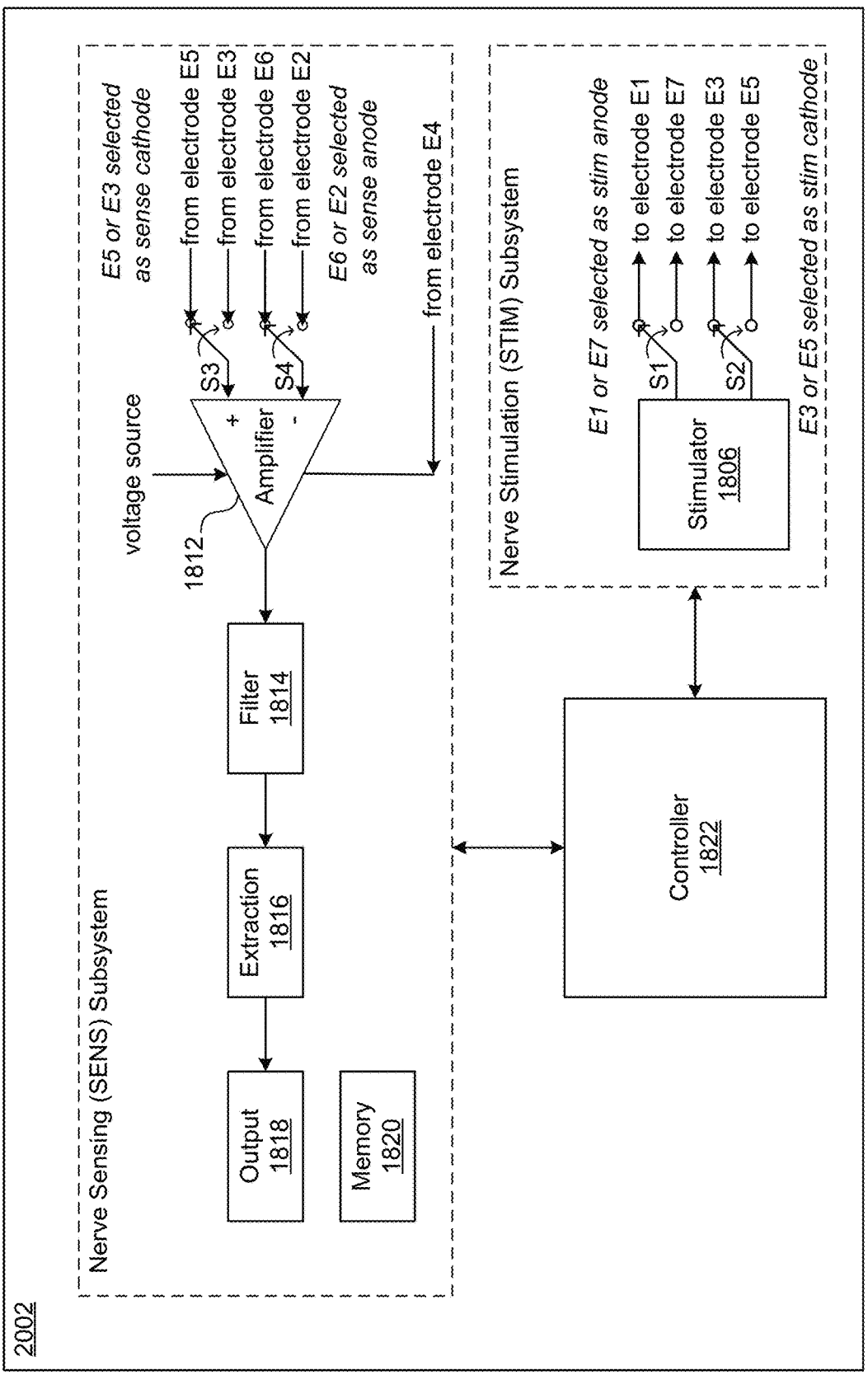
FIG. 20 is a further schematic diagram of an example system for interfacing with a patient's arterial nerves.

The probe 1900 can be used, for example, with the electrical control unit (ECU) 2002, shown in FIG. 20, which is configured to be in electrical communication with a probe assembly including seven electrodes (E1-E7). The ECU 2002, and the probe (e.g., 1900) to which the ECU 2002 is electrically coupled, can be referred to more generally as a system 2000.

Referring to FIG. 20, the elements shown therein that are substantially the same the elements shown in FIG. 18 are labeled the same, and thus need not be described in detail again, since reference can be made to the discussion of FIG. 18 above. The ECU 2002 is shown as having switches S1, S2, S3, and S4, each of which can be referred to as a switch, and collectively can be referred to as switches or a switching circuitry. Subsets of the switches S1-S4 can also be referred to as switches, e.g., the switches S1 and S2 can be referred to as first switches, and the switches S3 and S4 can be referred to as second switches. When the switches are in a first configuration, the probe 1900 (in FIG. 19) stimulates using the electrodes E1 and E3 on the distal portion of the probe body 1902, and senses an evoked neural response to the stimulation using electrodes E5 and E6 on a proximal portion of the probe body 1902, in which configuration the probe 1900 is especially useful for analyzing the evoked response of afferent nerves that communicate from an organ (e.g., kidney) to the brain. When the switches are in a second configuration, the probe 1900 stimulates using the electrodes E7 and E5 on a proximal portion of the probe body 1902, and senses an evoked neural response to the stimulation using electrodes E3 and E2 on a distal portion of the probe body 1902, in which configuration the probe 1900 is especially useful for analyzing the evoked response of efferent nerves that communicate from the brain to an organ (e.g., kidney). In both configurations, the electrode E4 is used as the common electrode for sensing, which can also be referred to as the ground reference electrode, as can be appreciated from FIG. 20. The controller 1822 can be used to control the switches S1, S2, S3, and S4, e.g., in response to user input. In the embodiment shown in FIG. 19, the electrode E4 is supported by the probe body 1902, which should provide for the best sensing fidelity (e.g., signal-to-noise ratio). In an alternative embodiment, the common electrode E4 is a non-implantable skin electrode. While the switches are shown as being within the ECU 2002, it is also possible for some or all of the switches to be within the probe body 1902, or within some other component that is connected between the ECU 2002 and the probe 1900.

Referring to FIG. 19, the electrode E1, which is the most distal electrode, can be a tip electrode or a band electrode (aka ring electrode) located at or in close proximity to the most distal end of the probe body 1902. A center-to-center axial distance between the electrodes E1 and E2, which can be referred to as the distance d12, is within the range of 5 mm to 25 mm (i.e., 0.5 cm to 2.5 cm), with the distance d12 preferably being about 6 mm. The center-to-center axial distance d23, between the electrodes E2 and E3, when the electrode E3 is deployed, is within the range of 2 cm to 6 cm, with the distance d23 preferably being about 3 cm. The center-to-center axial distance d34, between the electrodes E3 and E4, when the electrode E3 is deployed, is within the range of 1 cm to 5 cm, with the distance d34 preferably being about 1.5 cm. The center-to-center axial distance d45, between the electrode E4 and E5, when the electrode E5 is deployed, is within the range of 1 cm to 5 cm, with the distance d45 distance preferably being about 1.5 cm. The center-to-center axial distance d35, between the two deployable electrode E3 and E5, when they are both deployed, is within the range of 2 cm to 10 cm, with the distance d35 preferably being about 3 cm. The center-to-center axial distance d56 between the electrodes E5 and E6, when the electrode E5 is deployed, is within the range of 2 cm to 6 cm, with d56 preferably being about 3 cm. The center-to-center axial distance d67 between the electrodes E6 and E7, is within the range of 5 mm to 25 mm (i.e., 0.5 cm to 2.5 cm), with the distance d67 preferably being about 6 mm.

While the deployable electrodes E3 and E5 in FIG. 19 are show as being mesh electrodes, the deployable electrodes E3 and E5 can alternatively be helical electrodes, similar to the deployable helical electrodes 106 and 104 in FIG. 1. In accordance with certain embodiments, the axial width of each of the band electrodes E1, E2, E4, E6, and E7 is about 1 mm. However, narrower or wider widths for the band electrodes are also possible and within the scope of the embodiments described herein.

Referring briefly back to FIG. 15, shown therein was an example probe 1534 configured for adjustable separation of the stimulating and recording (aka sensing) electrode(s). In FIG. 15, the various electrodes were shown as being band or ring electrodes. In another embodiment, one of the electrodes on the first portion 1532 of the probe (e.g., the more proximal of the two electrodes on the first portion) is a deployable helical electrode (the same or similar to the deployable helical electrodes 104, 106 shown in and described with reference to FIG. 1) or a deployable mesh electrode (e.g., the same or similar to the deployable mesh electrodes 204, 206 shown in and described initially with reference to FIG. 2). Additionally, or alternatively, one of the electrodes on the second portion 1534 of the probe (e.g., the most distal of the three electrodes) can be a deployable helical electrode (the same or similar to the deployable helical electrodes 104, 106 shown in and described with reference to FIG. 1) or a deployable mesh electrode (e.g., the same or similar to the deployable mesh electrodes 204, 206 shown in and described initially with reference to FIG. 2). It is also noted that the most distal one of the electrodes on the first portion 1532 of the probe can be a tip electrode, rather than a band or ring electrode.

Explained another, referring briefly back to FIG. 17A, the probe shown therein can be modified such that the electrodes E1 and E2 are on a first portion of the probe body, and the electrodes E3, E4, and E5 are on a second portion of the probe body, wherein the first portion of the probe body (which is more distal than the second portion) can be axially moved relative to the second portion of the probe body. Such an embodiment would enable the distance between the electrodes E1 and E2 on the first portion of the probe body to be moved either further or closer to the electrodes E3, E4, and E5 on the second portion of the probe body. Such adjustments can be made to accommodate patients that have different sized arteries, different artery lengths, different distances between artery branch points, different artery curvature, and/or to improve the fidelity (e.g., SNR) of a sensed signal. In one such embodiment, only electrodes E3 and E5 are on the second portion of the probe body, and the electrode E4 is either a non-implantable skin electrode or is located on the sheath that is used to introduce the probe into a body.

Figure 17B:
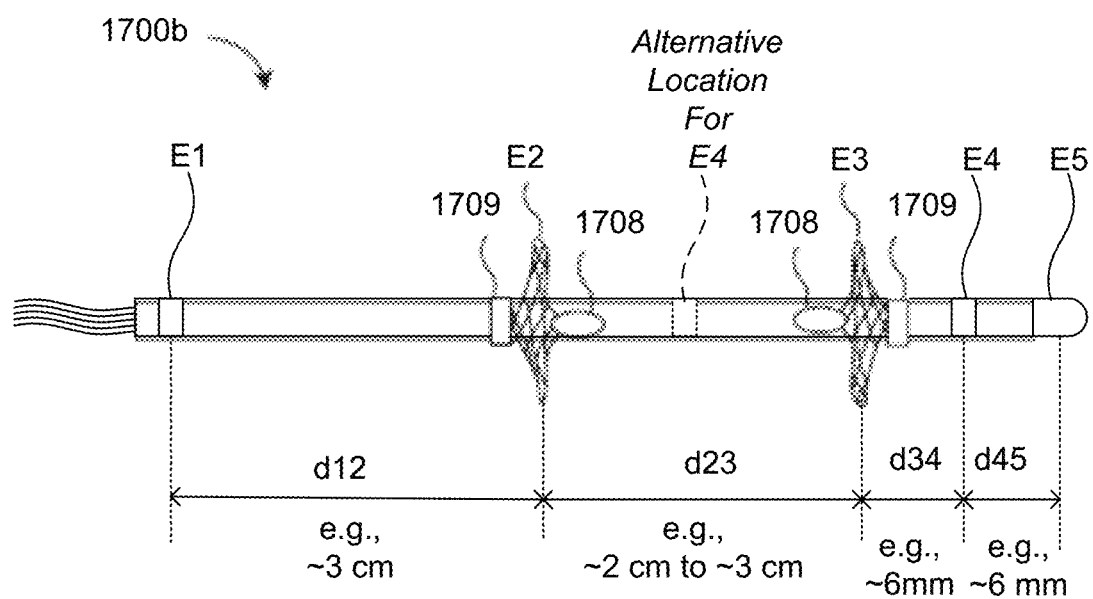
FIG. 17B illustrates an intraluminal microneurography probe according to another embodiment of the present technology.

Similarly, referring briefly back to FIG. 17B, the probe shown therein can be modified such that the electrodes E5, E4, and E3 are on a first portion of the probe body, and the electrodes E2 and E1 are on a second portion of the probe body, wherein the first portion of the probe body (which is more distal than the second portion) can be axially moved relative to the second portion of the probe body. In one such embodiment, only electrodes E5 and E3 are on the first portion of the probe body, and the electrode E4 is either a non-implantable skin electrode or is located on the sheath that is used to introduce the probe into a body. Other variations are also possible and within the scope of the embodiments described herein.

It would also be possible for the probe shown in and described above with reference to FIG. 19 to be modified to be a telescoping type of probe, wherein the electrodes E1, E2, and E3 are located on a first portion of the probe body, and the electrodes E5, E6, and E7 are located on a second portion of the probe body, wherein the first portion of the probe body (which is more distal than the second portion) can be axially moved relative to the second portion of the probe body. The electrode E4 can either be located on the first portion of the probe body or the second portion of the probe body, depending upon the implementation. Alternatively, the electrode E4 can be a non-implantable skin electrode or be located on the sheath that is used to introduce the probe into a body.

In accordance with certain embodiments, a hollow lumen extends through an entire axial length of any one of the probes disclosed herein, and there is an opening at the most distal end of the probe. In such an embodiment, the probe can be delivered through a patient's vasculature or other lumen of the subject either with or without the assistance of a guidewire. Where a guidewire is intended to be used, one or more of the most distal electrodes that were described as being on a distal portion of a probe body can instead be located on a distal portion of the guidewire. For an example, referring briefly back to FIG. 17A, the most distal electrode E1 can be located on the distal end of a guidewire instead of at the distal end of the probe body. For another example, referring briefly back to FIG. 17B, the most distal electrode E5 can be located on the distal end of the guidewire. Referring briefly back to FIG. 19, the most distal electrode E1, or the most distal electrodes E1 and E2, can be located on a distal portion of a guidewire rather than on the distal portion of the probe body. In such embodiments, one or more wires the extend through a channel within the guide wire should be connected to appropriate circuitry within an ECU (e.g., 1802 or 2002). Also, in such embodiment the distal end of the guide wire should extend out the distal end of the probe body during stimulating and sensing for an evoked response to the stimulating. Other variations are also possible and within the scope of the embodiments described herein. The guidewire mounted electrodes would allow the user to vary the sensitivity of the stimulating electrical field or of the sensing by increasing the separation between cathode and anode. In such circumstances the separation range between anode and cathode could exceed the 2.5 cm separation. Guidewire-mounted electrodes could also accommodate patients that have different sized arteries, different artery lengths, different distances between artery branch points, and/or different artery curvature. Mounting electrodes on a guidewire could also provide an advantage such that the member carrying the electrodes and/or the conductors between the electrodes and ECU pass within the catheter. By doing so, these elements would not physically interfere with other catheter functional aspects mounted proximally, such as balloons or electrodes intended to deliver ablative energies to the surrounding tissues around the artery.

In accordance with certain embodiments of the present technology, the deployable electrodes described above in the various probe assemblies are made of Nickel Titanium (NiTi), which is also known as Nitinol. For example, referring back to FIG. 1, in accordance with certain embodiments, each of the deployable helical electrodes 104 and 106 is made of a respective Nitinol wire. For another example, referring back to FIG. 2, in accordance with certain embodiments, each of the deployable mesh electrodes 204 and 206 is made of a plurality of Nitinol wires that are braided together and electrically coupled to one another to form a mesh electrode. For still another example, in accordance with certain embodiments, each of the deployable mesh electrodes E3 and E2 in FIG. 17A or 17B (which are also labeled 1704 and 1706) is made of a plurality Nitinol wires that are braided together and electrically coupled to one another to form a mesh electrode. In contrast to prior electrodes (e.g., prior basket electrodes) that may have used Nitinol as an underlying support frame for holding multiple discrete electrodes, in accordance with certain embodiments of the present technology, each deployable electrode itself (that is used for delivering nerve stimulation, or is used for sensing nerve activity) is made of one or more Nitinol wires. A benefit of make each of the deployable electrodes out of one or more Nitinol wires is that such an electrode can be made to have high elasticity and have shape memory such that the electrode can be moved between non-deployed and deployed positions, and will have a desired and expected shape when the electrode is in its deployed position.

In accordance with certain embodiments, the mesh electrodes described herein (e.g., 204 and 206, 1704 and 1706) are each braided from a number N of Nitinol wires, where the number N is within the range of 8 to 24, and is preferably 16. Each of the Nitinol wires can have a diameter in the range of 0.002 inches and 0.006 inches, with the diameter preferably being about 0.004 inches. In accordance with certain embodiments, the mesh electrode is configured to have an outer diameter (OD) of 6.75 mm+/−0.25 mm when fully deployed. Experiments have shown that a deployed mesh electrode of such an outer diameter (OD) is of the appropriate size to make good contact with the renal arteries of most human patients. Additional electrode sizes can be made to accommodate the range of blood vessel diameters.

Prior to braiding the Nitinol wires to produce the mesh electrode, each of the Nitinol wires can have a light oxide finish. The wires can be braided over a mandrel, or other type of fixture, to a desired deployed shape (e.g., such as the generally bulbous shape shown in FIGS. 2 and 17), wherein the resulting mesh electrode is designed to prevent expansion, when fully deployed, past an outer diameter of about 7.0 mm. After being braided, the braided Nitinol wires can be heat treated to have an austenite finish temperature (Af) that is at or below room temperature. Thereafter, the braided and heat treated Nitinol wires can be chemically processed to remove the oxide layer and then passivated to thereby improved the resulting mesh electrode's resistance to corrosion. While the deployable mesh electrodes (and deployable helical electrodes) described herein are preferably made of Nitinol, it is also possible and within the scope of the embodiments described herein that such deployable electrodes can be made from another metal or alloy.

In accordance with certain embodiments, one or more of the mesh electrodes (or helical electrodes) is coated with a noble metal or noble alloy coating to improve the performance of the mesh electrode(s) as a biological electrode, since such noble metals and alloys are resistant to oxidation and corrosion. Example types of noble metals or alloys that can be used include, but are not limited to, platinum, platinum-iridium, platinum black, or gold.

In certain embodiments, no portion of mesh electrodes is coated with an electrically insulating material, which can also be referred to as an electrical insulator. In other words, in such embodiments an entirety of each mesh electrode is left uninsulated. In other embodiments, at least a portion of at least one of the mesh electrodes coated with an electrically insulating material, such as, but not limited to, Parylene. The capacitance associated with a biological electrode is generally related to an amount of surface area of the electrode that is exposed to blood, whereby the greater the amount of surface area that is exposed to blood generally the greater the capacitance. To improve the fidelity (e.g., signal-to-noise ratio (SNR)) of the sensed signal, it is desirable to keep the capacitance associated with the biological electrode as low as possible. Accordingly, in order to reduce the capacitance of a mesh electrode, portions of the mesh electrode that are not intended to come into contact with an arterial (or other blood vessel) wall are coated with an electrical insulator to maintain the capacitance associated with the electrode below a desired level. However, it is noted that the electrically insulating coating should be applied in such a manner that it does not interfere with a mesh electrode's ability to transition from its non-deployed to deployed positions, and vice versa. In accordance with an embodiment, prior to the electrically insulating coating being applied to a braided mesh electrode, the portion of the mesh electrode that is intended to come into contact with an arterial (or other blood vessel) wall is masked or shielded, and then the electrically insulating coating is applied, e.g., by chemical vapor deposition, but not limited thereto. Thereafter, the mask or shielding is removed to expose the portion of the mesh electrode that is intended to come into contact with an arterial wall. Other techniques for coating just one or more specific portions of the mesh electrode with an electrically insulating material are also possible and within the scope of the embodiments described herein.

The mesh electrodes can be braided such that when deployed the plurality of openings in the mesh, which allow blood flow therethrough, are generally of about the same size. Alternatively, the mesh electrodes can be braided such that there are a few larger openings in the mesh at the expense of the remaining openings being smaller. Such larger openings in the mesh electrodes should beneficially provide for improved blood flow through the artery that includes the deployed mesh electrode.

Figure 21C:
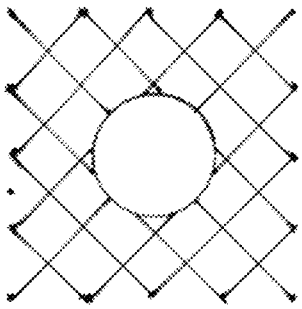
FIG. 21C shows a portion of the mesh electrode wherein an opening in the mesh electrode has been enlarged to improve blood flow through the mesh electrode.
Figure 21B:
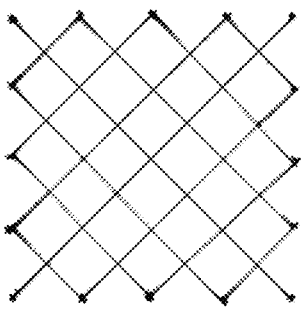
FIG. 21B shows a portion of the mesh electrode wherein the openings in the mesh electrode are generally about the same size.
Figure 21A:
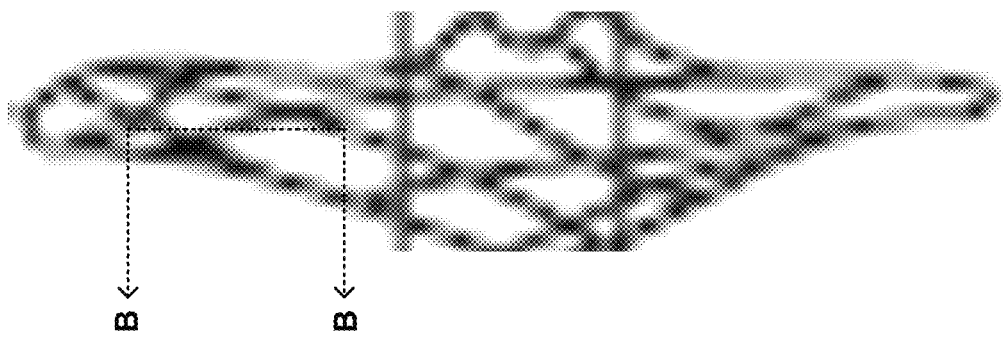
FIG. 21A shows a side view of an example mesh electrode.

FIG. 20A shows a side view of a mesh electrode (e.g., 204 or 206 in FIG. 2, E3 or E2 in FIG. 17A or 17B, or E5 or E3 in FIG. 19) in its deployed position, wherein the mesh electrode that is made by braiding a plurality of wires (e.g., Nitinol wires). FIG. 21B shows an example portion of the mesh electrode (corresponding to the section B-B in FIG. 21A), from a site line that is parallel to the axis of the probe body about which the mesh electrode expands. In other words, a portion of a front view of the mesh electrode in its expanded position is shown in FIG. 21B. As can be appreciated from FIG. 21B, each of the openings in the mesh are of about the same size. FIG. 21C shows how a portion of the mesh, shown in FIG. 21B, can be modified to increase the size of individual openings in the mesh, to improve blood flow through a mesh electrode when its in its deployed position. The enlarged opening in the mesh can be produced, for example, by inserting a mandrel, awl, or other type of tool or fixture through an interstice and displacing the braid away from the fixture and creating a larger opening prior to or while the mesh electrode (e.g., made of braided Nitinol wires) is shape set in its desired deployed configuration shape. The perspectives in FIGS. 21B and 21C is axially down the mesh and the braid portrayed is that displaced 90° from the axis to form circumferential contact with an arterial wall. Several enlarged openings can be created in the deployed section of the mesh electrode through which blood will flow. The benefit would be improved blood flow through the deployed mesh electrode. Similar configuration can also be provided with other types of deployable electrodes besides deployable mesh electrodes to improve blood flow.

In clinical use, any one of the probes described herein, e.g., with reference to FIGS. 1, 2, 5, 13, 17A, 17B, and 19, but not limited thereto, can be used with a sheath that serves as a conduit through which the probe is inserted into an artery (or other blood vessel). The distal end of the sheath is typically positioned within the opening of the desired artery, e.g., the renal artery. The sheath is used to guide the probe to the desired artery, e.g., the renal artery lumen. Depending upon patient anatomy, the user (e.g., clinician) may need to retract the sheath in order to expose the most proximal electrode on the probe, such as the electrode E5 in FIG. 17A, the electrode E1 in FIG. 17B, or the electrode E7 in FIG. 19. An alternative would be to manufacture a sheath with an electrode located near its distal tip, which can be connected as and function as the most distal electrode. Another alternative would be to use a skin electrode in place of the most distal electrode. Other variations are also possible and within the scope of the embodiments described herein.

In certain embodiments, the various probes described herein, e.g., with reference to FIGS. 1, 2, 13, 17A, 17B, and 19, are used for analyzing neural activity of nerves that surround an artery near an organ of a body, but such probes are not capable of performing denervation. In such embodiments, any known or future develop arterial ablation device can be used to perform denervation, and one of the probes disclosed herein can be used to determine the efficacy of the denervation, e.g., renal denervation, but not limited thereto. In other embodiments, an RF ablation antenna, or some other ablation mechanism, is incorporated into any one of the probes disclosed herein, wherein various examples of such RF ablation antenna were described above with reference to FIGS. 5 and 6. For an example, any of the probes described herein can be used by a clinician to measure nerve activity such as renal nerve activity by emitting an electrical pulse through stimulation electrodes in the probe, and recording propagation along renal nerve fibers using the sense electrode or electrodes on the probe. The clinician can then compare renal nerve activity pre- and post-denervation to determine the degree of nerve ablation incurred, thereby more accurately achieving the desired degree of nerve ablation during treatment of the patient. For a more specific example, a clinician can apply an electrical stimulus to a site in the proximal renal artery, and then monitor or record the nerve activity between the stimulus site and the kidney (and/or between the stimulus site and the spinal column), thereby measuring the resultant downstream (and/or upstream) action potential in the nerves. Nerve ablation can then be performed, and the stimulus and measurement of the nerve is repeated to verify a reduced or eliminated evoked potential detected in the nerve as a result of stimulation via the probe's electrodes.

More generally, various techniques can be used to partially or completely incapacitate neural pathways, such as those innervating the kidney. Renal neuromodulation, in accordance with embodiments of the present technology, can be electrically-induced, thermally-induced, chemically-induced, or induced in another suitable manner or combination of manners at one or more suitable treatment locations during a treatment procedure. For example, the purposeful application of radiofrequency (RF) energy (monopolar and/or bipolar), pulsed RF energy, microwave energy, optical energy, ultrasound energy (e.g., delivered by catheter, extracorporeal, high-intensity focused ultrasound (HIFU)), cryotherapeutic energy, direct heat energy, radiation (e.g., infrared, visible, gamma), chemicals (e.g., drugs or other agents), or combinations thereof to tissue at a treatment location can induce one or more desired effects at the treatment location, e.g., broadly across the treatment location or at localized regions of the treatment location. The treatment location can be proximate (e.g., at or near) a vessel or chamber wall (e.g., a wall of a renal artery, a ureter, a renal pelvis, a major renal calyx, a minor renal calyx, and/or another suitable structure), and the treated tissue can include tissue proximate the treatment location. For example, with regard to a renal artery, a treatment procedure can include modulating nerves in the renal plexus, which lay intimately within or adjacent to the adventitia of the renal artery.

The various probes described herein were often described as being used to analyze neural activity of nerves that surround an artery near an organ (e.g., a kidney) of a body. However, it is noted that such probes can be used with other types of blood vessels besides arteries. More specifically, it would also be possible to insert such probes into a vein instead of an artery. Accordingly, it could be more generally stated that the probes described herein can be used to analyze neural activity of nerves that surround a blood vessel.

In accordance with certain embodiments, each deployable mesh, basket or helical electrode (or other type of deployable electrode) that is used as a sense cathode is a single (aka unitary) electrode that, when in its deployed position, has an outer circumference that simultaneously contacts multiple contiguous and/or non-contiguous locations spaced about a 360 degree segment of an inner wall of a biological lumen, such as an artery or vein. Additionally, or alternatively, each deployable mesh, basket or helical electrode (or other type of deployable electrode) that is used as a stimulation electrode is a single (aka unitary) electrode that, when in its deployed position, has an outer circumference that simultaneously contacts multiple contiguous and/or non-contiguous locations spaced about a 360 degree segment of an inner wall of a biological lumen, such as an artery or vein. Examples of such deployable electrodes include, but are not limited to, the helical electrodes 104 and 106 in FIG. 1, the mesh electrodes 204 and 206 in FIG. 2, the electrodes E2 and E3 in FIGS. 17A and 17B, and the electrodes E3 and E5 in FIG. 19. In certain such embodiments, such a deployable unitary electrode (e.g., a deployable mesh or basket electrode) is configured to contact multiple non-contiguous locations such that there are gaps of no more than 30 degrees between where the outer periphery of the deployable unitary electrode contacts the multiple non-contiguous locations about a 360 degree segment of an inner wall of a biological lumen, such as an artery or vein. In specific such embodiments, the gaps are of no more than 20 degrees, are of no more than 15 degrees, are of no more than 10 degrees, or are of no more than 5 degrees.

In accordance with certain embodiments, a deployable unitary electrode that is configured to be used as a sense electrode, or as a stimulation electrode, is configured to cumulatively contact at least 245 degrees of a 360 degree segment of an inner wall of the biological lumen, when the deployable unitary electrode is in its deployed position. In specific such embodiments, such a deployable unitary electrode is configured to cumulatively contact at least 280 degrees, or at least 300 degrees, of a 360 degree segment of an inner wall of a biological lumen, when the deployable unitary electrode is in its deployed position.

Additionally, in certain embodiments, each unitary deployable mesh basket or helical electrode (or other type of deployable electrode) is electrically connected to a respective single electrically conductive wire that extends through a channel or lumen within the probe body that supports the deployable electrode. Such embodiments provide for a greater signal to noise ratio (SNR), compared to if multiple independent sense electrodes are attached to an underlying deployable structure with respective multiple electrically conductive wires (electrically connected to the multiple sense electrodes) extending through a channel or lumen of the probe body. A further benefit of such embodiments is that it simplifies nerve assessment of a denervation procedure.

Similarly, in accordance with certain embodiments, each deployable mesh, basket or helical electrode (or other type of deployable electrode) that is used as a stimulation cathode is a single (aka unitary) electrode that, when in its deployed position, has an outer circumference that simultaneously contacts multiple contiguous and/or non-contiguous locations spaced about a 360 degree segment of an inner wall of a biological lumen. Additionally, in certain embodiments, each unitary deployable electrode electrically that is used as a stimulation cathode is connected to a respective single electrically conductive wire that extends through a channel or lumen within the probe body that supports the deployable electrode. A benefit of having a deployable electrode that is used as a stimulation cathode be a single (unitary) electrode that simultaneously contacts multiple locations spaced about a 360 degree segment of an inner wall of a biological lumen, and that is connected to a single electrically conductive wire that extends through a channel or lumen within the probe body that supports the deployable electrode, is that it may provide for a more uniform stimulating field around the entire circumference of the deployable electrode, and thus, a more unform stimulation of a segment of the biological lumen that is in contact with the deployable electrode. In alternative embodiments, rather than an electrode being connected to only a single electrically conductive wire that extends through a channel or lumen within the probe body, multiple (e.g., two or more wires) can be used in place of the single electrically conductive wire, wherein such multiple wires may be parallel with one another.

The various probes and techniques described herein were often described as being used to analyze the neural activity of renal nerves that surround the renal arteries, which carry blood from the heart to the kidneys. However, it is noted that the probes and techniques described herein can alternatively or additionally be used to analyze the activity of other types of nerves that surround other types of arteries, or more generally, other types of blood vessels. For example, the probes and techniques described herein can be used to analyze the neural activity of nerves that surround the hepatic artery that delivers oxygenated blood to the liver, and/or to analyze the neural activity of nerves that surround the hepatic portal vein that delivers deoxygenated blood from the small intestine to the liver. For another example, the probes and techniques described herein can be used to analyze the neural activity of nerves that surround one or more pancreatic branches of the splenic artery that delivers blood to the pancreas. For still another example, the probes and techniques described herein can be used to analyze the neural activity of nerves that surround one or more mesenteric arteries that deliver blood to the intestines. For a further example, the probes and techniques described herein can be used to analyze the neural activity of nerves that surround the pulmonary arteries and veins that deliver blood to and from the lungs. These are just a few examples of the types of blood vessels and organs with which embodiments of the present technology can be used. The probes described herein can also be used to analyze neural activity of nerves that surround other types of biological lumen besides blood vessels, such as, but not limited to the gastrointestinal tract pathways of bronchi in the lungs, pathways of the genitourinary tract, and airway passages such as the trachea. Where such a probe is also configured to perform denervation using an ablation mechanism, the probe can be used to perform denervation of any of the aforementioned blood vessels or other biological lumen, but not limited thereto, as well as to analyze the efficacy of the denervation.

The various different probes described herein, e.g., with reference to FIGS. 1, 2, 5, 13, 15, 17A, 17B, and 19, and the stimulating and sensing circuits or subsystems described herein, e.g., with reference to FIGS. 4, 13, 18, and 20, can be used determine whether a denervation procedure should be performed, as well as to determine the efficacy of a denervation procedure that has been performed and to determine whether further denervation should be performed, using one or more of the methods described herein, e.g., with reference FIGS. 11 and 14. Such probes can alternatively, or additionally, be used for diagnostic purposes, e.g., by using such probes to perform the method summarized above with reference to FIG. 16, to detect signals indicative of spontaneous or native activity of nerves the surround a biological lumen.

Various examples of systems and methods have been described. The description provided herein is exemplary in nature and is not intended to limit the scope, applicability, or configuration of the invention in any way. Rather, the description provides practical illustrations for implementing various example embodiments. Examples of constructions, materials, dimensions, and manufacturing processes are provided for selected elements, and all other elements employ that which is known to those of skill in the field. Those skilled in the art will recognize that many of the examples provided have suitable alternatives that can be utilized. These and others are within the scope of the following claims.

Although the examples presented here primarily illustrate measurement of nerve activity using the probe systems described herein, probe systems such as those illustrated herein can also be used to monitor organ activity, pain, or other nervous system indicia. For example, pain can be monitored during surgery in some applications, or nerve activity can be measured while externally stimulating an organ.

Although specific embodiments have been illustrated and described herein, any arrangement that achieve the same purpose, structure, or function may be substituted for the specific embodiments shown. This application is intended to cover any adaptations or variations of the example embodiments of the invention described herein. These and other embodiments are within the scope of the following claims and their equivalents.

What is claimed is:

1. A system for use in analyzing neural activity of nerves that surround a biological lumen, the system comprising:
 a probe body configured to be introduced into the biological lumen;
 a plurality of electrodes supported by the probe body and electrically isolated from one another;
 a stimulator electrically coupled to and configured to deliver electrical stimulation via a first pair of the plurality of electrodes E1 and E2 to evoke neural activity by the nerves that surround the biological lumen;
 an amplifier configured to produce a sensed signal indicative of evoked neural activity and/or indicative of intrinsic neural activity by the nerves that surround the biological lumen;
 the amplifier including a pair of input terminals, an output terminal, and a ground reference terminal;
 wherein a second pair of the plurality of electrodes E3 and E5 is electrically coupled to the pair of input terminals of the amplifier to thereby enable the amplifier to produce the sensed signal;
 wherein at least one of the plurality of electrodes included in the second pair of the electrodes is not included in the first pair of the plurality of electrodes; and
 wherein a remaining one of the plurality of electrodes E4, which is not included in either the first or the second pairs of the plurality of electrodes, is electrically coupled to the ground reference terminal of the amplifier;
 wherein an axial distance between the electrodes E1 and E2 is within a range of 1 cm to 6 cm, inclusive;
 an axial distance between the electrodes E2 and E3 is within a range of 1 cm to 10 cm, inclusive, when the electrode E3 is in the deployed position;
 an axial distance between the electrodes E3 and E4 is within a range of 0.25 cm to 2.5 cm, inclusive, when the electrode E3 is in the deployed position; and
 an axial distance between the electrodes E4 and E5 is within a range of 0.25 cm to 2.5 cm, inclusive.

2. The system of claim 1, wherein:
 the probe body includes a distal end and a proximal end, with the distal end being configured to be placed closer to an organ than the proximal end;
 the plurality of electrodes include electrodes E1, E2, E3, E4, and E5;
 the first pair of the electrodes, which is electrically coupled to the stimulator, comprises the electrodes E1 and E2;
 the second pair of the electrodes, which is electrically coupled to the pair of input terminals of the amplifier, comprises the electrodes E3 and E5; and
 the remaining one of the electrodes, which is electrically coupled to the reference ground terminal of the amplifier, comprises the electrode E4.

3. The system of claim 2, wherein:
 each of the electrodes E2 and E3 comprises a deployable electrode that can be selectively transitioned between a non-deployed position and a deployed position; and
 when a respective one of said deployable electrodes is in the deployed position, at least a portion of the respective one of said deployable electrodes extends away from the probe body such that an outer periphery of the respective one of said deployable electrodes in the deployed position contacts an inner circumference of the biological lumen in which the probe body is introduced.

4. The system of claim 3, wherein at least one of the deployable electrodes E2 and E3 comprises a deployable mesh, basket, or helical electrode.

5. The system of claim 3, wherein at least one of the deployable electrodes E2 and E3 comprises a deployable electrode made from a respective plurality of wires that are electrically connected to one another.

6. The system of claim 4, wherein a portion of a respective one of said deployable electrodes, which portion does not contact the biological lumen when said respective one of said deployable electrodes is in the deployed position, is electrically insulated.

7. The system of claim 5, wherein a respective one of said deployable electrodes includes a plurality of openings through which blood can flow when the deployable electrode is in the deployed position, and wherein a least some openings in a first portion of the respective one of said deployable electrodes, which first portion does not contact the biological lumen in which the probe body is introduced when the respective one of said deployable electrodes is in the deployed position, are at least twice as large as all openings in a second portion of the respective one of said deployable electrodes, which second portion contacts the biological lumen in which when the respective one of said deployable electrodes is in the deployed position.

8. The system of claim 2, wherein the electrodes E1, E2, E3, E4, and E5 are axially spaced apart from one another in that order, with the electrode E1 being one of the electrodes at or closest to the distal end of the probe body, and the electrode E5 being one of the electrodes at or closest to the proximal end of the probe body.

9. The system of claim 2, wherein the electrodes E1, E2, E3, E4, and E5 are axially spaced apart from one another in that order, with the electrode E5 being one of the electrodes at or closest to the distal end of the probe body, and the electrode E1 being one of the electrodes at or closest to the proximal end of the probe body.

10. The system of claim 1, wherein:
 at least one of the electrodes of the second pair of the plurality of electrodes comprises a deployable unitary electrode that can be selectively transitioned between a non-deployed position and a deployed position and is configured as a sense electrode to sense neural activity by the nerves that surround the biological lumen.

11. The system of claim 10, wherein:
 the deployable unitary electrode, that is configured to be used as the sense electrode, is configured to simultaneously contact the multiple contiguous non-contiguous locations such that there are gaps of no more than 30 degrees between where the outer periphery of the deployable unitary electrode contacts the multiple non-contiguous locations about a 360 degree segment of an the inner wall of the biological lumen.

12. The system of claim 11, wherein:
 the deployable unitary electrode, that is configured to be used as the sense electrode, is configured to simultaneously contact multiple non-contiguous locations such that there are gaps of no more than 30 degrees between where the outer periphery of the deployable unitary electrode contacts the multiple non-contiguous locations about a 360 degree segment of an inner wall of the biological lumen.

13. The system of claim 10, wherein:
the deployable unitary electrode, that is configured to be used as the sense electrode, is configured to cumulatively contact at least 245 degrees of a 360 degree segment of an the inner wall of the biological lumen, when the deployable unitary electrode is in its deployed position.

14. The system of claim 10, wherein:
an entire electrically conductive portion of the deployable unitary electrode, that is configured to be used as the sense electrode, is electrically connected to a same one of the terminals of the amplifier configured to produce the sensed signal.

15. The system of claim 14, wherein:
the entire electrically conductive portion of the deployable unitary electrode, that is configured to be used as the sense electrode, is electrically connected to the same one of the terminals of the amplifier via a single electrically conductive wire that extends through a channel or lumen within the probe body that supports the deployable unitary electrode.

16. The system of claim 10, wherein:
one of the electrodes of the first pair of comprises a deployable mesh electrode that can be selectively transitioned between a non-deployed position and a deployed position and is configured to be used as a simulation electrode;
the deployable mesh electrode that is configured to be used as the stimulation electrode comprises a unitary electrode that when in the deployed position has an outer circumference that simultaneously contacts multiple locations about a 360 degree segment of an inner wall of a biological lumen; and
the deployable mesh electrode that is configured to be used as the stimulation electrode is electrically connected to a single electrically conductive wire that extends through a channel or lumen within the probe body that supports the deployable electrode.

17. A system for use in analyzing neural activity of nerves that surround a biological lumen near an organ of a body, the system comprising:
a probe body configured to be introduced into the biological lumen near the organ of the body;
a plurality of electrodes, including electrodes E1, E2, E3, E4, and E5 supported by the probe body, and electrically isolated from one another;
a stimulator electrically coupled to and configured to deliver electrical stimulation via the electrodes E1 and E2 to evoke neural activity by the nerves that surround the biological lumen;
an amplifier configured to produce a sensed signal indicative of evoked neural activity and/or indicative of intrinsic neural activity by the nerves that surround the biological lumen;
the amplifier including first and second input terminals, an output terminal, and a ground reference terminal;
wherein the electrodes E3 and E5 are electrically coupled to the first and second input terminals of the amplifier, respectively, to thereby enable the amplifier to produce the sensed signal indicative of evoked neural activity and/or indicative of intrinsic neural activity by the nerves that surround the biological lumen;
wherein the electrode E4 is electrically coupled to the ground reference terminal of the amplifier;
wherein each of the electrodes E2 and E3 comprises a deployable electrode that is supported by the probe body and can be selectively transitioned between a non-deployed position and a deployed position; and
when said deployable electrodes are in the deployed position, at least a portion of the deployable electrode extends away from the probe body such that an outer circumference of the deployable electrode in the deployed position contacts at least a portion of an inner circumference of the biological lumen in which the probe body is introduced;
wherein an axial distance between the electrodes E1 and E2 is within a range of 1 cm to 6 cm, inclusive;
an axial distance between the electrodes E2 and E3 is within a range of 1 cm to 10 cm, inclusive, when the electrode E3 is in the deployed position;
an axial distance between the electrodes E3 and E4 is within a range of 0.25 cm to 2.5 cm, inclusive, when the electrode E3 is in the deployed position; and
an axial distance between the electrodes E4 and E5 is within a range of 0.25 cm to 2.5 cm, inclusive.

18. The system of claim 17, wherein the electrodes E1, E2, E3, E4, and E5 are axially spaced apart from one another in that order, with the electrode E1 being one of the electrodes at or closest to the distal end of the probe body, and the electrode E5 being one of the electrodes at or closest to the proximal end of the probe body.

19. The system of claim 17, wherein the electrodes E1, E2, E3, E4, and E5 are axially spaced apart from one another in that order, with the electrode E5 being one of the electrodes at or closest to the distal end of the probe body, and the electrode E1 being one of the electrodes at or closest to the proximal end of the probe body.

20. The system of claim 17, wherein at least one of the deployable electrodes E2 and E3 comprises a deployable mesh, helical, or basket electrode.

21. The system of claim 17, wherein at least one of the deployable electrodes E2 and E3 comprises a deployable electrode made from a respective plurality of wires that are electrically connected to one another.

22. The system of claim 21, wherein a portion of a respective one of said deployable electrodes, which portion does not contact the biological lumen when said respective one of said deployable electrodes is in the deployed position, is electrically insulated.

23. The system of claim 21, wherein a respective one of said deployable electrodes includes a plurality of openings through which blood can flow when the deployable electrode is in the deployed position, and wherein a least some openings in a first portion of the respective one of said deployable electrodes, which first portion does not contact the biological lumen in which the probe body is introduced when the respective one of said deployable electrodes is in the deployed position, are at least twice as large as all openings in a second portion of the respective one of said deployable electrodes, which second portion contacts the biological lumen in which when the respective one of said deployable electrodes is in the deployed position.

24. The system of claim 17, wherein:
at least one of the E2 and E3 electrodes comprises a deployable electrode that can be selectively transitioned between a non-deployed position and a deployed position and is configured to be used as a sense electrode;
the deployable electrode that is configured to be used as the sense electrode comprises a deployable unitary electrode that when in the deployed position has an outer periphery that simultaneously contacts multiple contiguous and/or non-contiguous locations spaced about a 360 degree segment of an inner wall of a biological lumen; and the deployable unitary electrode that is configured to be used as the sense electrode is electrically connected to a same one of the terminals of the amplifier configured to produce the sensed signal.

25. The system of claim 24, wherein:
the deployable unitary electrode, that is configured to be used as the sense electrode, is configured to cumulatively contact at least 245 degrees of a 360 degree segment of an inner wall of the biological lumen, when the deployable unitary electrode is in its deployed position.

26. A system for use in analyzing neural activity of nerves that surround a biological lumen, the system comprising:
a probe body configured to be introduced into the biological lumen;
a plurality of electrodes including electrodes E1, E2, E3, E4, E5, E6, and E7 electrically isolated from one another, wherein at least the electrodes E1, E2, E3, E4, E5, E6, and E7 are supported by the probe body and are axially spaced apart from one another in that order;
a stimulator electrically coupled to and configured to deliver electrical stimulation via a selected two of the electrodes to evoke neural activity by the nerves that surround the biological lumen;
an amplifier configured to produce a sensed signal indicative of evoked neural activity and/or indicative of intrinsic neural activity by the nerves that surround the biological lumen;
the amplifier including first and second input terminals, an output terminal, and a ground reference terminal;
first switches that enable a selection between connecting the electrodes E1 and E3 to the stimulator when the first switches are in a first configuration, and connecting the electrodes E7 and E5 to the stimulator when the first switches are in a second configuration;
second switches that enable a selection between connecting the electrodes E5 and E6 to the first and second input terminals of the amplifier when the second switches are in a first configuration, and connecting the electrodes E3 and E2 to the amplifier when the second switches are in a second configuration; and
wherein the electrode E4 is electrically coupled to the ground reference terminal of the amplifier.

* * * * *